(12) United States Patent
Karumanchi et al.

(10) Patent No.: US 11,513,097 B1
(45) Date of Patent: Nov. 29, 2022

(54) METHODS OF OBTAINING AND USING ELECTROCHEMICAL DIAGNOSTIC RESULTS

(71) Applicant: PERSOWN, Inc., Jacksonville, FL (US)

(72) Inventors: Devi Kalyan Karumanchi, Chicago, IL (US); Michelle Kelly, Oak Brook, IL (US); William D. Meadow, Jacksonville, FL (US)

(73) Assignee: PERSOWN, INC., Jacksonville, FL (US)

( * ) Notice: Subject to any disclaimer, the term of this patent is extended or adjusted under 35 U.S.C. 154(b) by 0 days.

(21) Appl. No.: 17/566,836

(22) Filed: Dec. 31, 2021

Related U.S. Application Data

(60) Provisional application No. 63/235,433, filed on Aug. 20, 2021, provisional application No. 63/232,720, (Continued)

(51) Int. Cl.
*G01N 27/49* (2006.01)
*G01N 27/327* (2006.01)
(Continued)

(52) U.S. Cl.
CPC ......... *G01N 27/49* (2013.01); *G01N 27/3272* (2013.01); *G01N 27/3277* (2013.01);
(Continued)

(58) Field of Classification Search
CPC ............... G01N 27/49; G01N 27/3272; G01N 27/3277; G01N 33/56983; G01N 33/6893; G01N 33/54306; G01N 33/553
See application file for complete search history.

(56) References Cited

U.S. PATENT DOCUMENTS

| | | |
|---|---|---|
| 5,682,884 A | 11/1997 | Hill et al. |
| 5,708,247 A | 1/1998 | McAleer et al. |

(Continued)

FOREIGN PATENT DOCUMENTS

| | | |
|---|---|---|
| CN | 104730253 B | 4/2017 |
| CN | 111024954 A | 4/2020 |

(Continued)

OTHER PUBLICATIONS

U.S. Appl. No. 17/566,828, Non-Final Office Action, dated Apr. 14, 2022, 14 pages.

(Continued)

*Primary Examiner* — Dennis White
(74) *Attorney, Agent, or Firm* — Kilpatrick Townsend & Stockton LLP

(57) ABSTRACT

Methods and techniques are described for analyzing test fluids to determine presence, absence, or concentration of analytes in the test fluids. The methods may correspond to diagnostic testing, such as quickly (within 5 minutes) identifying whether or not an individual may have a particular disease or condition, such as infection by SARS-CoV-2 or a SARS-CoV-2 variant or vaccine-induced immunity or natural immunity to infection by SARS-CoV-2 or a SARS-CoV-2 variant, or whether an individual would benefit from a vaccine booster. The test results can be used for a variety of applications including facilitating or controlling access at events, venues, or transportation systems, or generating exposure notifications.

22 Claims, 39 Drawing Sheets

Related U.S. Application Data filed on Aug. 13, 2021, provisional application No. 63/203,009, filed on Jul. 3, 2021, provisional application No. 63/202,828, filed on Jun. 25, 2021, provisional application No. 63/202,439, filed on Jun. 11, 2021, provisional application No. 63/202,135, filed on May 28, 2021, provisional application No. 63/201,982, filed on May 21, 2021.

(51) Int. Cl.
　　*G01N 33/569*　　(2006.01)
　　*G01N 33/68*　　(2006.01)
　　*G01N 33/543*　　(2006.01)
　　*G01N 33/553*　　(2006.01)

(52) U.S. Cl.
　　CPC ... *G01N 33/56983* (2013.01); *G01N 33/6893* (2013.01); *G01N 33/54306* (2013.01); *G01N 33/553* (2013.01)

(56) References Cited

U.S. PATENT DOCUMENTS

| | | |
|---|---|---|
| 7,144,486 B1 | 12/2006 | Fritsch et al. |
| 7,316,766 B2 | 1/2008 | Chen et al. |
| 7,820,108 B2 | 10/2010 | Lampotang et al. |
| 7,829,275 B2 | 11/2010 | Franzen et al. |
| 8,062,491 B1 | 11/2011 | Gau |
| 8,309,345 B2 | 11/2012 | Nishio et al. |
| 8,375,768 B2 | 2/2013 | Zeng et al. |
| 8,608,920 B2 | 12/2013 | Huang et al. |
| 8,737,971 B2 | 5/2014 | van Rooyen et al. |
| 8,758,576 B2 | 6/2014 | Escoffier et al. |
| 9,257,038 B2 | 2/2016 | Weintraub et al. |
| 9,366,645 B2 | 6/2016 | Ren et al. |
| 9,445,749 B2 | 9/2016 | Erickson et al. |
| 9,686,395 B2 | 6/2017 | Erickson et al. |
| 9,746,468 B2 | 8/2017 | Wang et al. |
| 9,787,815 B2 | 10/2017 | Erickson et al. |
| 9,808,798 B2 | 11/2017 | Ismagilov et al. |
| 10,012,645 B2 | 7/2018 | Kaushik et al. |
| 10,572,627 B2 | 2/2020 | Mayer et al. |
| 11,035,817 B1 | 6/2021 | Eissa et al. |
| 11,112,412 B1 | 9/2021 | Wang |
| 2004/0011650 A1 | 1/2004 | Zenhausern et al. |
| 2008/0202927 A1 | 8/2008 | Kayyem et al. |
| 2011/0139636 A1 | 6/2011 | Lai et al. |
| 2011/0210017 A1 | 9/2011 | Lai et al. |
| 2012/0012472 A1* | 1/2012 | Ahrens ............ G01N 33/54353 204/290.01 |
| 2013/0059293 A1 | 3/2013 | Menon et al. |
| 2014/0001047 A1 | 1/2014 | Kahn et al. |
| 2014/0014536 A1 | 1/2014 | Weiss et al. |
| 2014/0094383 A1 | 4/2014 | Lee et al. |
| 2014/0294675 A1 | 10/2014 | Melker et al. |
| 2015/0231633 A1 | 8/2015 | Dubin et al. |
| 2016/0041146 A1 | 2/2016 | McIntire et al. |
| 2016/0363550 A1 | 12/2016 | Koo et al. |
| 2018/0105611 A1 | 4/2018 | Lee et al. |
| 2018/0136190 A1 | 5/2018 | Sumathipala et al. |
| 2018/0188244 A1 | 7/2018 | Das et al. |
| 2019/0170738 A1 | 6/2019 | Ren et al. |
| 2019/0376926 A1 | 12/2019 | Tarasov |
| 2020/0240983 A1 | 7/2020 | Wang et al. |
| 2020/0261907 A1 | 8/2020 | Xie et al. |
| 2020/0300844 A1 | 9/2020 | Pretorius et al. |
| 2020/0323474 A1 | 10/2020 | McIntosh |
| 2020/0333286 A1 | 10/2020 | Leon et al. |
| 2021/0003528 A1 | 1/2021 | Esquivel-Upshaw et al. |
| 2021/0055259 A1 | 2/2021 | Lin |
| 2021/0093248 A1 | 4/2021 | Euliano et al. |
| 2021/0231673 A1 | 7/2021 | Walt et al. |
| 2021/0255172 A1 | 8/2021 | Beskok et al. |

FOREIGN PATENT DOCUMENTS

| | | |
|---|---|---|
| CN | 111537746 A | 8/2020 |
| EP | 2986987 B1 | 8/2018 |
| EP | 3855186 A2 | 7/2021 |
| IN | 202021016563 A | 6/2020 |
| WO | 1996/28538 A1 | 9/1996 |
| WO | 2008/150788 A1 | 12/2008 |
| WO | 2017/031518 A1 | 3/2017 |
| WO | 2018/031497 A1 | 2/2018 |
| WO | 2018/223090 A1 | 12/2018 |
| WO | 2019/005473 A1 | 1/2019 |
| WO | 2019/134741 A1 | 7/2019 |
| WO | 2020/097138 A1 | 5/2020 |
| WO | 2020/186118 A1 | 9/2020 |
| WO | 2021/046278 A1 | 3/2021 |
| WO | 2021/142121 A1 | 7/2021 |
| WO | 2021/207209 A2 | 10/2021 |
| WO | 2021/211332 A1 | 10/2021 |

OTHER PUBLICATIONS

Bell et al., "Clinical Research in the Elderly: Ethical and Methodological Considerations. Drug Intelligence and Clinical Pharmacy", Drug Intelligence and Clinical Pharmacy, vol. 21, Dec. 1987, pp. 1002-1007.

Carey et al., "Fast Cerebrospinal Fluid Detection Using Inexpensive Modular Packaging with Disposable Testing Strips", Journal of The Electrochemical Society, vol. 166, No. 8, May 2019, pp. B708-B712.

Chiang et al., "Development and Validation of a Quantitative, Non-Invasive, Highly Sensitive and Specific, Electrochemical Assay for Anti-SARS-CoV-2 IgG Antibodies in Saliva", PloS One, vol. 16, No. 7, Jul. 1, 2021, pp. 1-16.

Koyoma et al., "Variant Analysis of Sars-Cov-2 Genomes", Bulletin of the World Health Organisation, vol. 98, No. 7, Jun. 2, 2020, pp. 495-504.

Yang et al., "Zika Virus Detection Using Antibody-Immobilized Disposable Cover Glass and Algan/Gan High Electron Mobility Transistors", Applied Physics Letters, vol. 113, No. 3, Jul. 2018, 7 pages.

U.S. Appl. No. 17/566,828, filed Dec. 31, 2021, Unpublished.

PCT International Search Report and Written Opinion, PCT Patent Application No. PCT/US2022/030393, dated Aug. 24, 2022, 14 pages.

Brazaca et al., "Biosensing Strategies for the Electrochemical Detection of Viruses and Viral Diseases—A Review", Analytica Chimica Acta, vol. 1159, Mar. 12, 2021, 30 pages.

* cited by examiner

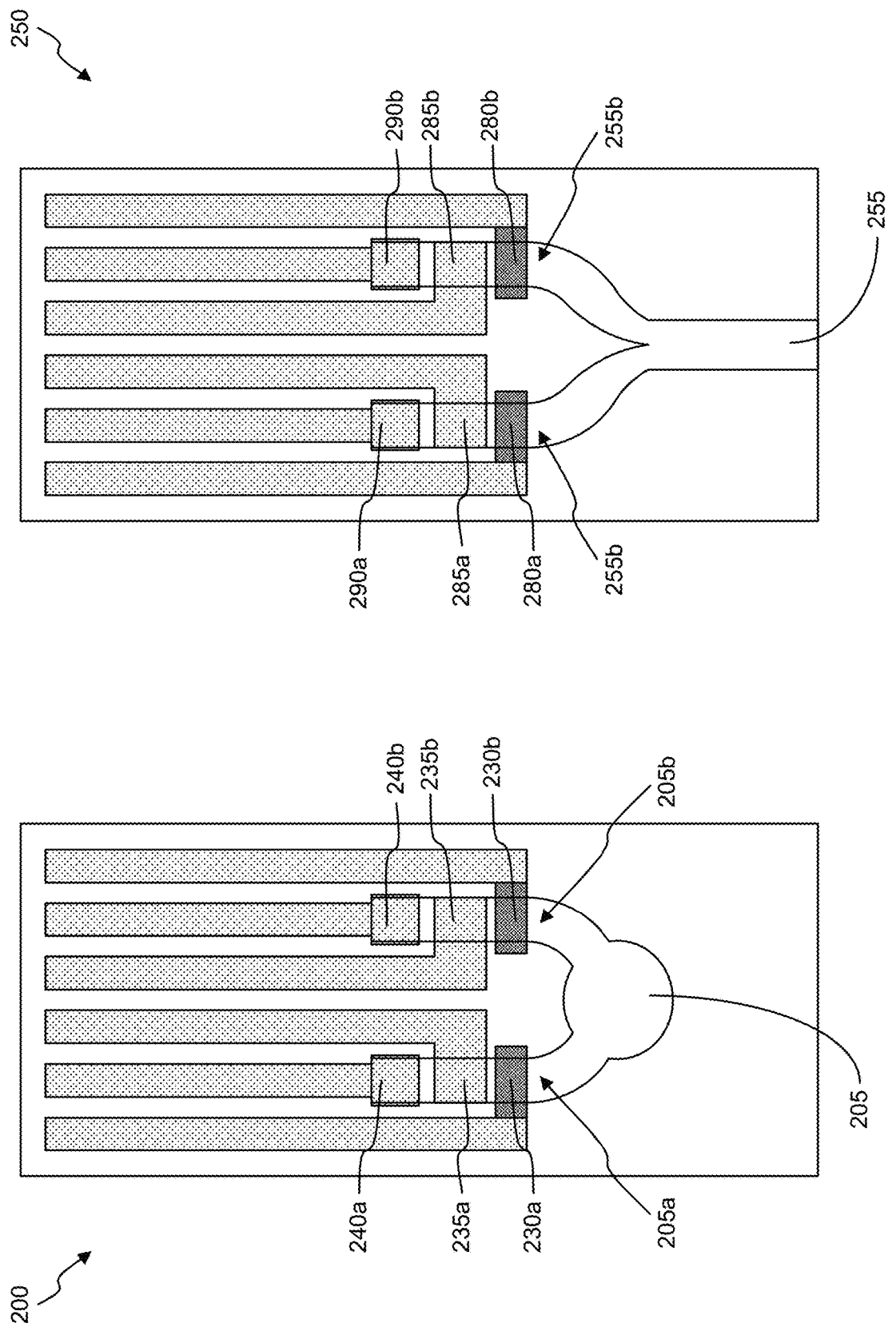

METHODS OF OBTAINING AND USING ELECTROCHEMICAL DIAGNOSTIC RESULTS

CROSS REFERENCE TO RELATED APPLICATIONS

This application claims the benefit of and priority to U.S. Provisional Application No. 63/201,982, filed on May 21, 2021, U.S. Provisional Application No. 63/202,135, filed on May 28, 2021, U.S. Provisional Application No. 63/202,439, filed on Jun. 11, 2021, U.S. Provisional Application No. 63/202,828, filed on Jun. 25, 2021, U.S. Provisional Application No. 63/203,009, filed on Jul. 3, 2021, U.S. Provisional Application No. 63/232,720, filed on Aug. 13, 2021, and U.S. Provisional Application No. 63/235,433, filed on Aug. 20, 2021, which are hereby incorporated by reference in their entireties.

TECHNICAL FIELD

This invention is in the field of diagnostic testing. This invention relates generally to electrochemical diagnostic test systems and components and techniques for rapidly identifying the presence of diagnostic analytes in body fluid samples.

BACKGROUND

Present and future containment of pathogen outbreaks such as COVID-19 are dependent on testing and retesting on very wide-scales. In a global pandemic this translates to a need for billions of rapid, accurate, and inexpensive tests performed at millions of locations. Further, data collection and aggregation should be nearly real-time to meet the needs of crisis managers. Current polymerase chain reaction (PCR) testing methods used for genomic analysis generally utilize sample collection followed by transport prior to PCR amplification and sequencing, which can delay determination of results. Rapid testing using antigen testing tends to be less specific, but can provide qualitative positive negative results in a much quicker time period (e.g., within 15 minutes). Improvements to viral testing methods are needed.

Both previous infection and vaccination have been shown to provide protection from COVID-19. However, waning immunity and viral variation may lead to a loss of protection over time. There are several predictive models of immune protection in terms of antibody levels over time developed in an attempt to identify immune correlates of protection to assist in determining susceptibility to infection post vaccination and the need to administer vaccine booster doses.

Current measurement of anti-COVID-19 antibody levels follow a serology approach and test blood samples. These tests detect antibodies (for example, IgM or IgG) to the SARS-CoV-2 virus and require a blood draw at a point of care visit, which is sent to a lab and results take up to 3 days to receive. However, serum antibody levels are not routinely ordered by physicians to monitor protection or when there is an exposure concern.

Overall, there is no device that can rapidly identify the immune correlate(s) of protection from SARS-CoV-2 infection or any method for predicting how changes in antibody levels will be reflected in clinical outcomes. Further, there is no simple, rapid method available to assess antibody levels post vaccination or to differentiate between immune responses after vaccination vs. the responses in convalescent individuals due to prior infection.

SUMMARY

In an aspect, methods are provided herein, such as methods for performing electrochemical assays or obtaining diagnostic test results using an electrochemical assay. In some examples, a method of this aspect comprises providing an electrochemical test strip device; receiving a test fluid at a fluid chamber of the electrochemical test strip device; coupling the electrochemical test strip device to an interface device; obtaining voltammograms using one or more potentiostats of the interface device; analyzing the voltammograms to identify a test result indicating a presence, absence, or quantitative measure of the target analyte in the test fluid; and outputting the test result in from 1 to 5 minutes of receiving the test fluid at the fluid chamber or coupling the electrochemical test strip device to the interface device. Optionally, the test fluid is associated with an individual and outputting the test result comprises transmitting the test result to an electronic device associated with the individual.

The methods described herein can be used with suitable electrochemical test strip devices. An example electrochemical test strip device comprises a first set of electrodes including a first reference electrode, a first working electrode, and a first counter electrode, the first working electrode functionalized with active capture molecules, such as active capture molecules that include one or more electroactive redox tags and/or active capture that molecules bind or are configured to bind a target analyte; a second set of electrodes including a second reference electrode, a second working electrode, and a second counter electrode, the second working electrode functionalized with null capture molecules, such as null capture molecules that include one or more electroactive redox tags and/or null capture molecules that bind or are configured to bind different analytes than the active capture molecules or do not bind or are not configured to bind the target analyte; a fluid chamber in fluid communication with the first set of electrodes and the second set of electrodes, the fluid chamber for receiving a test fluid with or without a test analyte and establishing contact between the test fluid and the first set of electrodes and between the test fluid and the second set of electrodes; a first set of electrode contacts in electrical communication with the first set of electrodes, the first set of electrode contacts including a first reference electrode contact, a first working electrode contact, and a first counter electrode contact; and a second set of electrode contacts in electrical communication with the second set of electrodes, the second set of electrode contacts including a second reference electrode contact, a second working electrode contact, and a second counter electrode contact. In examples, the first working electrode includes a first mixed self-assembled-monolayer (SAM) including a first linker component and a charged passivation component, the first linker component terminally binding the active capture molecules. In examples, the second working electrode includes a second mixed SAM including a second linker component and the charged passivation component, the second linker component terminally binding the null capture molecules. In examples, the first mixed SAM and the second mixed SAM are coated with or comprise an anti-fouling hydrogel comprising a plurality of different charged glycosaminoglycans.

In examples, the method comprises an assay for detection of anti-viral antibodies, such as by detecting a presence, absence or concentration of a target analyte. Optionally, the target analyte is viral infection-developed antibody or an antiviral vaccine-developed antibody. Optionally, the active capture molecules include a viral structural protein or portion thereof. Optionally, the viral infection-developed antibody comprises a coronavirus infection-developed antibody. Optionally, the antiviral vaccine-developed antibody comprises an anti-coronavirus vaccine-developed antibody. Optionally, the viral structural protein comprises a coronavirus structural protein.

In some examples, the viral infection-developed antibody comprises a SARS-CoV-2 infection-developed antibody or a SARS-CoV-2 variant infection-developed antibody. In some examples, the antiviral vaccine-developed antibody comprises an anti-SARS-CoV-2 vaccine-developed antibody or anti-SARS-CoV-2 variant vaccine-developed antibody. In some examples, the viral structural protein comprises a SARS-CoV-2 or SARS-CoV-2 variant spike protein, a SARS-CoV-2 or SARS-CoV-2 variant nucleocapsid protein, or a SARS-CoV-2 or SARS-CoV-2 variant envelope protein. Optionally, the viral structural protein comprises a SARS-CoV-2 spike protein, a SARS-CoV-2 nucleocapsid protein, or a SARS-CoV-2 envelope protein. Optionally, the null capture molecules include a SARS-CoV-2 variant spike protein or portion thereof, a SARS-CoV-2 variant nucleocapsid protein or portion thereof, or a SARS-CoV-2 variant envelope protein or portion thereof.

In some examples, the method comprises an antigen assay for a virus or a component thereof, a viral biomarker, or an inflammatory biomarker. In some examples, the target analyte is the virus or the component thereof, the viral biomarker, or the inflammatory biomarker. In some examples, the active capture molecules include a first antibody that binds the virus or the component thereof, the viral biomarker, or the inflammatory biomarker, or a receptor protein that binds the virus or the component thereof, the viral biomarker, the inflammatory biomarker. In some examples, the null capture molecules include a second antibody that does not bind the virus or the component thereof, the viral biomarker or the inflammatory biomarker. Optionally, the virus is a coronavirus. Optionally, the viral biomarker is a coronavirus spike protein or a coronavirus nucleocapsid protein. Optionally, the inflammatory biomarker is a coronavirus-induced inflammatory biomarker or host protein.

In some examples, the virus is SARS-CoV-2 or a variant of SARS-CoV-2. In some examples, the viral biomarker comprises a spike protein or a nucleocapsid protein of SARS-CoV-2 or a variant of SARS-CoV-2. In some examples, the inflammatory biomarker comprises a cytokine, a SARS-CoV-2-mediated inflammatory biomarker, or a SARS-CoV-2 variant-mediated inflammatory biomarker. Optionally, the first antibody comprises an anti-SARS-CoV-2 antibody, an anti-SARS-CoV-2 variant antibody, or an anti-cytokine antibody. Optionally, the receptor protein comprises an angiotensin-converting enzyme 2 (ACE-2) or portion thereof. In some examples, the test result indicates infection by a SARS-CoV-2 variant.

The electrochemical test strip devices and methods described herein are not so specific for use in detection of viruses and can be broadly applied to a variety of different systems. In some examples, the active capture molecules include a first antibody, first receptor protein, or a first aptamer that binds the target analyte and the null capture molecules include a second antibody, second receptor protein, or a second aptamer that does not bind the target analyte.

Without wishing to be bound by any theory, binding of the target analyte to the active capture molecules can modulates a proximity between the first working electrode and the one or more electroactive redox tags of the active capture molecules, such as relative to a proximity between the second working electrode and the one or more electroactive redox tags of the null capture molecules. An increase in hydrodynamic drag due to the binding of the target analyte may impact the ability of the proximity between the first working electrode and the one or more electroactive redox tags of the active capture molecules to be modulated by application of a potential to the first working electrode. In some examples, the modulation that occurs upon binding the target analyte to the active capture molecules can be observed as a modulation in current measured in a voltammogram using the first set of electrodes, such as in a potentiostatic measurement system.

Preparation of the working electrodes of the electrochemical test strip devices can include preparing mixed SAMs that are adapted to couple to the active capture molecules. For example, one or both the first linker component or the second linker component optionally comprises surface-bound alkyne terminated polyethylene glycol (PEG) molecules. Such alkyne functionalization may allow for reaction with azido functionalized capture molecules, using click chemistry. For example, the first linker component and active capture molecule may comprise an adduct or bioconjugate of an alkyne terminated polyethylene glycol (PEG) molecule and an azido modified active capture molecule, the azido modified active capture molecule comprising an azido moiety, the one or more electroactive redox tags, and one or more binding regions for the target analyte. Optionally, the alkyne terminated polyethylene glycol (PEG) molecule is immobilized on the surface of the first working electrode, and the alkyne terminated PEG molecule is coupled to the azido modified active capture molecule by a click chemistry reaction. In some examples, the azido modified active capture molecule comprises an antibody including the azido moiety at a glycosylated region on a crystallizable fragment (Fc) portion of the antibody and the one or more binding regions at an antigen-binding fragment (Fab) portion of the antibody. In another example, the second linker component and null capture molecule may comprise an adduct or bioconjugate of an alkyne terminated polyethylene glycol (PEG) molecule and an azido modified null capture molecule, the azido modified null capture molecule comprising an azido moiety, the one or more electroactive redox tags, and a binding moiety that does not bind the target analyte. In some examples, the alkyne terminated polyethylene glycol (PEG) molecule is immobilized on the surface of the second working electrode, and the alkyne terminated PEG molecule is coupled to the azido modified null capture molecule by a click chemistry reaction.

The working electrode may include components that can limit, minimize, or avoid fouling, such as due to the presence of non-specific proteins or substances in the test fluid. For example, the charged passivation component optionally comprises charged polyethylene glycol (PEG) molecules bound to a surface of the first working electrode, such as PEG molecules comprising one or more carboxylic acid groups or carboxylate groups. Optionally, the first mixed SAM comprises from about 10% to about 50% of the first linker component, such as from 10% to 15%, from 15% to 20%, from 20% to 25%, from 25% to 30%, from 30% to 35%, from 35% to 40%, from 40% to 45%, or from 45% to 50%. Optionally, the first mixed SAM comprises from about 50% to about 90% of the charged passivation component, such as from 50% to 55%, from 55% to 60%, from 60% to 65%, from 65% to 70%, from 70% to 75%, from 75% to 80%, from 80% to 85%, or from 85% to 90%. Optionally, the second mixed SAM comprises from about 10% to about 50% of the second linker component, such as from 10% to 15%, from 15% to 20%, from 20% to 25%, from 25% to 30%, from 30% to 35%, from 35% to 40%, from 40% to 45%, or from 45% to 50%. Optionally, the second mixed SAM comprises from about 50% to about 90% of the charged passivation component, such as from 50% to 55%, from 55% to 60%, from 60% to 65%, from 65% to 70%, from 70% to 75%, from 75% to 80%, from 80% to 85%, or from 85% to 90%. In some examples, a percent of a mixed SAM refers to a mole fraction or an area fraction.

A variety of different charged glycosaminoglycans are useful with the electrochemical test strip devices, and may be useful for limiting, minimizing, or preventing or avoiding fouling, such as due to the presence of non-specific proteins or substances in the test fluid. Useful charged glycosaminoglycans include, but are not limited to, lubricin, recombinant lubricin, hyaluronic acid, heparin, heparan sulfate, chondroitin sulfate, keratan sulfate, lumican, keratocan, mimecan, dermatan sulfates, glycosaminoglycans cross-linked with collagen, or any combination of these. Optionally, the plurality of different charged glycosaminoglycans prevent electrode biofouling by repelling non-specific proteins in the test fluid.

A variety of different electroactive redox tags are useful with the electrochemical test strip devices. For example, useful electroactive redox tags include, but are not limited to, methylene blue, ferrocene or a ferrocene derivative, $[Ru(NH_3)_6]^{3+/2+}$, an organic metal chelate $[M(L_3)]^{3+/2+}$ where M is Fe, Co, Os or Ru, and L is a heterocyclic nitrogenous bidentate ligand including 2,2'-bipyridine (bipy) or 1,10-phenantroline (phen), a metalloporphyrin, an oxoosmium (VI) complex, a metalloorganic, a quinone, a hydroquinone, anthraquinone, an anthracycline, daunomycin, doxorubicin, a viologen, a phenothiazine, thionine, malachite green, 2,2'-bipyridine-4,4'-dicarboxylic acid, 1,3-di-aza-2-oxophenothiazine, a tricyclic cytosine analog, a quinoxaline derivatives, echinomycin, or any combination of these. Optionally, the one or more electroactive redox tags of the active capture molecules are the same as the one or more electroactive redox tags of the null capture molecules.

In some examples, the electrochemical test strip devices include those where the active capture molecule comprises one or more antibodies, one or more monoclonal antibodies, one or more functional antibody fragments, one or more aptamers, one or more high affinity binding peptides, one or more lectins, one or more receptor proteins, or one or more enzymes. Optionally, the target analyte may be a protein, a peptide, an amino acid, an oligonucleotide, a toxin, a small molecule, a sugar, a hormone, a metabolite, a biomarker, an antibody, or a combination of these. Optionally, the target analyte is a virus, a viral component, a viral biomarker, a bacterial cell, a bacterial cell component, a bacterial biomarker, a fungal cell, a fungal cell component, a fungal biomarker, a parasite, a parasite component, a parasite biomarker, a single-celled organism, a single-celled organism component, or a single-celled organism biomarker. Optionally, the test fluid is or contains saliva, nasopharyngeal fluid or mucus, pulmonary fluid, sputum, blood, plasma, serum, whole blood, tears, urine, fecal material, sweat, emesis, cervical cells or mucus, vaginal fluid or mucus, heart cells, breast milk, breast tissue cells, tumor cells, cerebrospinal fluid, skin cells, or pleural effusion.

Various different materials may be used for components of the electrochemical test strip devices. For example, one or more of the first working electrode, the first counter electrode, the second working electrode, or the second counter electrode may comprises gold, platinum, or carbon. In some examples, one or both of the first reference electrode or the second reference electrode comprises silver or silver chloride. Advantageously, the first set of electrode contacts and the second set of electrode contacts may be configured for or useful for interfacing with an external reader, such as comprising an interface device.

The methods described herein optionally include performing potentiostatic measurements on electrochemical test strip devices, such as by or using a suitable interface device. In examples, an interface device comprises a set of electrode contacts for coupling to one or more electrode contacts of an electrochemical test strip device; one or more potentiostats in electrical communication with the set of electrode contacts; and a waveform generator in electrical or control communication with the one or more potentiostats for generating a potential waveform. Optionally, an interface device may further comprise a processor in data or control communication with the one or more potentiostats and the waveform generator, such as a processor that is programmed with instructions or in data communication with a non-transitory computer-readable storage medium storing processor executable instructions. In some examples, the instructions, when executed by the processor, cause the processor to perform operations. Example operations optionally include those corresponding to methods described herein. In some examples, the operations may include obtaining voltammograms and outputting test results based on the voltammograms.

Optionally, the interface devices can be used to perform differential measurements, using the set of electrodes. Optionally, the set of electrodes may be coupled to a first set of electrodes and second set of electrodes of an electrochemical test strip device. In some examples, the voltammograms include a test voltammogram obtained using the set of electrodes or a first portion thereof and a reference voltammogram obtained using the set of electrodes or a second portion thereof. Optionally, operations performed by the processor may further include determining a corrected voltammogram based on a difference between the test voltammogram and the reference voltammogram. In some examples, the corrected voltammogram provides a qualitative measure of a presence or absence of the target analyte in the test fluid. Optionally, the corrected voltammogram provides a quantitative measure of an amount or concentration of the target analyte in the test fluid.

In some examples, an interface device may further comprise a button or other input device in data communication with the processor for causing initiation of obtaining the voltammograms using the one or more potentiostats, the first set of electrodes, and the second set of electrodes. The interface device may comprise an input/output device in data communication with the processor, such as a wired or wireless controller, which can pass instructions to initiate obtaining voltammograms. Optionally, the operations include receiving input corresponding to a directive to initiate obtaining the voltammograms.

The interface device may be configured to output a test result, such as in the form of a visible or audible signal or via data communication with an electronic device. In some examples, the operations include outputting a test result corresponding to a presence, absence, or quantitative measure of the target analyte in the test fluid based on the voltammograms within 1-5 minutes after receiving the input. Optionally, the interface device may further one or more light emitting diodes or other output devices in data communication with the processor for indicating a presence, absence, or quantitative measure of the target analyte in the test fluid based on the voltammograms. Optionally, the operations include outputting a test result corresponding to a presence, absence, or quantitative measure of the target analyte in the test fluid based on the voltammograms.

Advantageously, the methods described herein can provide accurate determination of the presence of the target analyte in the test fluid. In some examples, the test result has a sensitivity or detection limit for the target analyte of from about 0.1 $TCID_{50}$/ml to about $10^5$ $TCID_{50}$/ml, such as from 0.1 $TCID_{50}$/ml to 1 $TCID_{50}$/ml, from 1 $TCID_{50}$/ml to 10 $TCID_{50}$/ml, from 10 $TCID_{50}$/ml to 100 $TCID_{50}$/ml from 100 $TCID_{50}$/ml to $10^4$ $TCID_{50}$/ml, or from $10^4$ $TCID_{50}$/ml to $10^5$ $TCID_{50}$/ml. In some examples, the test result has a sensitivity or detection limit for the target analyte of from about 1 fg/ml to about 10 ng/ml, such as from 1 fg/ml to 10 fg/ml, from 10 fg/ml to 100 fg/ml, from 100 fg/ml to 1 pg/ml, from 1 pg/ml to 10 pg/ml, from 10 pg/ml to 100 pg/ml, from 100 pg/ml to 1 ng/ml, or from 1 ng/ml to 10 ng/ml. Optionally, the test result has a sensitivity or detection limit for the target analyte of from 0.1 $TCID_{50}$/ml to about 10 $TCID_{50}$/ml or a sensitivity or detection limit for the target analyte of from about 1 fg/ml to about 1 pg/ml.

In some examples, outputting the test result comprises one or more of: storing the test result to a non-transitory computer readable storage device; transmitting the test result to a remote computing device; or outputting an audible or visual indicator providing the test result. In this way, the test results can be stored for later use or retrieved at a remote location. For example, the test results can be sent to an electronic health record or de-identified and stored to a publicly accessible ledger (e.g., a blockchain) with a unique code or key assigned to an individual that can be used to associate the test result with the unique code or key.

In some examples, the test results determined at one location can be retrieved at a second, remote location. In this way, the test results can be used to facilitate access, such as to an event, venue, transportation system, or the like. In the case of the test result identifying vaccine-induced immunity or infection-induced immunity to an infectious disease (e.g., COVID-19), the test result can be used to prove status to allow access to an event, venue, transportation system where immunity is a prerequisite for entry. For example, the test result may correspond to or comprise a vaccine status, or a prior infection status. Optionally, methods of this aspect may comprise or further comprise analyzing the test result to determine an access status for an individual associated with the test sample; and generating an indication of the access status. In some cases, generating the indication of the access status may comprise one or more of storing the access status to a non-transitory computer readable storage device; outputting an audible or visual indicator providing the access status; or transmitting the access status to an access control device (e.g., a locked door, or a turnstile) or associated control system. Optionally, methods of this aspect may further comprise electronically controlling an access control device based on the access status.

Methods of this aspect may include associating the test result with an individual, an identifier for the individual, a biometric for the individual, or a protected record for the individual. For example, the test result may be then retrieved using the identifier, the biometric, or the protected record. In some examples, the protected record is an electronic health record, a blockchain record. Methods of this aspect may include associating the test result with a test facility, test administrator, or location. Such information may be useful for determining various characteristics of performing the test or provide information useful for medical personnel or public health personnel, for example. Methods of this aspect may include associating the test result with an identifier for a specific electrochemical test strip device, an identifier for a specific interface device, an identifier for a batch of electrochemical test strip devices, or an identifier for a batch of interface devices. Again, such information may be useful for determining various characteristics about the instrumentation used to obtain the test result that may be of interest at a later time, such as to medical personnel or public health personnel. Methods of this aspect may include associating the test result with a time, which may be useful for a variety of situations, including those described above. In some examples, the electrochemical test strip device includes a test strip identifier (e.g., a barcode) and the method may further comprise associating the test result with the test strip identifier. Optionally, the test strip identifier may comprise a braille code or characters, such as to facilitate communicating information to blind or low-vision individuals. A braille code or characters may also provide a grip or friction enhancing surface.

For use of test results as infection or vaccination indicators, it may be desirable to share the test results with medical personnel or databases or public health personnel or databases. In some examples, outputting the test result may comprises transmitting the test result to a medical facility or a public health agency, for example. In some examples, outputting the test result comprises transmitting the test result to an exposure notification system.

In the case of a test result indicating a positive status (e.g., infection by a virus), it may be desirable to provide the testee with information about the infection or next steps to limit infection or further spread of the infection to others. Optionally, outputting the test result comprises outputting isolation protocols, facilitating contact to a medical professional or medical facility, or contacting emergency services.

Methods described herein may include or utilize artificial intelligence or machine learning aspects. In some examples, analyzing the voltammograms includes inputting the voltammograms into a trained machine-learning model, such as a trained machine-learning model comprising a set of parameters that were learned using other voltammograms, the other voltammograms associated with detection of known quantities of the target analyte, and one or more functions configured to transform the voltammograms, using the set of parameters, into the test result indicating the presence, absence, or quantitative measure of the target analyte in the test fluid.

Methods described herein may include or be useful for detecting compliance markers, such as for use in tracking compliance with a treatment regimen. Optionally, the target analyte comprises a compliance marker or a compliance marker metabolite. In some examples, the compliance marker or a compliance marker conjugate is included in a pharmaceutical formulation, such as a pharmaceutical formulation administered to an individual. In examples, the test fluid is received at a predetermined time following scheduled administration of the pharmaceutical formulation to the individual. Optionally, the test fluid comprises saliva, blood, or urine. In some examples, the compliance marker comprises a generally recognized as safe (GRAS) composition or wherein the compliance marker conjugate comprises a therapeutic-GRAS conjugate or a non-therapeutic-GRAS conjugate. Optionally, the compliance marker comprises probenecid-propylene glycol ester. Optionally, the compliance marker metabolite comprises propylene glycol. In some examples, the method may further comprise analyzing the test result to determine compliance with or adherence to a treatment regimen. Optionally, the method may further comprise generating a time-stamped notification or report indicating the test result and determined compliance with or adherence to the treatment regimen. In some cases, machine learning may be used for determining compliance with or adherence to the treatment regimen. Optionally, analyzing the test result includes inputting the test result into a trained machine-learning model, such as a trained machine-learning model comprising a set of parameters that were learned using other test results, the other test results associated with detection of the compliance marker or compliance marker metabolite in body fluid samples from other individuals and characteristics for the other individuals; and one or more functions configured to transform test result, using the set of parameters, into an indication of compliance with or adherence to the treatment regimen.

Methods of this aspect may include performing differential potentiostatic measurements, such as by obtaining voltammograms including a test voltammogram obtained using the first set of electrodes of the electrochemical test strip device and a reference voltammogram obtained using the second set of electrodes of the electrochemical test strip device. In some examples, the method may further comprise determining a corrected voltammogram based on a difference between the test voltammogram and the reference voltammogram. Optionally, the corrected voltammogram provides a qualitative measure of a presence or absence of the target analyte in the test fluid or the corrected voltammogram provides a quantitative measure of an amount or concentration of the target analyte in the test fluid. In some examples, outputting the test result comprises outputting a result corresponding to a presence, absence, or quantitative measure of the target analyte in the test fluid based on the voltammograms.

Advantageously, methods described herein can provide accurate determination of the presence of the target analyte in the test fluid. In some examples, the test result has a sensitivity or detection limit for the target analyte of from about 0.1 $TCID_{50}$/ml to about $10^5$ $TCID_{50}$/ml, such as from 0.1 $TCID_{50}$/ml to 1 $TCID_{50}$/ml, from 1 $TCID_{50}$/ml to 10 $TCID_{50}$/ml, from 10 $TCID_{50}$/ml to 100 $TCID_{50}$/ml from 100 $TCID_{50}$/ml to $10^4$ $TCID_{50}$/ml, or from $10^4$ $TCID_{50}$/ml to $10^5$ $TCID_{50}$/ml. In some examples, the test result has a sensitivity or detection limit for the target analyte of from about 1 fg/ml to about 10 ng/ml, such as from 1 fg/ml to 10 fg/ml, from 10 fg/ml to 100 fg/ml, from 100 fg/ml to 1 pg/ml, from 1 pg/ml to 10 pg/ml, from 10 pg/ml to 100 pg/ml, from 100 pg/ml to 1 ng/ml, or from 1 ng/ml to 10 ng/ml. Optionally, the test result has a sensitivity or detection limit for the target analyte of from 0.1 $TCID_{50}$/ml to about 10 $TCID_{50}$/ml or a sensitivity or detection limit for the target analyte of from about 1 fg/ml to about 1 pg/ml.

In some cases, methods described herein are useful for determining an immunity status of an individual, such as immunity to a particular virus or a variant thereof, or identifying that an individual is in need of a booster vaccination. For example, a method comprises providing an electrochemical test strip device, such as an electrochemical test strip device comprising a first set of electrodes including a first reference electrode, a first working electrode, and a first counter electrode, the first working electrode functionalized with first capture molecules, such as first capture molecules that include one or more electroactive redox tags and a first binding agent for a first viral antibody, for example a first viral antibody that is a viral antibody produced due to vaccine-induced humoral response; a second set of electrodes including a second reference electrode, a second working electrode, and a second counter electrode, the second working electrode functionalized with second capture molecules, such as second capture molecules that include one or more electroactive redox tags and a second binding agent for a second viral antibody, for example a second viral antibody that is a viral antibody produced due to infection-induced humoral response; a fluid chamber in fluid communication with the first set of electrodes and the second set of electrodes, the fluid chamber for receiving a test fluid containing a test analyte and establishing contact between the test fluid and the first set of electrodes and between the test fluid and the second set of electrodes; a first set of electrode contacts in electrical communication with the first set of electrodes, the first set of electrode contacts including a first reference electrode contact, a first working electrode contact, and a first counter electrode contact; and a second set of electrode contacts in electrical communication with the second set of electrodes, the second set of electrode contacts including a second reference electrode contact, a second working electrode contact, and a second counter electrode contact; for example, the first working electrode that includes a first mixed self-assembled-monolayer (SAM) including a first linker component and a charged passivation component, the first linker component terminally binding the first capture molecules and a second working electrode that includes a second mixed SAM including a second linker component and the charged passivation component, the second linker component terminally binding the second capture molecules; and where the first mixed SAM and the second mixed SAM are coated with an anti-fouling hydrogel comprising a plurality of different charged glycosaminoglycans. The method further comprises receiving the test fluid at the fluid chamber; coupling the electrochemical test strip device to an interface device, such as an interface device that comprises a third set of electrode contacts for coupling to the first set of electrode contacts and the second set of electrode contacts of the electrochemical test strip device; one or more potentiostats in electrical communication with the third set of electrode contacts; and a waveform generator in electrical or control communication with the one or more potentiostats for generating a potential waveform. The method further comprises obtaining voltammograms using the one or more potentiostats, the waveform generator, the first set of electrodes, and/or the second set of electrodes; analyzing the voltammograms to identify a test result indicating a qualitative or quantitative measure of immunity provided by the first viral antibody or the second viral antibody; and outputting the test result in from 1 to 5 minutes of receiving the test fluid at the fluid chamber or coupling the electrochemical test strip device to the interface device.

In specific examples, the first viral antibody comprises an anti-SARS-CoV-2 or anti-SARS-CoV-2 variant antibody produced due to vaccine-induced humoral response and the second viral antibody comprises an anti-SARS-CoV-2 or anti-SARS-CoV-2 variant antibody produced due to infection-induced humoral response. Optionally, the first binding agent comprises a first SARS-CoV-2 or SARS-CoV-2 variant structural protein or portion thereof and the second binding agent comprises a second SARS-CoV-2 or SARS-CoV-2 variant structural protein or portion thereof. Optionally, the first binding agent comprises a SARS-CoV-2 or SARS-CoV-2 variant spike protein or portion thereof and the second binding agent comprises a SARS-CoV-2 or SARS-CoV-2 variant nucleocapsid protein or portion thereof, a SARS-CoV-2 or SARS-CoV-2 variant envelope protein or portion thereof, or a SARS-CoV-2 or SARS-CoV-2 variant spike protein or portion thereof. Optionally, the first target binding agent comprises a SARS-CoV-2 spike protein S1 subunit or portion thereof. In some examples, the test result is indicative of vaccination against SARS-CoV-2 or a SARS-CoV-2 variant, previous infection with SARS-CoV-2 or SARS-a CoV-2 variant, or susceptibility or naivety to infection by SARS-CoV-2 or a SARS-CoV-2 variant.

Optionally, the test result comprises a notification providing a vaccine booster recommendation. In some cases, where a vaccine booster recommendation, artificial intelligence or machine learning may be useful for determining such a recommendation. For example, analyzing the voltammograms to identify the test result may comprise inputting the voltammograms into a trained machine-learning model, the trained machine-learning model comprising a set of parameters that were learned using other voltammograms, the other voltammograms associated with detection of known quantities of the first viral antibody or the second viral antibody; and one or more functions configured to transform the voltammograms, using the set of parameters, into the vaccine booster recommendation.

Methods described herein may be useful for determining an outbreak of an infectious disease, such as in a particular geographic area. In some examples, a method comprises obtaining a plurality of test results, such as test results each corresponding to individual test results of an antigen assay for a target analyte obtained using electrochemical test strips, as described herein, such as where the plurality of test results include a location for each test result, a timestamp for each test result, or a device identifier for each test result (e.g., a device identifier associated with an individual corresponding to a test result, such as a testee). The method optionally, further comprises analyzing the plurality of test results to determine an above baseline incidence of the target analyte in a particular geographic area or over a particular time period. Optionally, obtaining the plurality of test results includes aggregating test results from a plurality of test locations. In some cases, analyzing the one or more locations and one or more time stamps and the plurality of test results may be useful for determining a contact or proximity between a plurality of individuals. In such cases, the method may further include triggering an exposure notification for devices of at least one of the plurality of individuals based on the contact or proximity.

Artificial intelligence or machine learning may be useful for identifying expected incidence of or spread of an infectious disease using the test results. In some examples, analyzing the plurality of test results includes inputting the plurality of test results into a trained machine-learning model, such as a trained machine-learning model comprising: a set of parameters that were learned using other test results, the other test results associated with individuals verified to exhibit or not exhibit the target analyte in a body fluid or a tissue sample; and one or more functions configured to transform the test results, using the set of parameters, into a projection of incidence of individuals exhibiting the target analyte in body fluid or tissue samples. Optionally, the one or more functions are further configured to provide a graphical output of the projected incidence, such as in the form of a 2-dimensional or 3-dimensional representation (e.g., on a map or as a heatmap). Optionally, the one or more functions are further configured to trigger a notification indicating a statistical measure of an exposure to individuals exhibiting the target analyte in body fluid or tissue samples.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIG. 2A shows a top-view schematic illustration of an example dual-chamber electrochemical test strip device with a top fill configuration. FIG. 2B shows a top-view schematic illustration of an example dual-chamber electrochemical test strip device with an edge fill configuration.

Figure 1A:
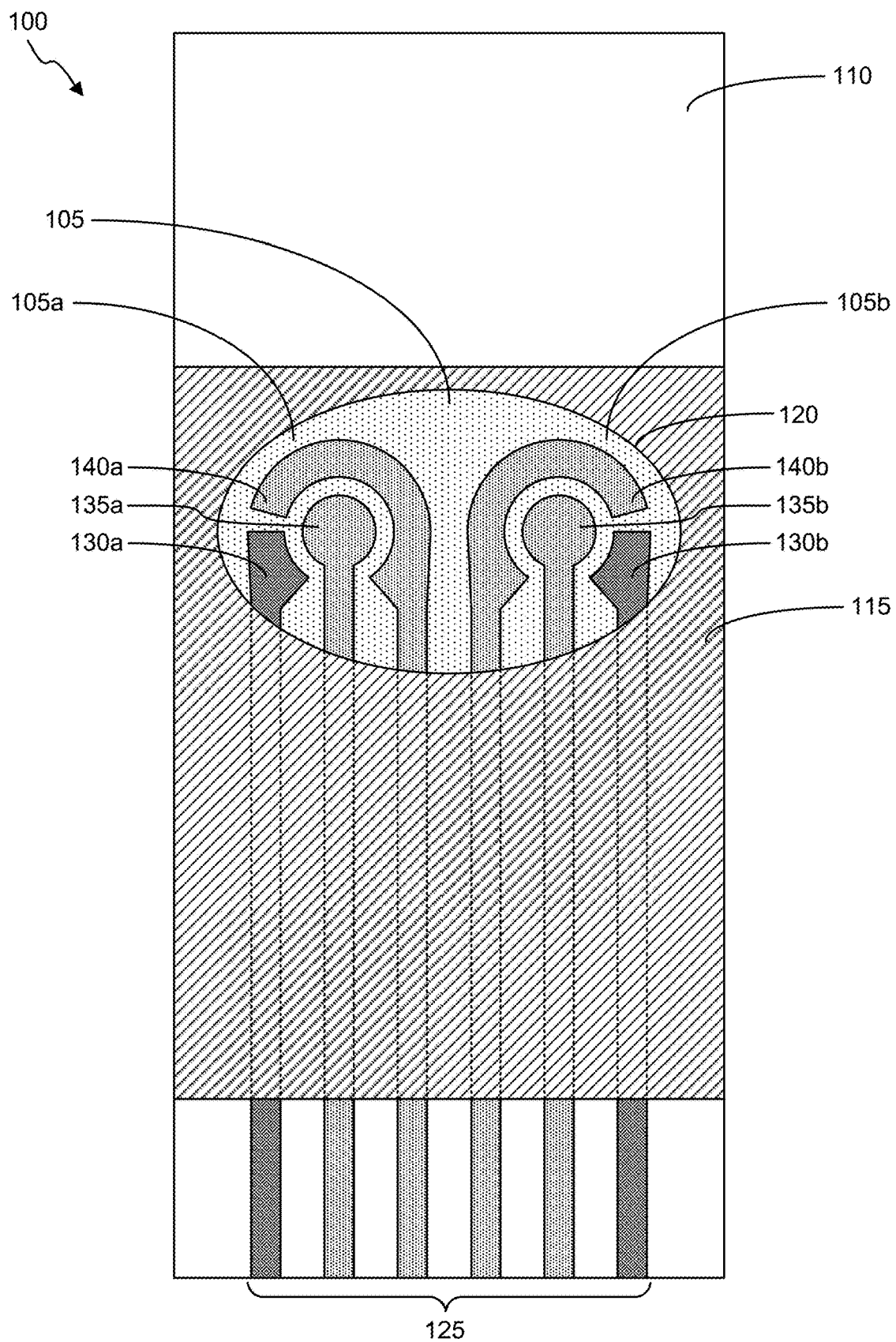
FIG. 1A and FIG. 1B provide schematic illustrations of an example electrochemical test strip device.

In examples, the electroactive redox tags can be part of, bonded to, or otherwise attached to the capture molecules bound to one or more electrodes of an electrochemical test strip. When the capture molecules bind the target analyte, a distance between the electroactive redox tag and the electrode can be modulated from the distance in the unbound state, providing a measurable electrical feedback or signal indicating binding of the capture molecules to the target analyte. The measurable signal can allow for very sensitive detection of extremely small concentrations of target analytes, such as on the femtogram/ml scale. In the case of infectious viral particles, detections as small as 0.1 $TCID_{50}$/ml are achievable.

The presently disclosed devices, systems, kits, methods, and techniques employ electrodes functionalized with capture molecules, which can be prepared as self-assembled-monolayers (SAMs) or mixed SAMs. As referred to herein, a mixed SAM is a SAM including multiple monolayer components, as opposed to a SAM including just a single component making up the entirety of the monolayer. The capture molecules can be attached to the electrode by way of a linker component that terminally binds or is terminally bonded to the capture molecules. As a non-limiting example, the linker component may comprise a thiolated polyethylene glycol (PEG) group, which can form a sulfur-metal bond to metal surfaces (e.g., gold, silver, copper, platinum, etc.) to generate a self-assembled monolayer.

Partial coverage of the electrode surface with the capture molecules may be sufficient and so passivation components that do not include the capture molecules can be included in the SAM. For example, a mixed SAM may include a linker component (e.g., binding or bonded to the capture molecule) and a passivation component, which may optionally be charged. In some examples, the passivation component may be a thiolated PEG group that is not bound to the active capture molecules. Optionally, the passivation component may include one or more carboxylic acid groups, which can be deprotonated to form a charged passivation component. In some examples, the surface of the electrode can be functionalized with a mixed SAM by exposing the electrode to a solution containing a mixture of different thiolated PEG molecules, such as including a first PEG molecule that comprises one or more carboxylic acid groups (e.g., as a charged passivation component) and a second PEG molecule including different functionality (e.g., to bond to or bind the capture molecule).

In some examples, click chemistry can be used to couple or bond the capture molecule to a linker component. Click chemistry can be extremely specific and allow coupling of two different molecules in an adduct or bioconjugate configuration precisely with limited side reactions. In some examples, click chemistry can include bond-forming reactions involving azido functionalized molecules and alkyne functionalized molecules. In some examples, use of alkyne-terminated PEG molecules can be useful for coupling the capture molecules functionalized with azido groups to the electrode using click chemistry. Optionally, use of azido functionalized PEG molecules can be useful for coupling the capture molecules functionalized with alkyne groups to the electrode using click chemistry.

In the case of mixed SAMs, a first component of the SAM can include alkyne-terminated PEG-thiol molecules and a second component of the SAM can include PEG-thiol molecules that are not functionalized with alkyne groups, such as including non-functionalized PEG-thiol molecules or carboxylic acid-functionalized PEG-thiol molecules. In this way, only part of the SAM will include alkyne-terminated PEG-thiol molecules that can be linked to the capture molecules using click chemistry, as described above. Advantageously, such mixed-SAMs can be prepared efficiently using thiol surface linking by exposing an electrode surface to a mixture of alkyne-terminated PEG-thiol molecules and PEG-thiol molecules without alkyne termination. In some cases, a mixed-SAM can be prepared in time periods as short as from about 1 hour to about 5 hours, such as from 1 hour to 1.5 hours, from 1.5 hours to 2 hours, from 2 hours to 2.5 hours, from 2.5 hours to 3 hours, from 3 hours to 3.5 hours, from 3.5 hours to 4 hours, from 4 hours to 4.5 hours, or from 4.5 hours to 5 hours.

The surface-bound alkyne-terminated PEG thiol molecules can be subjected to reaction with azido-functionalized capture molecules to functionalize an electrode with the capture molecules (e.g., by click chemistry). Optionally, the reaction can proceed by exposing the mixed SAM including alkyne-terminated PEG-thiol molecules and azido-terminated PEG-thiol molecules to the azido-functionalized capture molecules, such as while heating and/or in the presence of a catalyst (e.g., a copper catalyst). In some examples, the reaction can functionalize the surface with capture molecules in time periods as short as from about 1 hour to about 5 hours, such as from 1 hour to 1.5 hours, from 1.5 hours to 2 hours, from 2 hours to 2.5 hours, from 2.5 hours to 3 hours, from 3 hours to 3.5 hours, from 3.5 hours to 4 hours, from 4 hours to 4.5 hours, or from 4.5 hours to 5 hours. Accordingly, the preparation of the mixed SAM and functionalization with capture molecules can be completed rapidly, such as in from about 2 hours to about 10 hours, for example, from 2 hours to 2.5 hours, from 2.5 hours to 3 hours, from 3 hours to 3.5 hours, from 3.5 hours to 4 hours, or from 4 hours to 4.5 hours, from 4.5 hours to 5 hours, from 5 hours to 5.5 hours, from 5.5 hours to 6 hours, from 6 hours to 6.5 hours, from 6.5 hours to 7 hours, from 7 hours to 7.5 hours, from 7.5 hours to 8 hours, from 8 hours to 8.5 hours, from 8.5 hours to 9 hours, from 9 to 9.5 hours, or from 9.5 hours to 10 hours. In some cases, preparation of the mixed SAM functionalization can be completed in less than 6 hours.

Although the electrochemical test strips can be very sensitive to target analytes, in some cases they can also be sensitive to other analytes, molecules, or components that can interact with the electrodes, the electroactive redox tags, or the capture molecules, which can cause both false positive and false negative detections. Such interference of detection of target analytes by non-target analytes or other test fluid components may be referred to herein as fouling or biofouling (e.g., in the case of interferents originating from biological materials or fluids which may be present in the test fluid). Advantageously, the presently disclosed devices, systems, kits, methods, and techniques can limit fouling or biofouling and provide sensitive specific detection of target analytes even when the test fluid includes other analytes, molecules, or components. As an example, an anti-fouling hydrogel may be coated over or with the mixed SAM, such as a hydrogel comprising one or more charged glycosaminoglycans. In some cases a plurality of different charged glycosaminoglycans can be used. Non-limiting examples of charged glycosaminoglycans include lubricin (e.g., recombinant lubricin), hyaluronic acid, heparin, heparan sulfate, chondroitin sulfate, keratan sulfate, lumican, keratocan, mimecan, dermatan sulfates, glycosaminoglycans crosslinked with collagen. By using a hydrogel including different charged glycosaminoglycans coated over or with a mixed SAM including a passivation component (e.g., a charged passivation component) and a linking component terminally binding a capture molecule, sensitive and specific detection of target analytes can be achieved. Sensitivity can be further improved by simultaneous use of a reference electrode system constructed essentially similarly, but including capture molecules that do not bind the target analyte (e.g., null capture molecules), instead of capture molecules that do bind the target analyte (e.g., active capture molecules).

Electrochemical Test Strip Devices

Figure 1B:
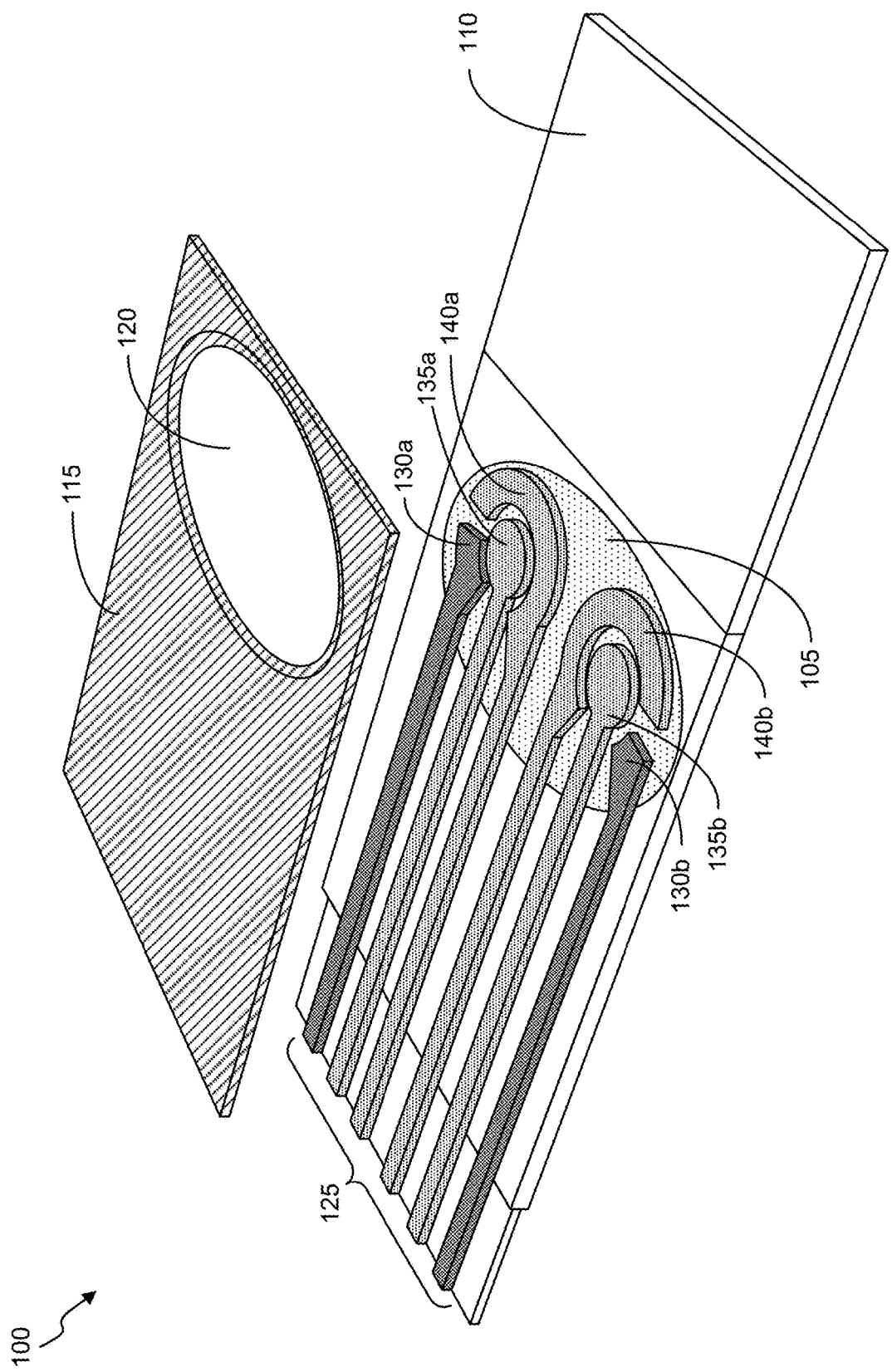

FIG. 1A and FIG. 1B provide schematic illustrations of an example electrochemical test strip device 100. FIG. 1A shows a top-down view of electrochemical test strip device 100 and FIG. 1B shows a perspective view of electrochemical test strip device 100. Electrochemical test strip device 100 includes a fluid chamber 105 containing two sets of three electrodes. Fluid chamber 105 includes a sensing chamber 105a (or test chamber) and a reference chamber 105b (or control chamber), each with a corresponding set of three electrodes. In some cases, sensing chamber 105a and reference chamber 105b can be physically separated from each other (e.g. by a barrier) or they can each be a subset of fluid chamber 105 in contact with a corresponding set of three electrodes. Electrochemical test strip device 100 also includes a holding or grasping area 110, which may optionally include a label, identifier, or barcode, which can facilitate identification of the particular analyte the electrochemical test strip device 100 is configured to detect, or other information. In some cases, holding or grasping area 110 is optional, and an identifier may optionally be positioned elsewhere on electrochemical test strip device 100. Electrochemical test strip device 100 also includes a cover plate 115 with an opening 120 for directing a test fluid to the fluid chamber 105, and a set of contacts 125 to enable electrical connection to an interface device. The three electrodes in each of the testing chamber 105a and the reference chamber 105b support stimulus and measurement via a potentiostat approach. In this approach, a fixed voltage is applied between two of the electrodes. The third electrode completes a circuit to enable precise measurement of current flow at those voltage conditions. Different voltages can be applied, in sequence, and the current at each voltage measured to produce a voltammogram, providing current as a function of voltage. The three electrodes are called the reference electrode (RE), working electrode (WE), and counter electrode (CE). Specifically, testing chamber 105a is depicted as including a reference electrode 130a, a working electrode 135a, and a counter electrode 140a and reference chamber 105b is depicted as including a reference electrode 130b, a working electrode 135b, and a counter electrode 140b.

Holding or grasping area 110 can comprise an extended region of a base supporting the two sets of electrodes and can comprise any suitable non-conducting material, such as a plastic, polymeric, fibrous, or non-porous material. The two sets of electrodes can comprise any suitable electrode material. For use in potentiostatic measurements, it may be beneficial for reference electrodes 130a and 130b to comprise Ag/AgCl, and for working electrodes 135a and 135b and counter electrodes 140a and 140b to comprise another metal, such as Au, Ag, Cu, or Pt. The legs of the electrodes may extend to the set of contacts 125 as the same conductive material present in fluid chamber 105, or the conductive material may change at the border of or outside fluid chamber 105 to another conductive material. Cover plate 115 can comprise any suitable non-conducting material, such as a plastic, polymeric, fibrous, or non-porous material.

In this example, working electrode 135a can be functionalized with a capture molecule, such as an active capture molecule that binds a particular analyte of interest. In some examples, the capture molecule can be an antibody or antibody component, functionalized with an electroactive redox tag, and coupled to the surface of the working electrode 135a by click chemistry, as described above, such as by way of a linking component (e.g., PEG-thiol molecule). The working electrode 135a can also include a charged passivation component (e.g., charged PEG-thiol molecules) that do not include the capture molecule. The working electrode 135b can be functionalized with a different capture molecule, such as a null capture molecule that does not binds the particular analyte of interest or that binds some other analyte. In some examples, the null capture molecule can be an antibody or antibody component, functionalized with an electroactive redox tag, and coupled to the surface of the working electrode 135b by click chemistry, as described above, such as by way of a linking component (e.g., PEG-thiol molecule). The working electrode 135b can also include a passivation component (e.g., a charged passivation component, such as charged PEG-thiol molecules) that do not include the capture molecule. In addition, working electrodes 135a and 135b can be coated, at least partly, with a hydrogel comprising a plurality of different charged glycosaminoglycans.

FIG. 2A shows a top-view schematic illustration of an example dual-chamber electrochemical test strip device 200 with a top fill configuration. In this example, there are two separate measurement chambers, a test chamber 205a with a reference electrode 230a, a working electrode 235a, and a control electrode 240a, and reference chamber 205b with a reference electrode 230b, a working electrode 235b, and a control electrode 240b. Two microfluidic channels are connected to the collection well 205 to bring the sample from there to the test chamber 205a and reference chamber 205b. The test chamber 205a is functionalized, with an attached antibody, such as at the working electrode 205a, while the reference chamber is not functionalized in the same way.

FIG. 2B shows a top-view schematic illustration of an example dual-chamber electrochemical test strip device 250 with an edge fill configuration. In this example, there are two separate measurement chambers, a test chamber 255a with a reference electrode 280a, a working electrode 285a, and a control electrode 290a, and reference chamber 255b with a reference electrode 280b, a working electrode 285b, and a control electrode 290b. Two microfluidic channels are connected to the collection well 255 to bring the sample from there to the test chamber 255a and reference chamber 255b. The test chamber 255a is functionalized, with an attached antibody, such as at the working electrode 255a, while the reference chamber is not functionalized in the same way.

Figure 3:
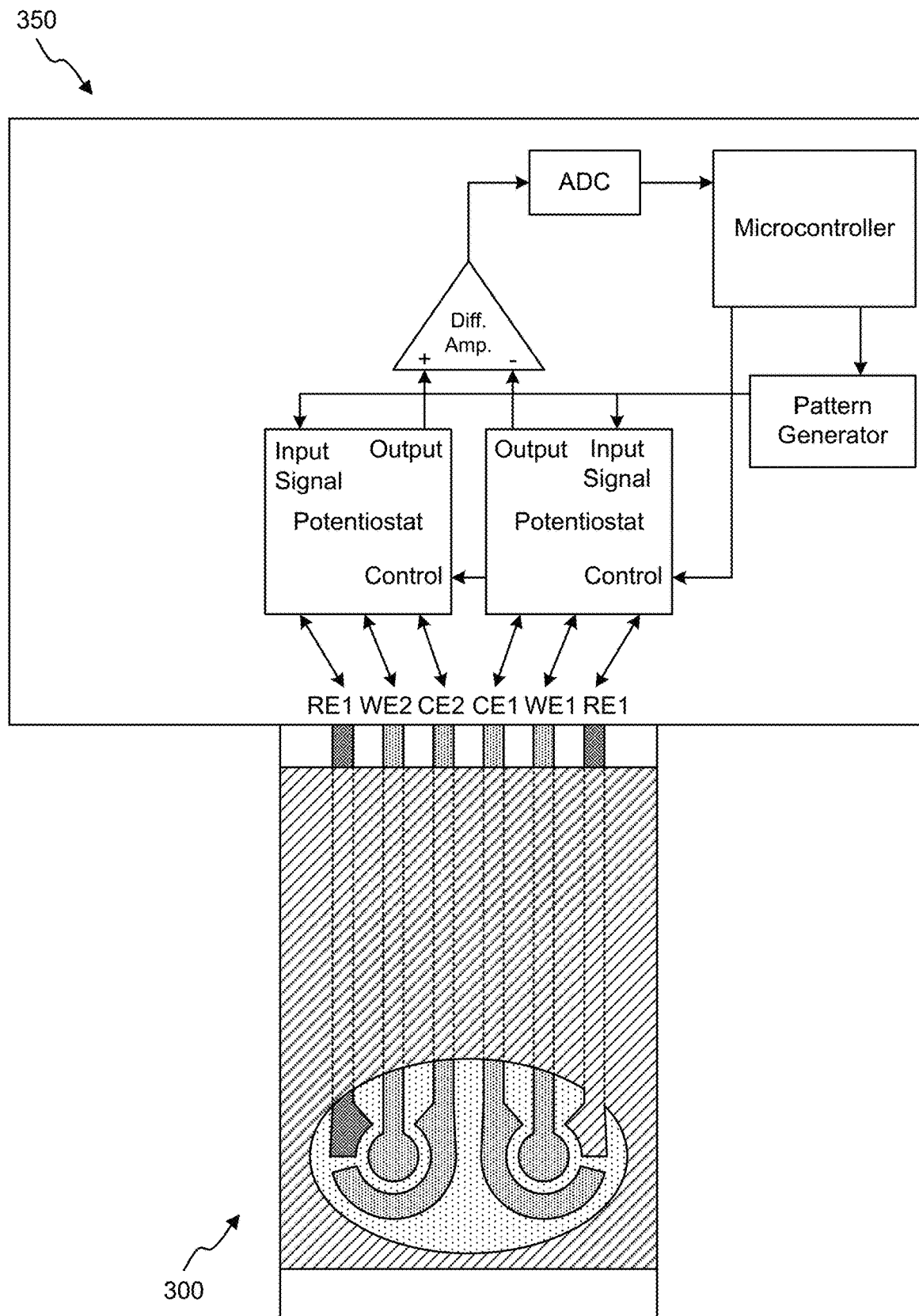
FIG. 3 shows a schematic illustration of an electrochemical test strip device connected to an interface device.

FIG. 3 shows a schematic illustration of an electrochemical test strip device 300 connected to an interface device 350. Interface device 350 comprises potentiostat circuit, which may comprise a variety of electrical circuit components including operational amplifiers (op-amps), control muxes, and precision resistors and capacitors, for example. The op-amps and muxes can themselves be built from standard MOSFETs, which are a form of transistors easily fabricated into integrated circuits. The potentiostat circuit may be implemented as a single-chip integrated circuit, enables the interface device 350 to be small, so that it can be easily hand-held. In some examples, the circuits components of the potentiostat circuit are analog in nature, but these can be coupled to a digital, general purpose microprocessor or microcontroller. The microprocessor can specify the input voltage to use and analyze the output signals. To enable this interaction, the interface device an also include very accurate digital to analog converters (DACs) and analog to digital converters (ADCs). In the configuration illustrated in FIG. 3, two separate potentiostat circuits are used to connect to the different sets electrodes of the sensing chamber and test chamber of electrochemical test strip device 300 to provide a differential signal, determined by a differential amplifier, that is converted from an analog signal to a digital signal and provided to the microcontroller. When an analyte binds to a capture molecule tethered to the working electrode, the current detected by the potentiostat circuit can be modulated (e.g., reduced) at a particular voltage, allowing detection of the binding event. Without wishing to be bound by any theory, the modulation in current can be due to a difference in proximity between an electroactive redox tag component of the capture molecule on binding the analyte that may occur due to an increased hydrodynamic drag due to the presence of the bound analyte. Generally, when an analyte is bound to the capture molecule, a reduction in current can be observed at a particular voltage compared to the current observed when no analyte is bound.

The disclosed electrochemical test strip devices and interface devices can be used together to sensitively and quickly determine the presence, absence, or concentration of a particular analyte in a test fluid for use in diagnosing a condition, infection, or disease. In some examples, any of a variety of analytes may be detected by functionalizing a working electrode of the electrochemical test strip device with an appropriate capture molecule. Conditions, infections, or diseases of interest include, but are not limited to: SARS-CoV2, SARS-CoV2 variant, Influenza, Ebola, Malaria, Acute coronary syndrome, Acute Myocardial infarction, Heart failure, Cardiac Ischemia, Acute Coronary Syndrome, Acute Cardiac Disorders, Transplant rejection, Schistosomiasis, Lymphatic filariasis, Onchocerciasis, Chagas Disease, African tyrpanosomaniasis, Leishmaniasis, Leprosy, Dengue Fever, Tuberculosis, Hookworm, Trichuriasis, Treponematoses, Buruli Ulcer, Dracunculiasis, Leptospirosis, Strongyloidiasis, Foodborne trematodiases, Neurocysticercosis, Flavivirus, Stroke, Traumatic Brain Injury, Liver cancer and germ cell tumors, Multiple myeloma, chronic lymphocytic leukemia, lymphomas, Choriocarcinoma and germ cell tumors, Thymoma, Thyroid carcinoma, Testicular germ cell tumor/carcinoma, Ovarian germ cell tumor/carcinoma, Saccrococcygeal teratoma, Bladder cancer and cancer of the kidney or ureter, Colorectal cancer, Neuroendocrine tumors, Lung cancer, pancreatic cancer, Gastrinoma, Small cell lung cancer and neuroblastoma, Metastatic prostate cancer, Mesothelioma, Thyroid cancer, Kidney schlerosis, kidney fibrosis, glomerular injury, kidney failure, glomerulosclerosis, or glomerulonephritis, Acute Kidney injury, Interstitial cystitis, Kidney Graft rejection, Illicit drug use, performance enhancing substance use, Syphilis, Gonorrhea, Chlamydia, Trichomoniasis, HBV, HSV, HIV, HCV, HPV, MRSA, Zika, Sepsis, Cytokine storm, Acute pulmonary embolism, Heart Failure, Nonalcoholic fatty liver disease, Pancreatitis, Neurodegeneration, brain injury, Alzheimer's, Parkinson's, or combinations of these.

Analytes of interest for detecting or diagnosing the above diseases, infections, or conditions include, but are not limited to: SARS-CoV-2 nucleocapsid protein, SARS-CoV-2 Spike protein, influenza high affinity hemagglutinin binding protein, Ebola virus Glycoprotein, ANG-2, VWF, VWFpp, sICAM-1, sFLT-1, sTie-2, CRP, PCT, IP-10, CHI3L1 and sTREM-1, Cardiac Troponin I (cTnI), H-FABP, BNP, NT Pro-BNP, Nitrated cTnI, acetate, acetone, cytosine, methylmalonate, phenylacetylglycine, soluble CD40 ligand, atrial natriuretic peptide (ANP), schistosome circulating cathodic antigen, Circulating antigens detected by OG4c3 Mab, Oncho-C27 antigen, *Trypanosoma cruzi* circulating antigens, GM6, *Leishmania major* antigen TSA, phenolic glycolipid-I antigen of *M. leprae*, Dengue NS 1 and/or envelope protein, RD1, RD2, or RD3 of *Mycobacterium tuberculosis*, hookworm ASPS, Whipworm coproantigen, Tp47, Tp17, Tp15, TmpA, or TmpB, mycolactone, the primary lipidic toxin A of *Mycobacterium ulcerans*, OV-10, OV-11 and OV-16, core lipopolysaccharide of Leptospira spp, *Strongyloidiasis* spp L3 stage antigens, secretory coproantigens of intestinal and liver flukes, T24, NS5, S100 calcium binding protein B (5-100B), neuron-specific enolase (NSE), myelin basic protein (MBP), Microtubule Associated Protein 2 (MAP2), glial fibrillary acidic protein (GFAP), ubiquitin carboxyl-terminal esterase L1 (UCH-L1), glial fibrillary acid protein (GFAP), aldehyde dehydrogenase 1 family member LI (ALDHILI), phosphorylated neurofilament heavy chain (pNFH), medium chain (NFM), or light chain (NFL), alpha-synuclein, visinin-like protein 1 (VILIP-1), S100B, Neuron Specific Enolase (NSE), Glial Fibrillary Acidic Protein (GFAP), Ubiquitin Carboxy-Terminal Hydrolase L1 (UCH-L1), Interleukin-1b (IL-Ib), Interferon Gamma (IFN-g), Interleukin 8 (IL-8), Interleukin 10 (IL-10), Spectrin II, 8-Hydroxy-2'-Deoxyguanosine (8-OHdG), Alpha-fetoprotein (AFP), Beta-2-microglobulin (B2M), Beta-human chorionic gonadotropin (Beta-hCG), Bladder Tumor Antigen (BTA), Carcinoembryonic antigen (CEA), epidermal growth factor receptor, leucine-rich alpha-2 glycoprotein, inter-alpha trypsin inhibitor heavy chain 3, inter-alpha trypsin inhibitor heavy chain 4, dipeptidyl peptidase 4, peptidase inhibitor 16, coagulation factor V, C-reactive protein, Rho-GDP dissociation inhibitor 1 isoform A, hemopexin, extracellular superoxide dismutase[Cu—Zn], thrombospondin-4, collagen alpha-1(1) chain, cadherin-2, vitronectin, Chromogranin A (CgA), Cytokeratin fragment 21-1, Gastrin, Neuron-specific enolase (NSE), Nuclear matrix protein 22, Prostate specific antigen (PSA), C reactive protein (CRP), chromogranin A (CHGA), bone alkaline phosphatase (BAP), cysteine-rich secretory protein 3 (CRISP3), ERG, prostatic acid phosphatase (PAP; also called ACP3; human acid phosphatase 3, prostatic), Apolipoprotein A2 (ApoA2), Apolipoprotein C1 (ApoC1), Soluble mesothelin-related peptides (SMRP), Thyroglobulin, S100A8, CSTA (cystatin A), GRM1 (glutamate receptor, metabotropic 1), TPT1 (tumor protein, translationally-controlled 1), GRIK1 (glutamate receptor, ionotropic, kainate 1), H6PD (hexose-6-phosphate dehydrogenase), IGF2BP1 (insulin-like growth factor 2 mRNA binding protein 1), MDM4 (3T3 cell double minute 4), CA6 (carbonic anhydrase VI), epidermal growth factor receptor, leucine-rich alpha-2 glycoprotein, inter-alpha trypsin inhibitor heavy chain 3, inter-alpha trypsin inhibitor heavy chain 4, dipeptidyl peptidase 4, peptidase inhibitor 16, coagulation factor V, C-reactive protein, Rho-GDP dissociation inhibitor 1 isoform A, hemopexin, extracellular superoxide dismutase [Cu—Zn], thrombospondin-4, collagen alpha-1(1) chain, cadherin-2, vitronectin, Annexin A1, Rab23, Kidney injury molecule-1 (KIM-1), neutrophil gelatinase associated lipocalin (NGAL), interleukin-18 (IL-18), hepatocyte growth factor (HGF), cystatin C (Cys), N-acetyle-β-D-glucosaminidase (NAG), vascular endothelial growth factor (VEGF), chemokine interferon-inducible protein 10 (IP-10; CXCL10), Antiproliferative factor (APF), CD44, UMOD, PEDF, MMPI, SERPING1, COL1A2, COL3A1, TIMP1, neurogranin (NRGN), myelin basic protein (MBP), glial fibrillary acid protein (GFAP), peptidylarginine deiminase (PAD), IGF-I, IGF-II, Aβ-40, Aβ-42, alpha amylase, IL-1 beta, TNF-alpha, Tp47, Tp17, Tp15, TmpA, TmpB, Gonorrhea antigens, Chlamydia antigens, Trichomonas adhesin peptide, PreS1, PreS2, gC2, gG2, gB2, gD2, P24, Oxycodone, opiates, cocaine, cannabinoids, barbiturates, methamphetamine, amphetamine, benzodiazepine, methadone, TCAs, ecstasy, cotinine, Clenbuterol, DHEA, 7-hydroxy-DHEA, 7-Keto-DHEA (dehydroepiandrosterone), andarine, ostarine, LGD-4033, RAD-140, albuterol, formoterol, salmeterol, androstenedione, methenolone, Tetrahydrogestrinone, oxymetholone, Oxandrolone, methandrostenolone, Stanozolol, nandrolone decanoate, nandrolone phenpropionate, testosterone cypionate, boldenone undecylenate, Testosterone enanthate, Epogen, Procrit, hCG, anastrozole, tamoxifen, P24, c200-3, NS-5 and a modified core antigen, epitope of the C-terminal or the N-terminal region of a HPV E7 protein, MV0118 protein, lateral ridge (LR) or the CC loop within domain III (DIM) of the E protein of Zika virus, Procalcitonin, Angiopoietin 1 and 2, Endocans, TREM-1, ctla-4, *Staphylococcus aureus*, Coagulase-negative staph, *Streptococcus pneumonia*, *Haemophilus* influenza b, *Neisseria meningitis*, *Klebsiella pneumonia*, *Enterococcus faecalis*, *Acinetobacter baumanii*, *Escherichia coli*, *Salmonella enterica*, *Shigella dysenteriae*, *Citrobacter freundii*, *Serratia marcescens*, *Proteus mirabilis*, *Pseudomonas aeruginosa*, *Bacteroides fragilis* IL-2, IL-6, IL-7, IL-10, G-CSF, TNF, CXCL10, MCP1, MIP1α, D-Dimer, C-reactive protein, LDH, ferritin, IFN-γ, IP-10, IL-6, MCP-1, TNF-α, IgA, IgG, IgM, Procalcitonin (PCT), C-reactive protein (CRP), Interleukin 6 (IL-6), Pre-sepsin, Soluble intercellular adhesion molecule-1 (sICAM-1), Endocan, D-dimer, Lactate dehydrogenase (LDH), or combinations or metabolites thereof. In some examples, particular analytes may be useful for diagnosing a severity of an infection, such as infection by SARS-CoV-2 or a SARS-CoV-2 variant, such as Procalcitonin (PCT), C-reactive protein (CRP), Interleukin 6 (IL-6), D-dimer, Lactate dehydrogenase (LDH).

Figure 4:
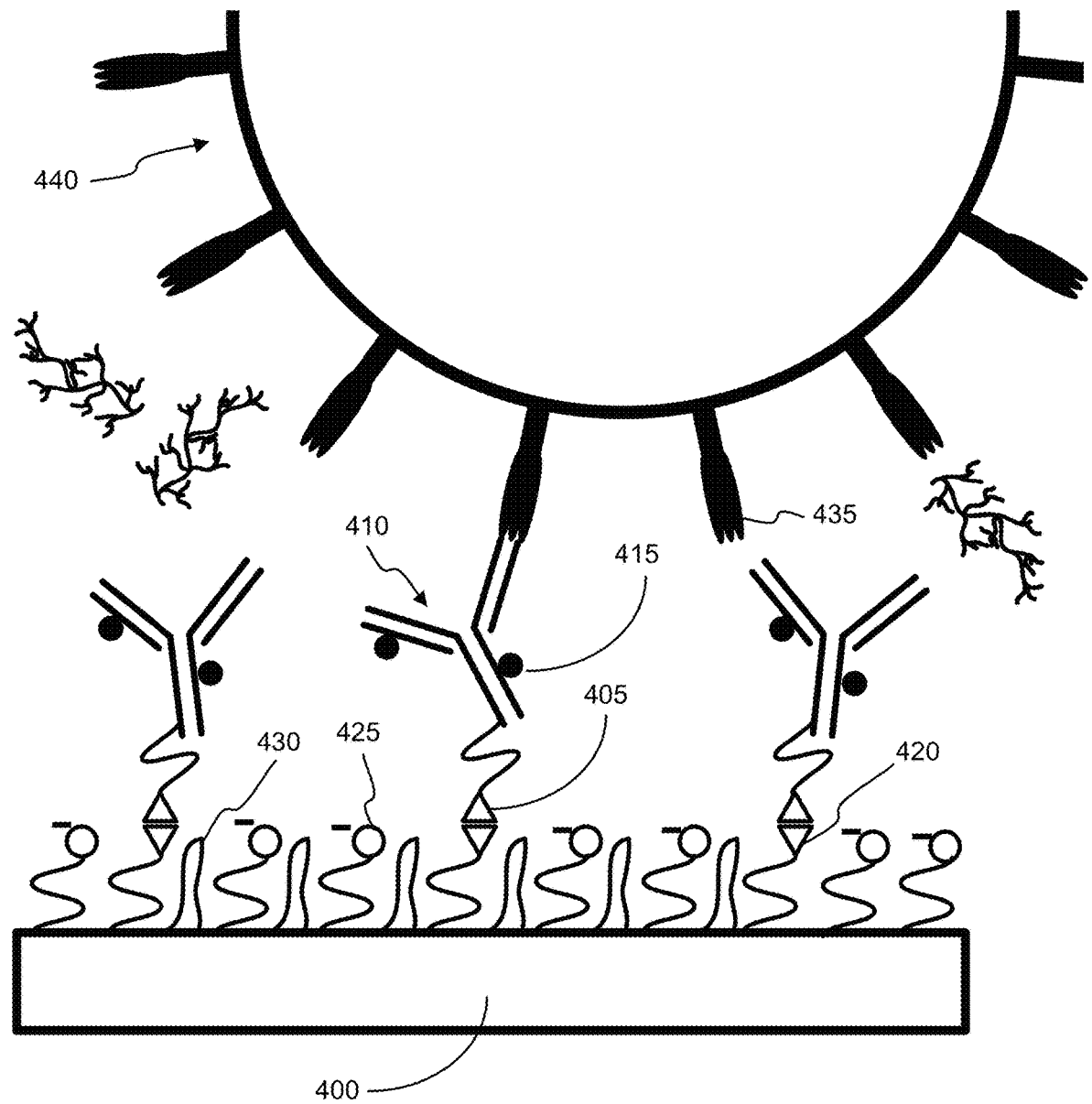
FIG. 4 shows a schematic illustration of a working electrode of an example electrochemical test strip device functionalized with capture molecules for use in a biosensor rapid antigen assay.

FIG. 4 shows a schematic illustration of a working electrode 400 of an example electrochemical test strip device functionalized with capture molecules for use in a biosensor rapid antigen assay. In this example, the capture molecules include antibodies that bind SARS-CoV-2. The working electrode 400 comprises gold screen printed on a surface. Cu assisted click chemistry is used to covalently link azido 405 modified monoclonal SARS-CoV-2 antibodies 410 with an electroactive redox tag 415 to the gold surface via a PEG-thiol linker with a terminal alkyne group 420. An anti-biofouling layer made of a hydrogel comprising charged PEG layers 425 and lubricin (PRG4) 430 helps repel the non-specific binding proteins in the sample. This virus-detecting assay uses the kinetic response of a probe/virus complex to analyze the complexation state of the antibody. This approach employs electrode-tethered sensors including an analyte-binding antibody 410 tagged with an electroactive redox probe 415 covalently bound on a neutrally charged PEG linker. When a positive potential is applied to the working electrode 400, the proximity between the electroactive redox tag 415 and the gold surface is modulated. The binding between the antibodies 410 and the viral proteins 435 of the SARS-CoV-2 viral particles 440 induces a hydrodynamic drag on the modulation, allowing the presence of viral proteins 435 and particles 440 to be detected using potentiometry measurements.

Figure 5:
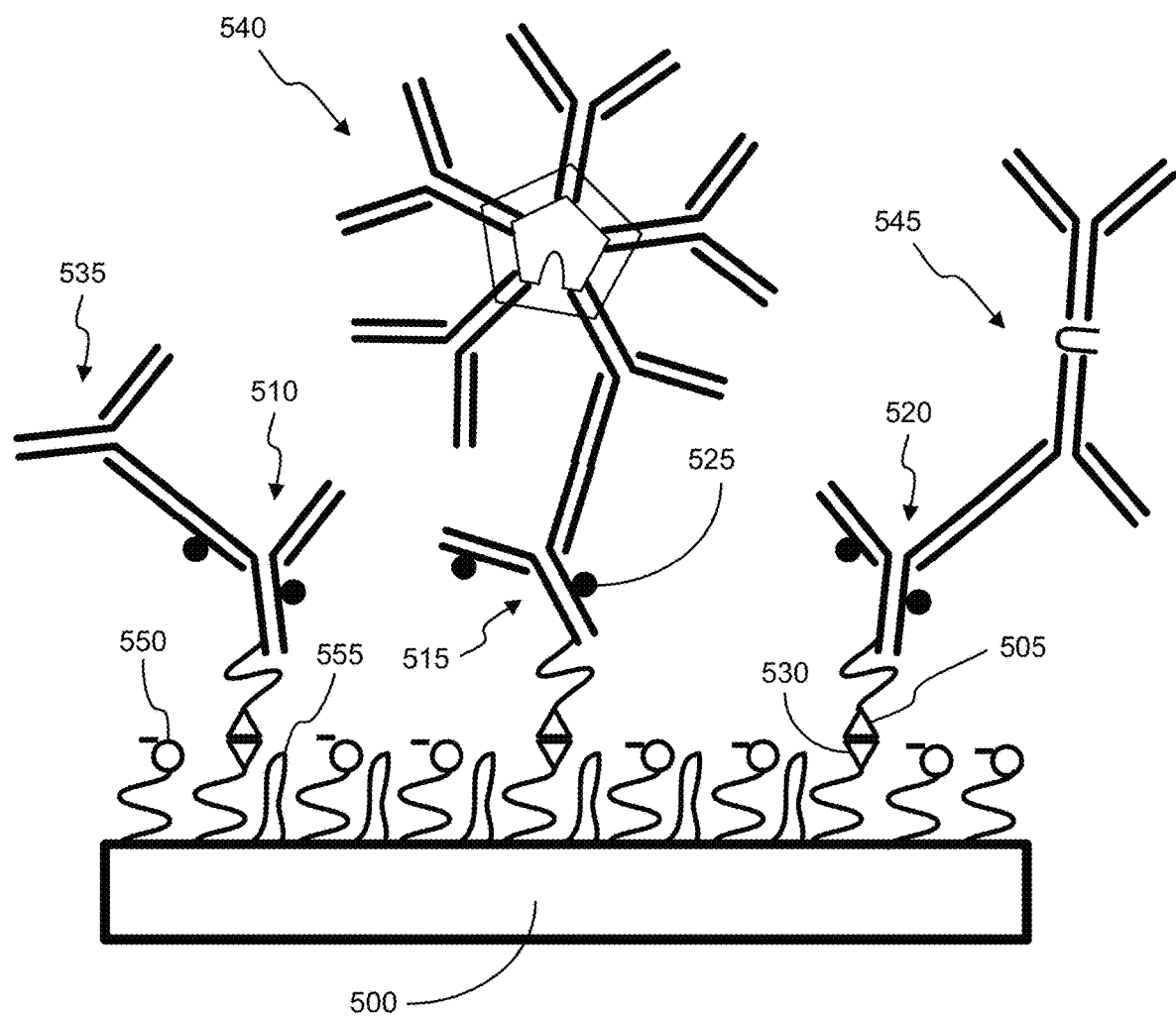
FIG. 5 shows a schematic illustration of a working electrode of an example electrochemical test strip device functionalized for an electrochemical biosensor based antibody assay to determine host immune response.

FIG. 5 shows a schematic illustration of a working electrode 500 of an example electrochemical test strip device functionalized for an electrochemical biosensor based antibody assay to determine host immune response, again using SARS-CoV-2 as an example. The working electrode 500 comprises gold screen printed on a surface. Cu assisted Click chemistry is used to covalently link azido 505 modified anti-immunoglobulin antibodies 510, 515, and/or 520, including an electroactive redox tag 525, to the gold surface via a PEG-thiol linker with a terminal alkyne group 530. This allows preparation of electrode-tethered anti-antibodies 510, 515, and/or 520 tagged with the electroactive redox probe 525 to be covalently bound on a neutrally charged PEG linker. When a host sample is introduced, the anti-immunoglobulin antibodies 510, 515, and/or 520 bind to either IgG antibodies 535, IgM antibodies 540, or IgA antibodies 545 in the sample. An anti-biofouling layer made of a hydrogel comprising charged PEG layers 550 and lubricin (PRG4) 555 helps repel non-specific binding proteins in the sample. When a positive potential is applied to the working electrode 500, the proximity between the electroactive redox tag 525 and the gold surface is modulated. The binding between the anti-antibodies 510, 515, and/or 520 and the IgG antibodies 535, IgM antibodies 540, or IgA antibodies 545 in the sample induces a hydrodynamic drag on the modulation, allowing the presence of IgG antibodies 535, IgM antibodies 540, or IgA antibodies 545 in the sample to be confirmed using potentiometry measurements.

Figure 6:
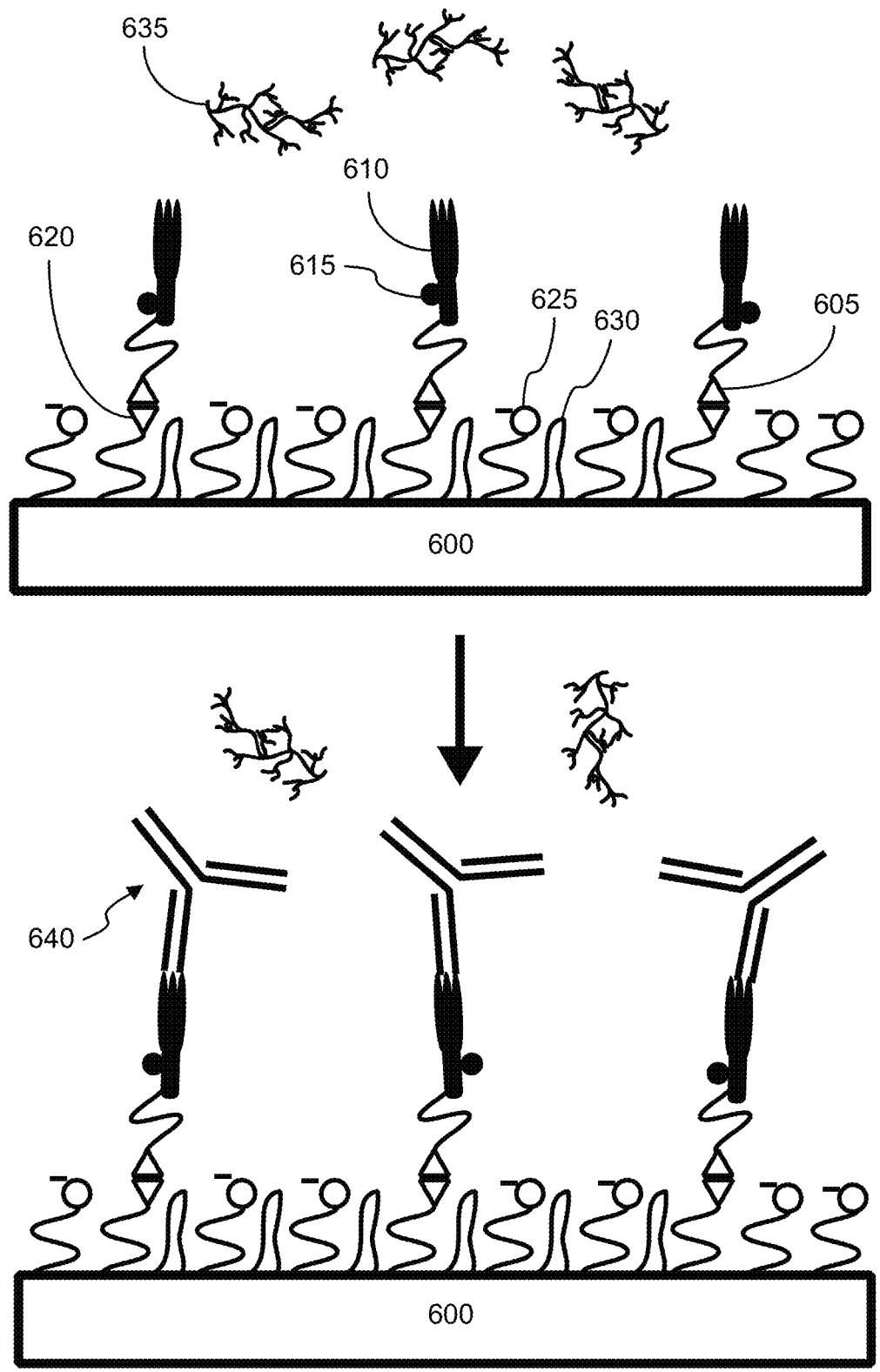
FIG. 6 shows a schematic illustration of a working electrode of an example electrochemical test strip device functionalized for an electrochemical biosensor rapid host immune response assay.

FIG. 6 shows a schematic illustration of a working electrode 600 of an example electrochemical test strip device functionalized for an electrochemical biosensor rapid antigen assay, again using SARS-CoV-2 as an example. The working electrode 600 comprises gold screen printed on a surface. Cu assisted click chemistry is used to covalently link the azido 605 modified monoclonal SARS-CoV-2 spike antigens 610 with an electroactive tag 615 to the gold surface via a PEG-thiol linker with a terminal alkyne group 620. This allows preparation of electrode-tethered antigens 610 tagged with the electroactive redox probe 615 to be covalently bound on a neutrally charged PEG linker. An anti-biofouling layer made of a hydrogel comprising charged PEG layers 625 and lubricin (PRG4) 630 helps repel non-specific binding analytes 635 in the sample. When a positive potential is applied to the working electrode 600, the proximity between the electroactive redox tag 615 and the gold surface is modulated. If antibodies 640 are present in the sample, such as produced as a result of virus exposure or vaccination, these antibodies 640 can bind to the tethered antigen 610, and the binding event can impact the modulation rate induced by the application of potential to the working electrode 600, leading to a detectable difference in current output measured using potentiometry versus the non-binding configuration when the antibodies 610 are not present, indicating vaccine status or prior infection status.

Figure 7:
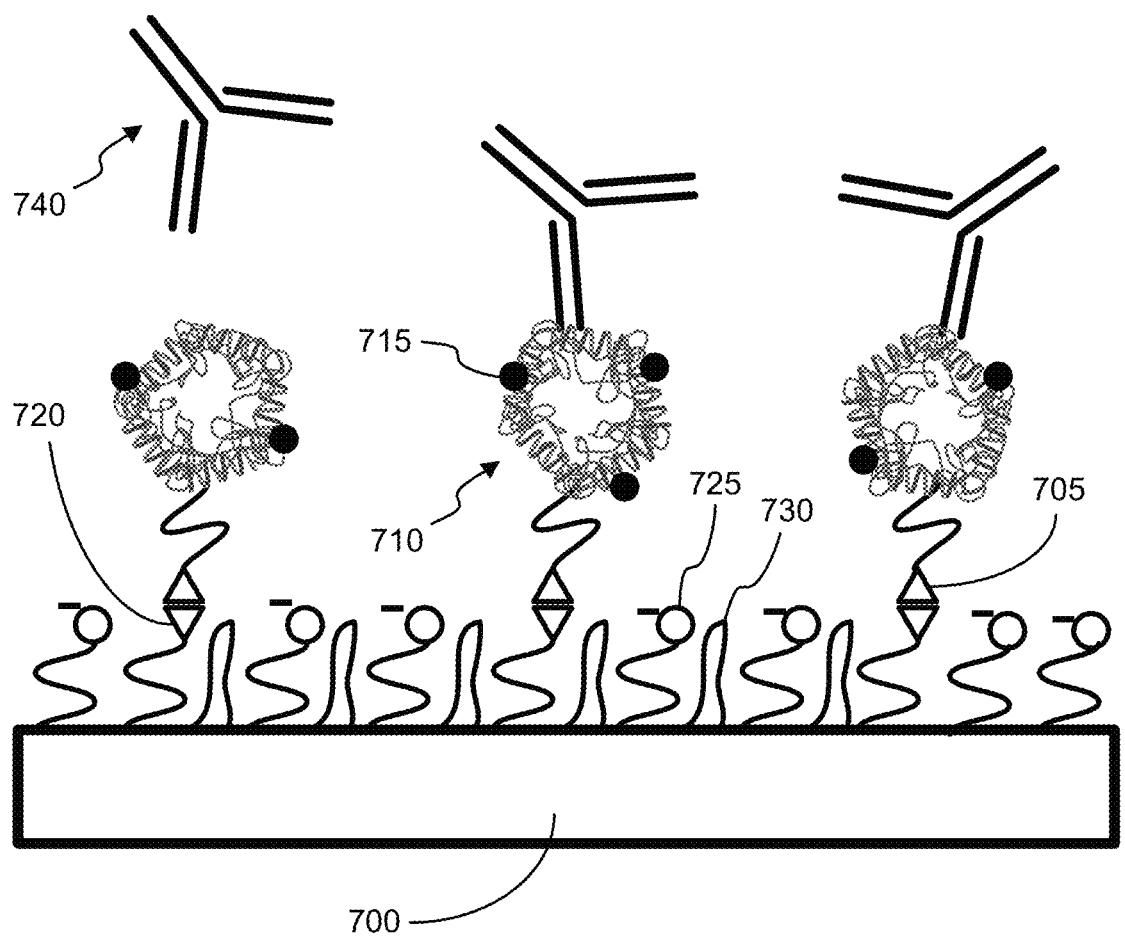
FIG. 7 shows a schematic illustration of a working electrode of an example electrochemical test strip device functionalized for an electrochemical biosensor rapid host immune response assay.

FIG. 7 shows a schematic illustration of a working electrode 700 of an example electrochemical test strip device functionalized for an electrochemical biosensor rapid antigen assay, again using SARS-CoV-2 as an example. Cu assisted click chemistry is used to covalently link the azido 705 modified monoclonal SARS-CoV-2 nucleocapsid antigens 710 with an electroactive tag 715 to the gold surface via a PEG-thiol linker with a terminal alkyne group 720. This allows preparation of electrode-tethered antigens 710 tagged with the electroactive redox probe 715 to be covalently bound on a neutrally charged PEG linker. An anti-biofouling layer made of a hydrogel comprising charged PEG layers 725 and lubricin (PRG4) 730 helps repel non-specific binding analytes in the sample. When a positive potential is applied to the working electrode 700, the proximity between the electroactive redox tag 715 and the gold surface is modulated. With current SARS-CoV-2 vaccines employing spike antigens and not other SARS-CoV-2 antigens, a distinction between antibodies present due to infection or vaccination can be identified, as antibodies to the SARS-CoV-2 nucleocapscid protein or SARS-CoV-2 envelope protein will likely only be in a test fluid if the test fluid is from an individual that has developed antibodies due to infection by SARS-CoV-2. If antibodies 740 are present in the sample that bind to the tethered antigen 710, such as produced as a result of virus exposure, the binding event can impact the modulation rate induced by the application of potential to the working electrode 700, leading to a detectable difference in current output measured using potentiometry versus the non-binding configuration when the antibodies 710 are not present, indicating prior infection status.

In some cases, a working electrode of one set of electrodes in an electrochemical test strip device can be functionalized with a vaccine specific tethered antigen (e.g., as depicted in FIG. 6) and a working electrode of another set of electrodes in the electrochemical test strip device can be functionalized with an infection specific tethered antigen (e.g., as depicted in FIG. 7) to provide an electrochemical biosensor rapid antigen assay that distinguishes between immunity due to vaccination or immunity due to natural infection.

Figure 8:
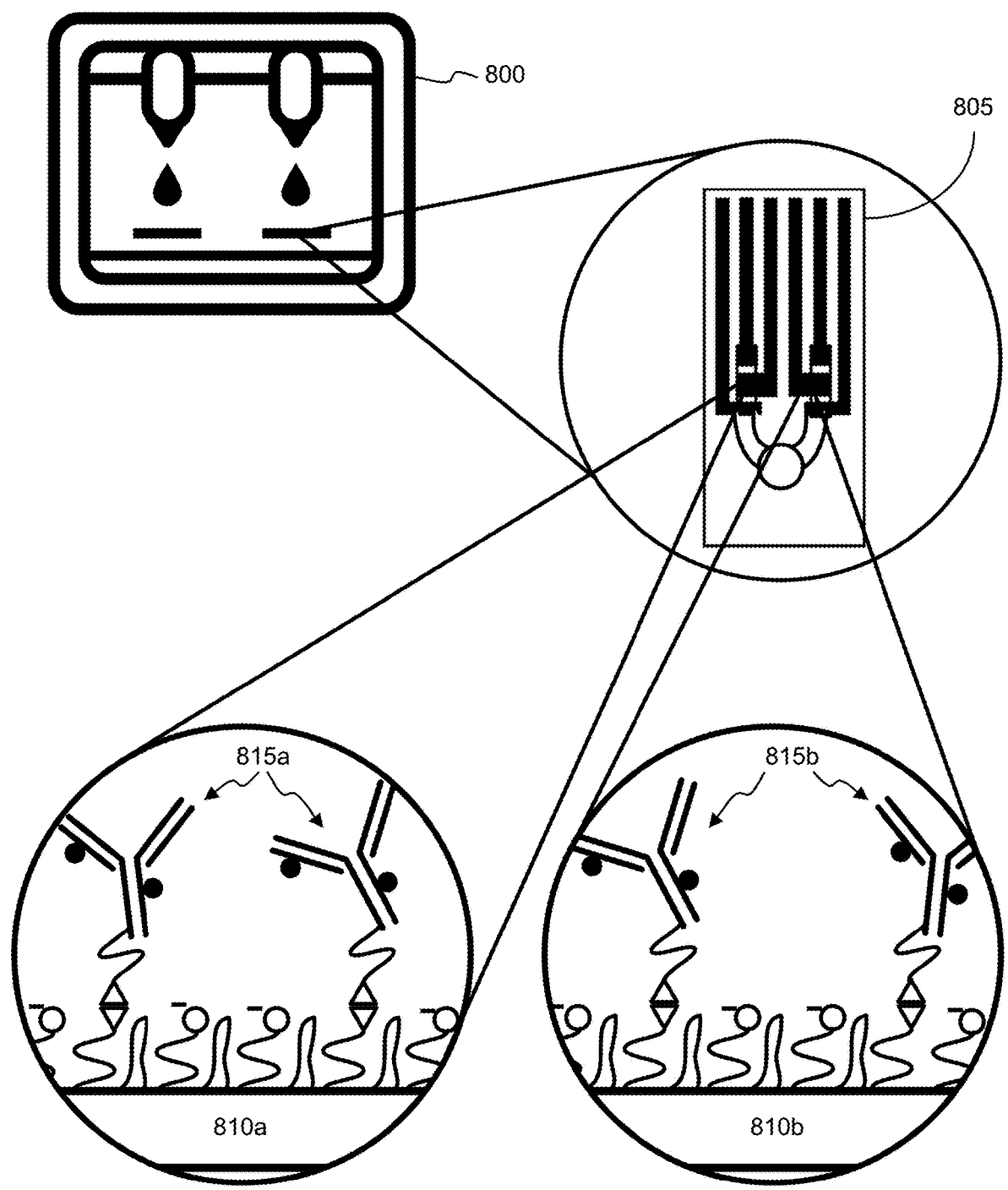
FIG. 8 shows a schematic illustration of a bioprinted electrochemical biosensor based multi-antigen assay using influenza and SARS-CoV-2 as examples.

FIG. 8 shows a schematic illustration of an electrochemical biosensor based multi-antigen assay using influenza and SARS-CoV-2 as examples. Bioprinter 800 is used for high speed printing of capture molecules (e.g., antibodies or antigens) on the surfaces of working electrodes in an electrochemical test strip device 805. The electrochemical test strip device strip 805 comprises two test chambers each with gold working electrodes 810a and 810b screen printed on the surface. Cu assisted click chemistry is used to covalently link azido modified capture molecules (e.g., monoclonal antibodies or antigens) with an electroactive tag to the gold surface via a PEG-thiol linker with a terminal alkyne group. In some examples, the capture molecules immobilized in the first chamber are a cocktail of antibodies 815a specific to SARS-CoV-2 proteins and the monoclonal antibodies immobilized in the second chamber are antibodies 815b specific to influenza proteins. This configuration allows for a differential signal to be measured based on the binding of the antibodies 815a and 815b to target analytes (e.g., SARS-CoV-2 proteins or influenza proteins) and as such can be used to distinguish between influenza and SARS-CoV-2 and provide a rapid diagnosis of one infection condition versus the other.

Figure 9:
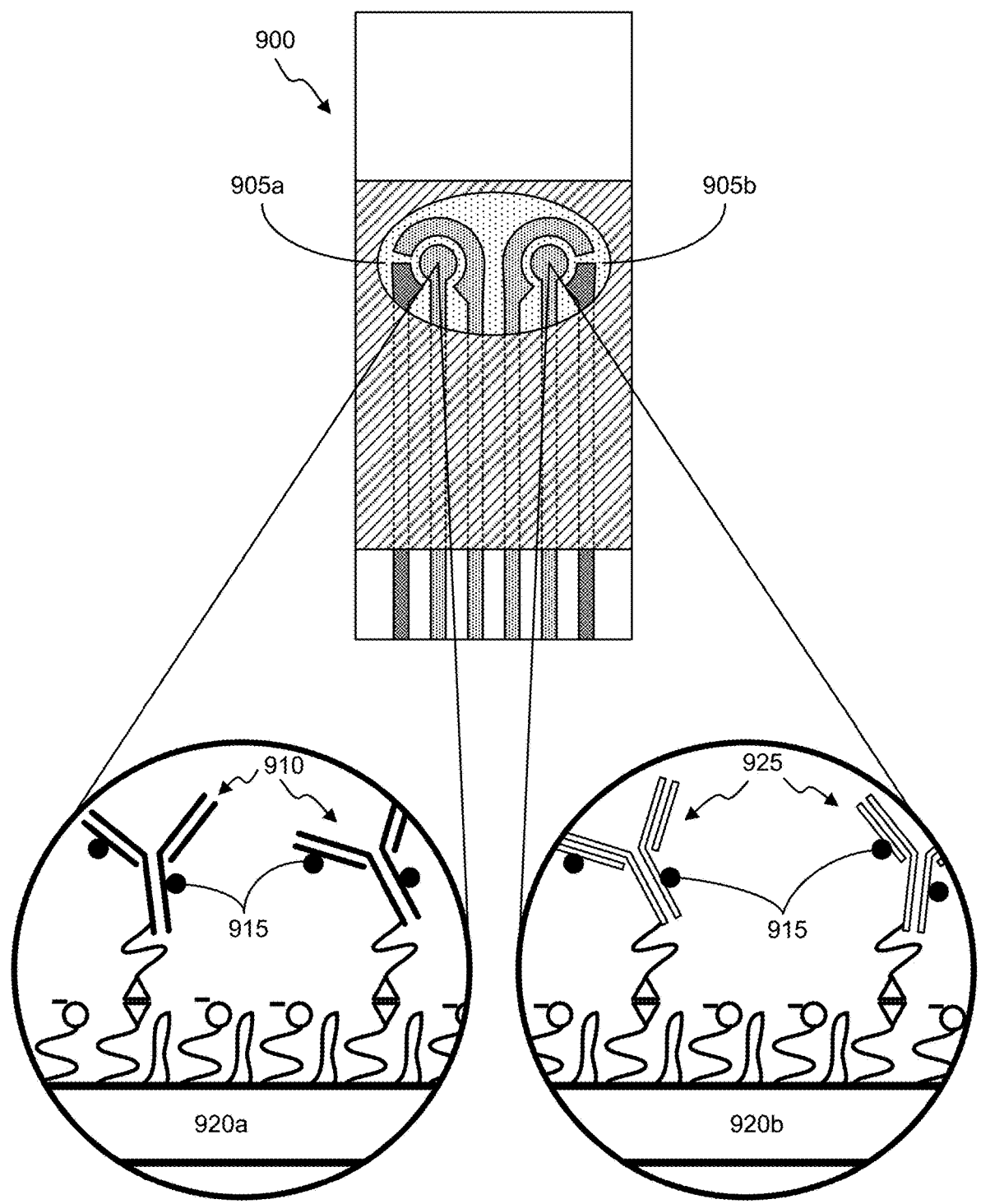
FIG. 9 provides a schematic illustration of another electrochemical biosensor rapid antigen assay exemplified as a functionalized electrochemical test strip device.

FIG. 9 provides a schematic illustration of another electrochemical biosensor rapid antigen assay exemplified as a functionalized electrochemical test strip device 900. An electrochemical test strip device 900 includes two chambers—a test chamber 905a and a reference chamber 905b, each having a set of 3 electrodes and a reservoir for introduction of test fluid. In the test chamber 905a, active antibodies 910 with electroactive tags 915 are immobilized on the surface of working electrode 920a using click chemistry via a PEG linker, as described above. In the reference chamber 905b, null antibodies 925 are immobilized on the surface of working electrode 920b in a similar fashion. Using potentiostatic measurements, a difference in the current output measured using the electrodes in the test chamber 905a and the reference chamber 905b when exposed to a test fluid can indicate the presence or absence of a particular antigen.

Figure 10:
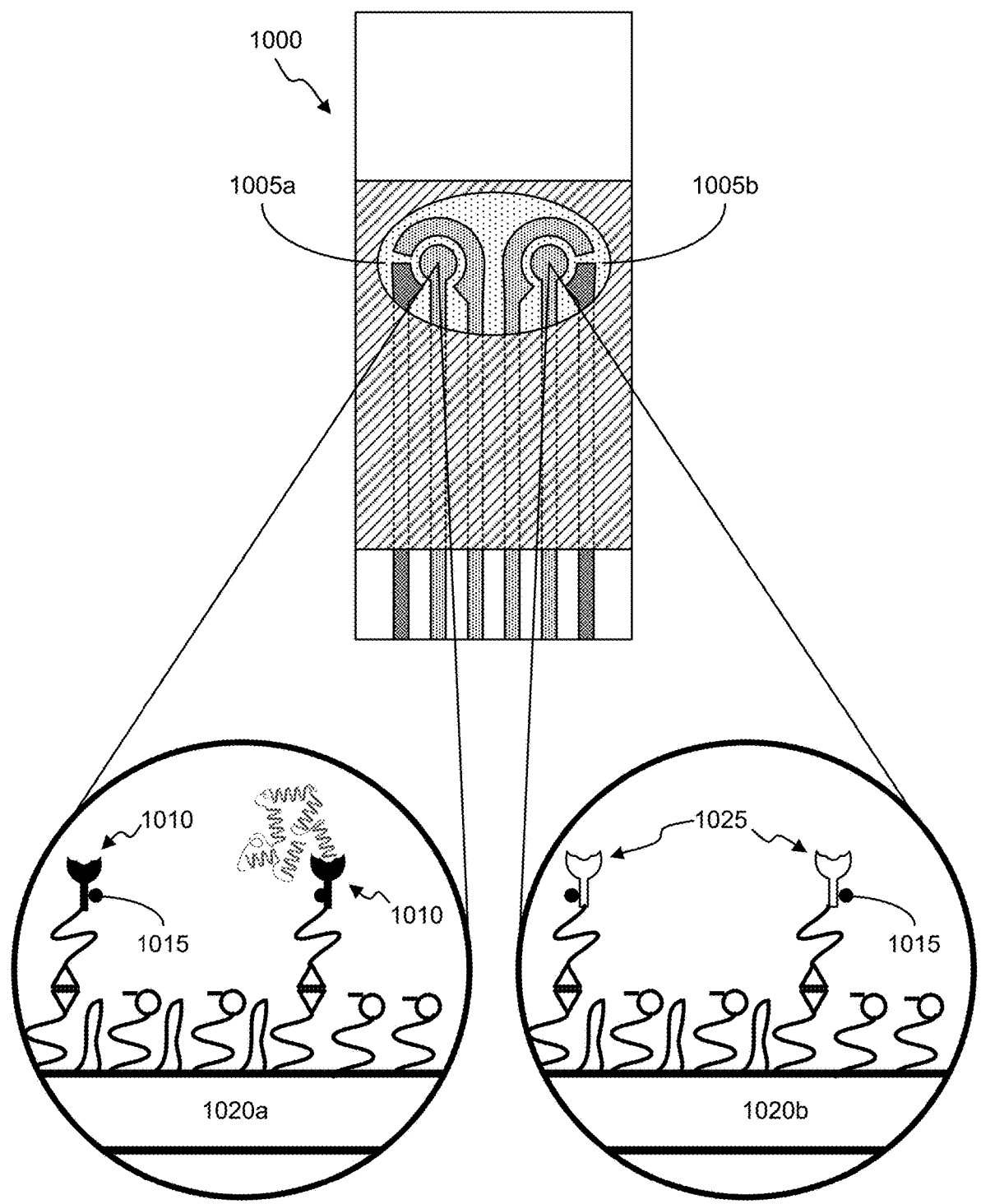
FIG. 10 provides a schematic illustration of another electrochemical biosensor rapid antigen assay exemplified as a functionalized electrochemical test strip device.

FIG. 10 provides a schematic illustration of another electrochemical biosensor rapid antigen assay exemplified as a functionalized electrochemical test strip device 1000. Electrochemical test strip device 1000 includes two chambers—a test chamber 1005a and a reference chamber 1005b, each having a set of 3 electrodes and a reservoir for introduction of test fluid. In the test chamber 1005a, active receptor proteins 1010 with electroactive tags 1005 are immobilized on working electrode 1020a using click chemistry via a PEG linker, as described above. In the reference chamber 1005b, null receptor proteins 1025 with electroactive tags are immobilized on the surface of working electrode 1020b in a similar fashion. Using potentiostatic measurements, a difference in the current output measured using the electrodes in the test chamber 1005a and the reference chamber 1005b when exposed to a test fluid can indicate the presence or absence of a particular analyte 1030 that binds to the active receptor protein 1010 or the null receptor protein 1025.

Figure 11:
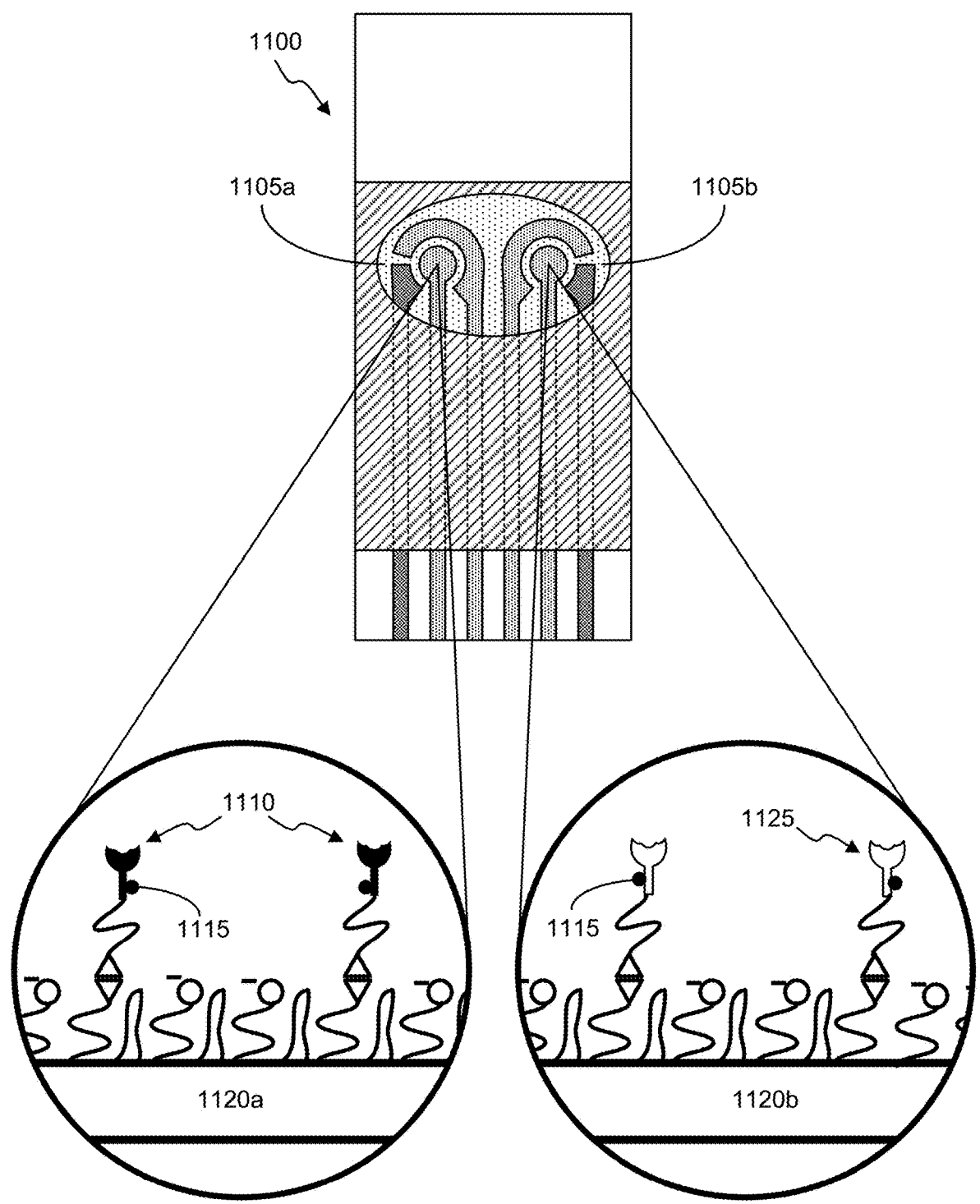
FIG. 11 provides a schematic illustration of another electrochemical biosensor rapid antigen assay exemplified as a functionalized electrochemical test strip device.

FIG. 11 provides a schematic illustration of another electrochemical biosensor rapid antigen assay exemplified as a functionalized electrochemical test strip device 1100. Electrochemical test strip device 1100 includes two chambers—a test chamber 1105a and a reference chamber 1105b, each having a set of 3 electrodes and a reservoir for introduction of test fluid. In the test chamber 1105a, active receptor aptamers 1110 with electroactive tags 1105 are immobilized on working electrode 1120a using click chemistry via a PEG linker, as described above. In the reference chamber 1105b, null receptor aptamers 1125 with electroactive tags are immobilized on the surface of working electrode 1120b in a similar fashion. Using potentiostatic measurements, a difference in the current output measured using the electrodes in the test chamber 1105a and the reference chamber 1105b when exposed to a test fluid can indicate the presence or absence of a particular analyte that binds to the active receptor aptamer 1110 or the null receptor aptamer 1125.

Figure 12:
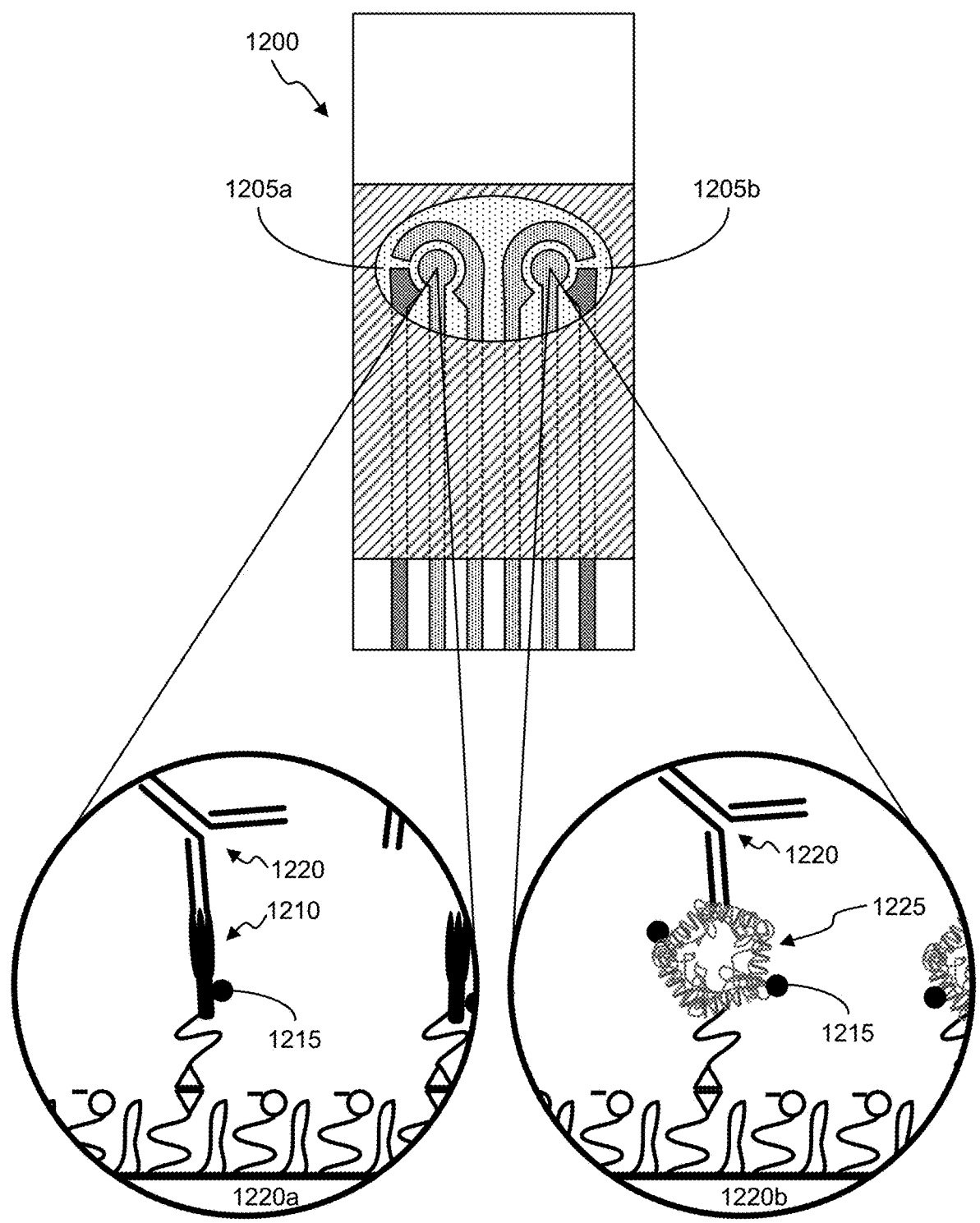
FIG. 12 provides a schematic illustration of another electrochemical biosensor rapid antigen assay exemplified as a functionalized electrochemical test strip device.

FIG. 12 provides a schematic illustration of another electrochemical biosensor rapid antigen assay exemplified as a functionalized electrochemical test strip device 1200. Electrochemical test strip device 1200 includes two chambers—a test chamber 1205a and a reference chamber 1205b, each having a set of 3 electrodes and a reservoir for introduction of test fluid. In the test chamber 1205a, the antigens include SARS-CoV-2 spike antigens 1210, specific to antibodies produced due to vaccination, coupled to an electroactive tag 1215, which is immobilized on working electrode 1220a using click chemistry via a PEG linker, as described above. In the reference chamber 1205b, the antigens include SARS-CoV-2 nucleocapsid antigens 1225, specific to antibodies produced due to virus exposure, coupled to an electroactive tag 1215, which is immobilized on the surface of working electrode 1220b in a similar fashion. Using potentiostatic measurements, a difference in the current output measured using the electrodes in the test chamber 1205a and the reference chamber 1205b when exposed to a test fluid can indicate the presence or absence of a particular analyte that binds to the spike antigen 1210 or the nucleocapsid antigen 1225. This assay can be used to distinguish between subjects who have been vaccinated against SARS-CoV-2 with a vaccine based on the spike antigen and those who were infected by SARS-CoV-2, which induces a humoral response against the spike antigen as well as the nucleocapsid antigen.

In an embodiment, an electrochemical test strip device described herein obtains a fluid sample from an individual through physical contact. For example, an electrochemical test strip device may be placed in the mouth of an individual. In other examples, a collection device (e.g., a dropper) is placed in the individual's mouth to collect saliva, which is then applied to a fluid chamber of the electrochemical test strip device. In other examples, a collection device is used to obtain another fluid sample (e.g., blood, urine, etc.). The sample is placed into the fluid chamber where it contacts the functionalized working electrodes on the electrochemical test strip device, which are subjected to potentiometry measurements by an interface device to obtain signals indicative of a presence, absence, or concentration of target analytes in the fluid.

Interface Devices

The interface devices described herein are useful for obtaining and presenting quantitative analog and digital signals generated from electrochemical measurements performed on the electrochemical test strips described above. The interface devices can be used for evaluating results of testing analytes on electrochemical test strip devices and sending test results to an electronic device, such as a smartphone, tablet, or computer, for processing (e.g., to an application executing thereon) and communicating an output to the user. Information flow to the electronic device can be achieved by a wired or wireless protocol system implemented on the interface device and the electronic device or an application executing thereon. The application or electronic device may be configured to provide qualitative (e.g., positive/negative) or quantitative results quickly, saving cost and time when tests need to be performed at a high frequency. In some examples, an interface device for an electrochemical test strip device comprises a cable-based system which can be used in combination with an electronic device.

Various embodiments of the interface device can accept a variety of electrochemical test strips. In some examples, electrochemical test strips that can be accepted include electrochemical biosensor strips with at two chambers with 3 electrodes each, as described herein, but other configurations with one or more than two chambers may be used. In a specific example, an interface device comprises a smart cable having distal and proximal ends; the cable having a slot or port at the distal end, the slot or port capable of receiving an electrochemical test strip device; the cable having an electronic device adapter at the proximal end; a processor, the processor enclosed within the cable, the processor arranged to receive at least electronic signals and power from an electronic device, and the processor capable of generating test results from the electrochemical test strip device. The electronic device may, in some examples, use Artificial intelligence based systems and algorithms to compare raw analog data or digitized analog data to previous test results to a similar demographic profile. In some examples, the algorithm identifies a positive test result when a change in current from baseline is above a preset threshold from the previous test results and a negative test result when the change in current from baseline is below the preset threshold from the previous test results. The interface device may comprise a non-transitory computer readable memory storage device, such as enclosed within the cable. The memory storage device may be capable of storing test results, firmware, or executable instructions, for example. The electronic device may deliver a comparison report from the AI tools back to the user, such as with one or more of a recommendation, a transaction log that provides non-repudiation of the test results, metadata, a public/private key encrypted hash based on an identifier for the electrochemical test strip device, which optionally contains details on the type of test, manufacturing history, timestamp, tester UserID, patient UserID. Optionally, an interface device includes an antenna (e.g., located in the cable in the case of a cable-based interface device), such as an antenna that is capable of or configured to receive and transmit a test result to another electronic device, such as via Bluetooth or other wireless transmission protocol.

Figure 13:
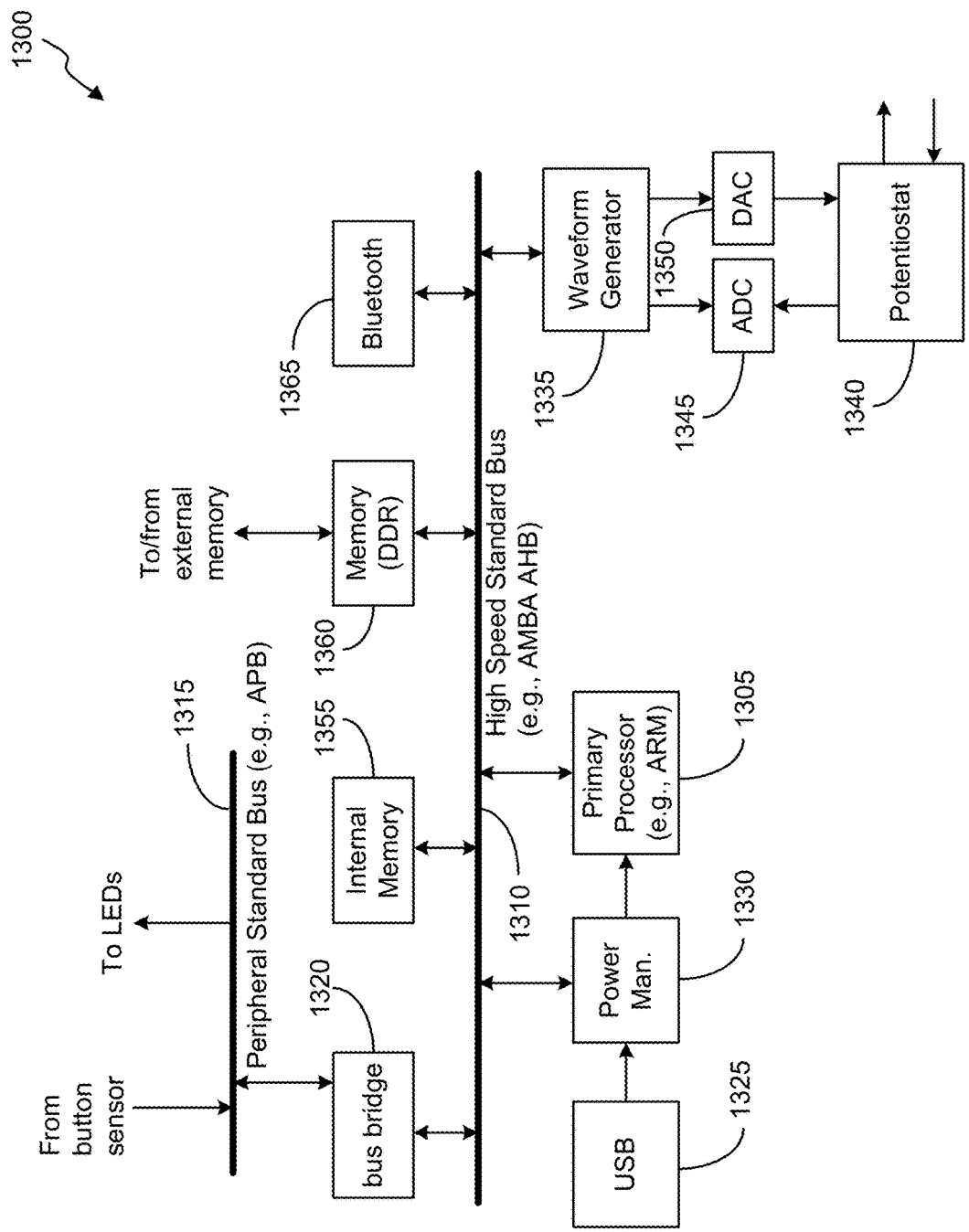
FIG. 13 provides an overview of an example interface device for detecting analytes using an electrochemical test strip device.

FIG. 13 provides an overview of an example interface device 1300 for detecting analytes using an electrochemical test strip device. Interface device 1300 may be constructed as a system on a chip (SoC). Example components of interface device 1300 may include a primary processor 1305, a high speed standard bus 1310, a peripheral standard bus 1315, a bus bridge 1320, a USB controller 1325, a power management unit 1330, a waveform generator 1335, a potentiostat 1340, an analog to digital converter (ADC) 1345, a digital to analog converter (DAC) 1350, internal non-volatile memory 1355, a memory controller 1360 (e.g., for interfacing with external memory), and a Bluetooth controller 1365.

The primary processor 1305 can run firmware or perform operations stored on non-voolatile memory 1355 or another non-transitory computer readable storage medium. For example, the primary processor 1305 can execute a hierarchical state machine. For example, at any given time when there is power, the primary processor 1305 can be booting, executing the state machine, or in a sleep state. In examples, the primary processor 1305 may be powered down and off when not in use. In some examples, power may be provided, such as by connecting a USB cable, which powers up the primary processor 1305 and causes it to execute a quick boot sequence. In one example, the primary processor 1305 obtains firmware from internal memory 1355 and loads it into processor memory for execution. Once the boot sequence completes, the primary processor 1305 can begin running a state machine. In some examples, the state machine has only a few states at the top level: 1) Wait for Command, 2) Process Command, 3) Execute Test. The commands themselves can come from another device connected to the interface device, such as a connected smartphone (e.g., connected by USB or Bluetooth). Optionally, the commands may come from one or more buttons located on or integrated with the interface device 1300. When the primary processor 1305 receives a command, such as from a smartphone or a button, it goes into the Process Command state. In this state, the primary processor 1305 first decodes the command received, and then performs the appropriate operation. There may be a short list of commands available, including Provide Status, Execute Bluetooth Pairing, Run Test, Provide Test Data, and Clear Test Data.

If the command is to Run Test, the primary processor 1305 may proceed into the Execute Test state. Execute Test is itself may be a state machine, such as including the following states: 1) Pre-test Check, 2) Stimulus/Response, 3) Process Data, 4) Indicate Test Result, 5) Send Test Data. These states are described in further detail below.

The operation of the interface device 1300 may be coordinated by the primary processor 1305, which can be a standard, low power, general purpose processor, such as an ARM processor or a similar RISC processors, ready to be compiled into the SoC design. The primary processor 1305 controls the rest of the SoC system, operating a firmware program which implements a hierarchical state machine, as described below. The primary processor communicates 1305 with many of the other components of the SoC using a standard high speed bus 1310, such as AMBA AHB. In embodiments, a standard bus, such as AMBA, is used as many other components may be available and/or designed to work with AMBA.

Advantageously, the bus is high speed to support real time data collection. For example, during the Stimulus/Response portion of Run Test, the ADC 1345 will provide a steady stream of digital results data, which is transmitted via the high speed bus back 1310 to the primary processor 1305. The primary processor 1305 also uses the high speed bus 1310 to communicate with the USB controller 1325, sending data for transmission over USB to the connected smartphone, or receiving commands from the smartphone via USB. Similarly, the primary processor 1305 uses the high speed bus to communicate with the Bluetooth controller 1365. The primary processor 1305 also uses the high speed bus for data transactions with the internal memory 1355, and to interact with the memory controller 1360 for interactions with external memory. Finally, the primary processor 1305 uses the high speed bus 1310 to provide commands to the waveform generator 1335.

The peripheral standard bus 1315 may be implemented as a lower-speed standard bus supporting a few peripherals that do not require the high-bandwidth communication provided by the high speed standard bus 1310. This frees the high speed bus 1310 from needing to deal with those peripherals. A commonly-used standard bus for peripherals is the AMBA Peripherals Bus (APB). Examples of low speed peripherals in this interface device 1300 include LED drivers that control the usage of indicator lights, and button controllers which provide de-bounced signals when buttons are pressed. The bus bridge 1320 manages the interplay between the high speed bus 1310 and the peripherals bus 1315. An example of a bus bridge is the AMBA Bridge, used between AMBA high speed bus and the APB.

The USB controller 1325 can provide functions, including enabling an external electronic device connected to the interface device to provide power through the USB connection. Also, the USB controller 1325 supports data communication between the connected electronic device and the interface device. For this case, the USB controller 1325 translates the data between the format and protocol used on the high speed standard bus 1310 and the serial data and protocol defined by the USB standard.

The power management unit 1330 manages the power state of the interface device 1330. To conserve power, the interface device 1330 can transition into a low power, sleep state after a predefined period of inactivity. The power management unit 1330 can also wake the interface device 1330 back up from the low power state if it receives any interrupts from the bus bridge 1320, the USB controller 1325, or the Bluetooth controller 1365, for example.

The waveform generator 1335 generates digital waveforms representing voltage waveforms that are then sent through the DAC 1350 and to the potentiostat 1340. An example of a digital waveform is the excitation waveform used by square wave voltammetry. This is a digital ramp waveform with a specified start voltage, end voltage, and voltage increment size and duration, with a superimposed square wave. To free the primary processor 1305 from needing to manage all the details of these waveforms, the waveform generator 1335 can include an embedded microcontroller. The primary processor 1305 sends commands to the waveform generator 1335 to indicate the characteristics of the required waveforms, and the waveform generator 1335 can generate the waveforms. In addition to generating the waveforms themselves, which then go through the DAC 1350 on the way to the potentiostat 1340, the waveform generator 1335 can also generate control signals to the ADC 1345 at the output of the potentiostat 1340. These control signals indicate when the ADC 1345 is to take current samples from the potentiostat 1340. The current samples can be synchronized with the stimulus waveform, so that they are taken at the proper times. For example, for square wave voltammetry two current samples at each voltage increment level are obtained: one taken near the end of the high phase of the square wave and one taken near the end of low phase of the square wave.

The potentiostat 1340 may be constructed as analog block including feedback amplifier circuits and precision resistors. The potentiostat 1340 is configured to maintain a fixed voltage between the working electrode and reference electrode on the electrochemical test strip device while measuring current at the working electrode. The potentiostat 1340 connection to the reference electrode may be configured as a very high impedance connection, such that very little current flows from or to the reference electrode. A feedback amplifier may be used to measure the actual potential between the working electrode and the reference electrode and compare it to the desired potential, as specified by the input from DAC 1350 at the output of the waveform generator 1335. For example, the output can provide a correction to keep the potential at the desired level.

The ADC 1345 converts analog current measurements from the potentiostat 1340 to digital values which are then sent to the primary processor 1305. The DAC 1350 converts digital signals coming from the waveform generator 1335 to analog voltage levels for the potentiostat 1340.

Pre-test Check: The Pre-Test Check can be configured as a short sequence of steps to check that the interface device 1300 is set up properly to perform a test. One check is that a test strip is properly inserted into the test strip connector and is properly filled with sample fluid. The primary processor 1305 can perform this step by commanding the waveform generator 1335 to provide a small DC voltage to apply across two of the electrodes on the test strip and then getting the potentiostat 1340 and ADC 1345 to measure the resulting current. The resulting analog current measurement is converted to a DC value by the ADC 1345, and provided back to the primary processor as digital data. If there is no current, or a current much smaller than a threshold, it indicates either that the test strip is not properly inserted, or that the sample chamber on the test strip is not properly filled with fluid. If those conditions are true, the primary processor 1305 can generate a signal indicating an "invalid test" and abort the test, returning back to the Wait for Command state. The signaling of "invalid test" optionally takes different forms. In one example, the primary processor 1305 puts a signal onto the peripheral bus 1315 to specify that an "invalid test indicator" LED is to illuminate. In another example, the primary processor sends an "invalid test" message via the USB controller 1325 or the Bluetooth controller 1365 to a connected electronic device.

Stimulus/Response: In the Stimulus/Response state, the primary processor 1305 provides commands to the waveform generator 1335 and receives data from the ADC 1345 after coming through the potentiostat 1340. Different electrochemical stimulus/response patterns are possible. For example, one stimulus/response approach is called square wave voltammetry. In that approach, the waveform generator 1335 is instructed to provide a digital voltage ramp, from a specified starting voltage to ending voltage and with a specified step size. Superimposed on top of that ramp, the waveform generator 1335 provides a square wave whose period coincides with the duration of each voltage step of the ramp. The pattern is fed into the potentiostat 1340, via the DAC 1350, and the potentiostat 1340 applies this pattern as a set of voltage levels between the working electrode and reference electrode of the connected electrochemical test strip device. The potentiostat 1340 can make two current measurements at each voltage increment, one at the top of the square wave and one at the bottom. Those current measurements feedback through the ADC 1345 to the primary processor 1305, where they are stored as digital results data in internal memory 1335.

In the Process Data state, the primary processor 1305 runs an analysis algorithm on the collected test data to determine a test result. In some examples, this analysis includes identifying peaks in the data, within specific ranges, assessing their amplitudes, comparing to other peaks and/or to thresholds, and filtering out noise. For examples where there is a separate measurement chamber for reference, the data from the reference chamber are compared to that from the test chamber. If the analysis determines that the results are above certain thresholds, the test is considered positive. On the other hand, if the results are aligned with expectations and within thresholds for a negative, then the test is considered negative. If neither of those is true, the test may be considered invalid.

The Indicate Test Result state is used to communicate the test result. The communicate can occur in a variety of fashions. For example, the interface device 1300 can provide a visual test result, such as by illuminating an LED light or generating a display on a display device (where included in interface device). In other examples, interface device 1300 transmits the test result to a connected electronic device using the USB controller 1325 or the Bluetooth controller 1365.

In the Send Test Data state, the primary processor 1305 sends the digital form of the raw test data to the connected electronic device via USB or Bluetooth, for example. The Run Test state machine can optionally be configured to automatically send the raw data after each test is performed. In other configurations, the primary processor 1305 sends the raw data only when requested, using the Provide Test Data command.

Figure 14:
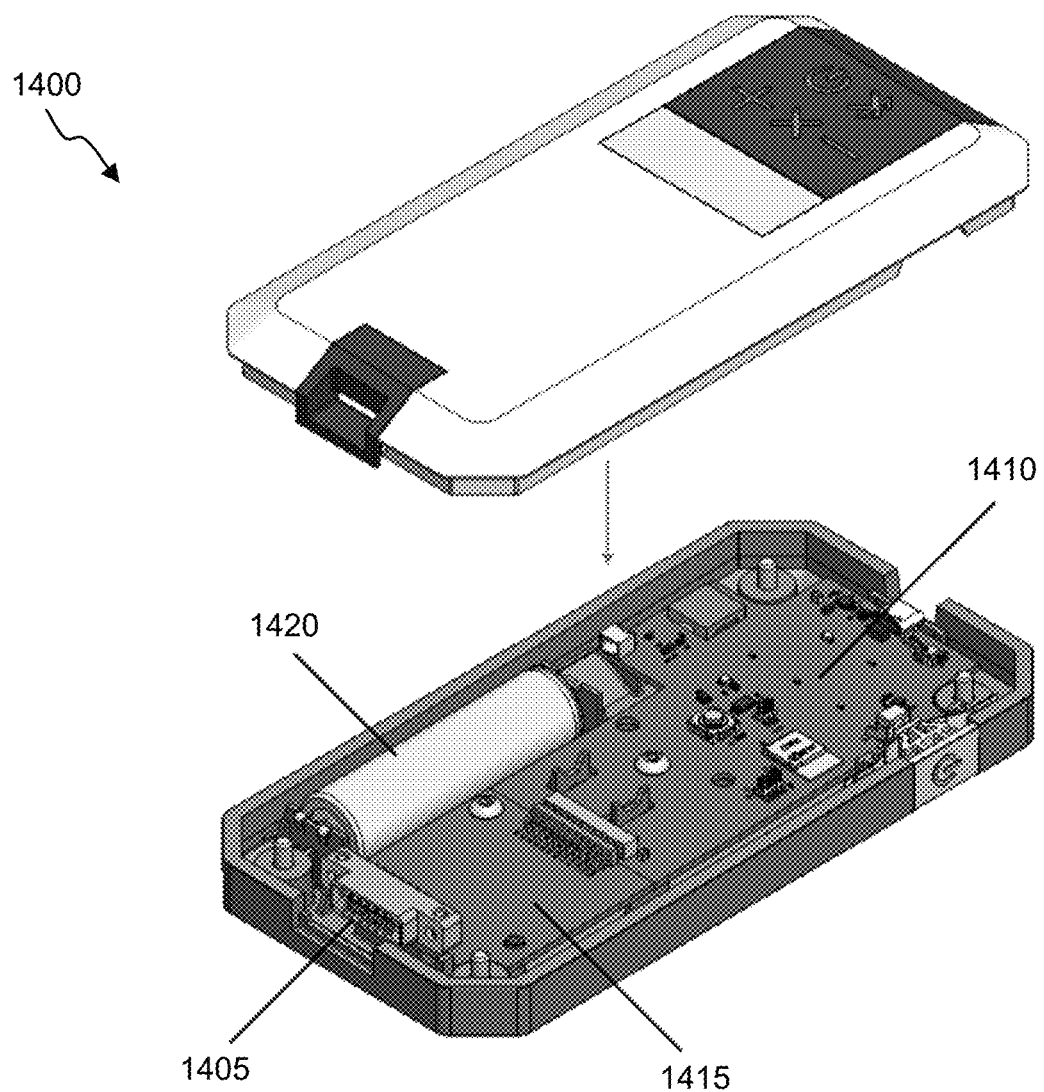
FIG. 14 shows an illustration of an example handheld interface device.

FIG. 14 shows an illustration of an example handheld interface device 1400.

Electrochemical test strip devices may be connected to electrode contacts 1405, accessible from a port at the edge of handheld interface device 1400. With the top cover removed, the main circuit board 1410 is visible, as is analog board 1415 and battery 1420. The main circuit board can include a general purpose microcontroller unit with Bluetooth capability, power management, memory, light emitting diode (LED) drivers, and switch/button inputs. The analog board 1415 can include potentiostat capabilities (sensitive analog measurement components with precise voltage control), waveform generator, ADCs and DACs, multiplexor circuits, temperature sensors, or the like.

Figure 15A:
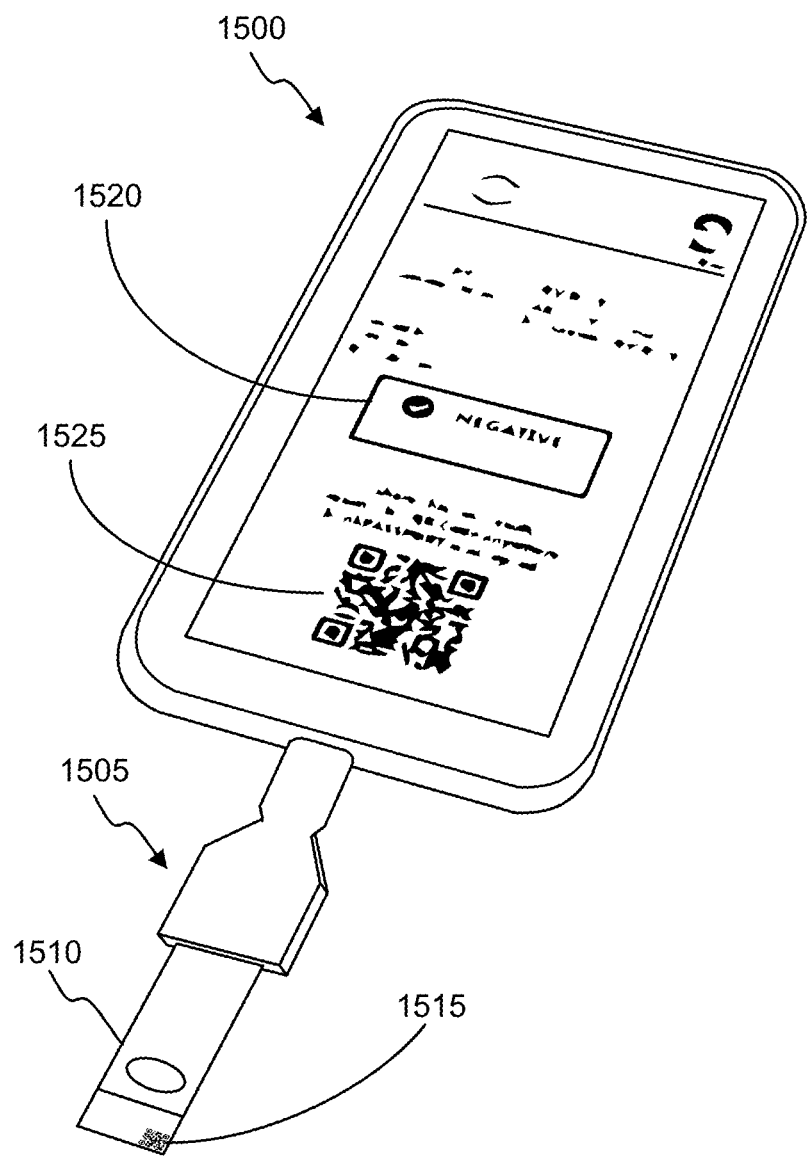
FIG. 15A and FIG. 15B show illustrations of a mobile electronic device with an interface device connected to a port of the mobile electronic device. The interface device is depicted as an adapter-format test strip reader in FIG. 15A and as a cable-based test strip reader in FIG. 15B.
Figure 15B:
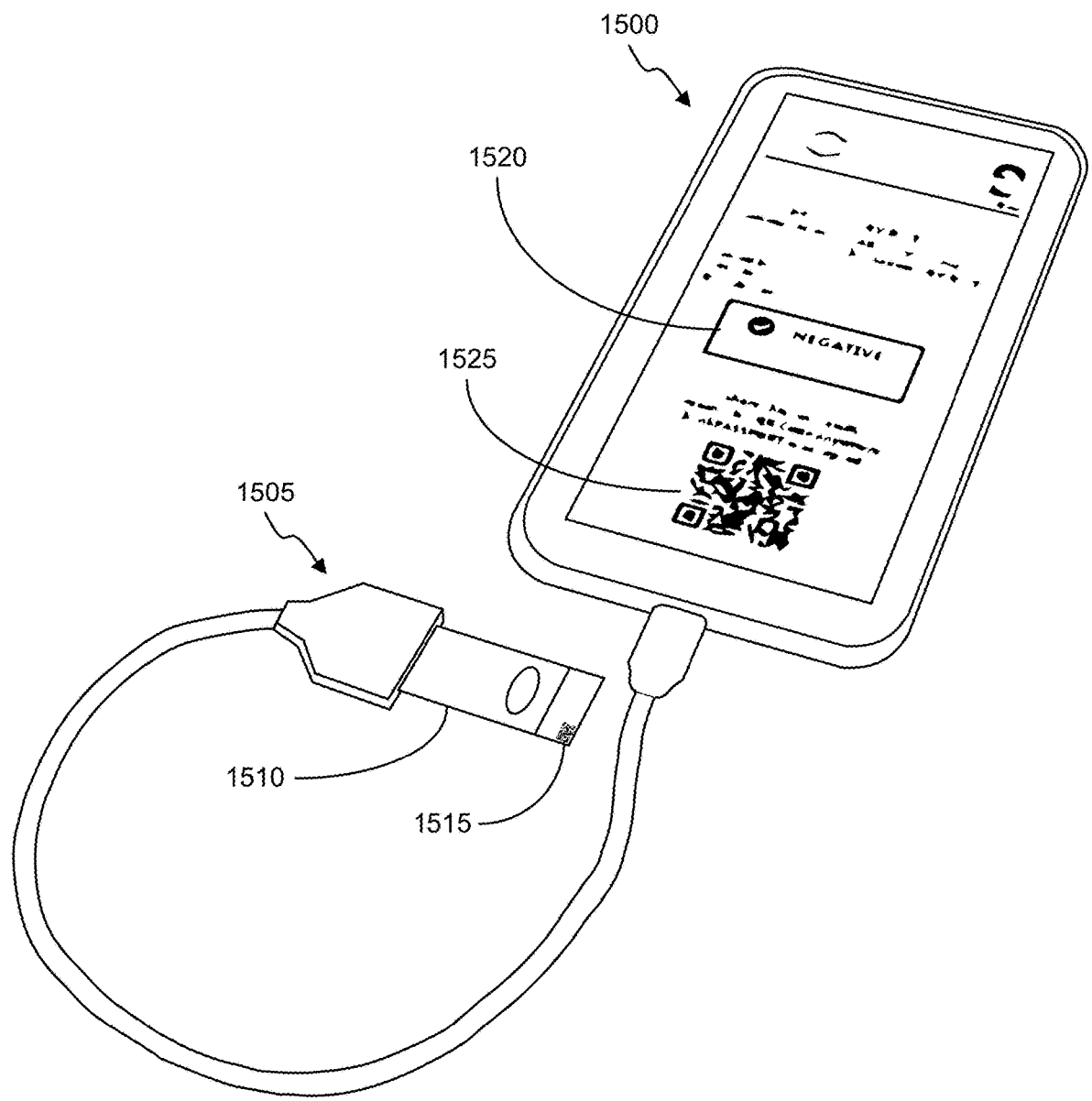

FIG. 15A and FIG. 15B show illustrations of a mobile electronic device 1500, such as a smartphone, with an interface device 1505 connected to a port of the mobile electronic device 1500. Interface device 1505 is depicted as an adapter-format test strip reader in FIG. 15A and as a cable-based test strip reader in FIG. 15B (e.g., a Smart Cable). An electrochemical test strip device 1510 is shown inserted into a port of the interface device 1505, to allow for an electrochemical antigen detection assay to be performed, such as using potentiostatic measurements obtained using components integrated in interface device 1505. Advantageously, mobile electronic device 1500 can include a camera or other input device to allow for reading or input of a barcode or identifier 1515 that may be present on electrochemical test strip device 1510. Mobile electronic device 1500 can include a display that can provide a test result 1520 or provide another barcode 1525 that can be used to identify a particular sample and/or the test result.

Figure 16:
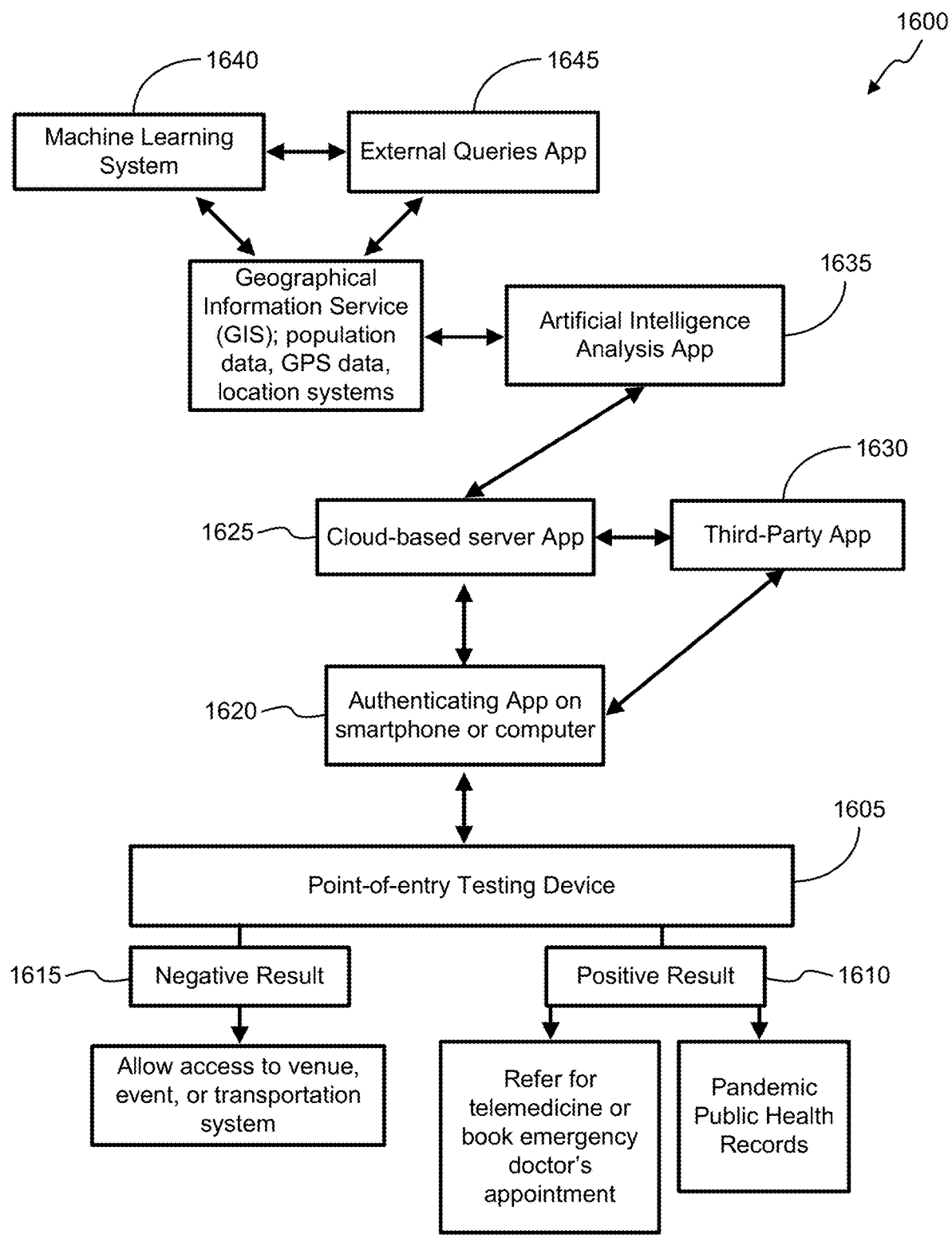
FIG. 16 provides an overview of a wide-scale pandemic Real-Time Testing System (RTTS).

FIG. 16 provides an overview of a wide-scale pandemic Real-Time Testing System (RTTS) 1600, which can be used with electrochemical biosensor rapid antigen assays and electrochemical test strip devices described herein and used for real-time screening for entry into venues, events, transportation systems, or the like. The RTTS 1600 includes a Point-of-Entry Testing Device 1605, which can be used to obtain test results or screening results for an infectious disease (e.g., infection by SARS-CoV-2) or vaccination or prior infection by an infectious disease. RTTS 1600 can employ an electrochemical test strip device, as described herein, for device 1605 used for screening. In the case of a positive result 1610 of screening (e.g., indicating infection by SARS-CoV-2), nonaccess to the venue, event, or transportation system is triggered by RTTS 1600. In the case of a negative result 1615 of screening (e.g., indicating non-infection by SARS-CoV-2), access to the venue, event, or transportation system is triggered by RTTS 1600. Access to the venue, event, or transportation system can, in some cases can be electronically permitted or restricted by an access device (e.g., a locking door, turnstile, etc.) or by displaying an audible or visible indicator for use by an usher to permit or deny access to the venue, event, or transportation system.

In some examples, an authenticating application (App) 1620 is executed on a smartphone or computer, which may be connected to the Point-of-Entry Testing Device 1605 by wired connector or wireless means (such as, but not limited to, Bluetooth and WiFi). The authenticating App 1620 may be configured to use government identification (e.g., driver license, passport, identity card, etc.), biometric scan (e.g., fingerprint, voice print, facial recognition, etc.), or other way for verifying identity of an individual testee or association with a test result for an electrochemical biosensor rapid antigen assay. A cloud-based server App 1625, stores information from a database, including, but not limited to, Testee ID, Testee results, Testee Site, time and date stamp and GPS data; the cloud-based Server App is further capable of interacting with Third-Party apps 1630, such as for the purpose of providing a Digital Results Badge of the results (structured in typical formats including but not limited to HTML, CSV, text, and Excel) for authenticating Testee at sites other than the original Point-of-Entry device. The Artificial Intelligence analysis app 1635, can integrate data from the cloud-based Server App 1625 and apps for Geographical Information Services (GIS), and population data, GPS data, and location systems. The machine learning system 1640 or Artificial Intelligence Analysis App 1635 and associated algorithms can interpret data in real-time to provide confidence intervals and learn from past trends to make predictions on future outcomes, which may be referred to as a a Real-Time Processing System (RTPS). External Queries App 1645, is the human (for example but not limited to Web page or Smartphone App) and computer interface (for example but not limited to an Application Programming Interface aka API) allowing the Real-Time Testing System 1600 to be interrogated and data downloaded.

Methods of Generating and Using Test Results

Figure 17:
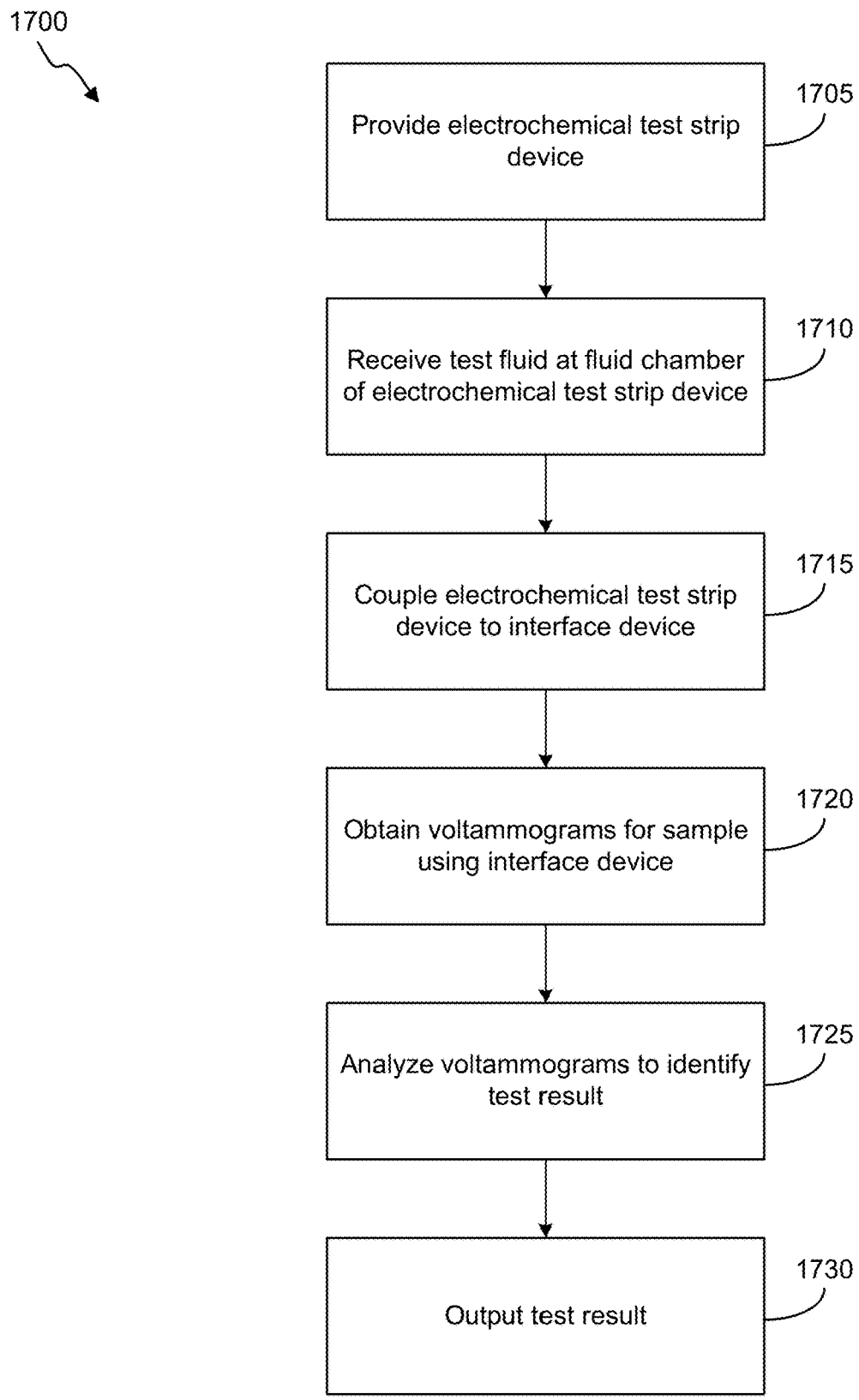
FIG. 17 provides an overview of an example method of generating test results using an electrochemical test strip device and interface device.

FIG. 17 provides an overview of an example method 1700 of generating and using test results using the electrochemical test strip devices and interface devices described herein. At block 1705, an electrochemical test strip is provided. The electrochemical test strip may be any suitable electrochemical test strip described herein. In examples, the electrochemical test strip is functionalized with a capture molecule suitable for binding a particular analyte of interest. For example, in the case of determining infection by SARS-CoV-2 or a SARS-CoV-2 variant, the capture molecule may comprise an antibody that binds a SARS-CoV-2 or SARS-CoV-2 variant structural protein (e.g., spike protein, nucleocapsid protein, envelope protein). Optionally, the capture molecule may comprise an antibody that binds a biomarker indicative of infection by SARS-CoV-2 or a SARS-CoV-2 variant (e.g., an inflammatory biomarker). In the case of determining prior infection by SARS-CoV-2 or a SARS-CoV-2 variant or immunity against SARS-CoV-2, the capture molecules may comprise a viral structural protein or a portion thereof that binds anti-SARS-CoV-2 antibodies or anti-SARS-CoV-2 variant antibodies.

At block 1710, a test fluid is received at the fluid chamber(s) of the electrochemical test strip device. The test fluid may comprise any suitable fluid that may contain the analyte of interest, such as saliva or blood. Other body fluids may be used. In addition, other fluids may be useful as test fluids, such as environmental fluids, depending on the particular test being administered using the electrochemical test strip device.

At block 1715, the electrochemical test strip device may be coupled to an interface device, such as to put electrode contacts of the interface device into electrical communication with electrodes of the electrochemical test strip device. In some examples, the interface device, or an associated electronic device (e.g., smartphone, tablet, computing device, etc.) may receive input identifying information about the electrochemical test strip device. In some examples, the electrochemical test strip device may include a barcode or other identifier that is scanned by an input component of the interface device or electronic device. The barcode or other identifier may identify information about functionalization of the electrochemical test strip device, about manufacturing of the electrochemical test strip device (e.g., a batch number), or the like. In some cases, the electrochemical test strip device may include this or other identifying information on a wirelessly readable tag or chip (e.g., a near-field communication (NFC) or radio frequency identification (RFID) tag or chip), and the interface device or the electronic device may wirelessly obtain the information.

At block 1720, the interface device may perform potentiostatic measurements on the electrochemical test strip device, such as by applying one or more voltages to electrodes of the electrochemical test strip device to obtain current measurements or otherwise determine voltammograms. Voltammograms are useful as metrics indicating binding of analytes in the test fluid to the capture molecules on the surface of working electrode(s) of the electrochemical test strip device.

At block 1725, the voltammograms or other output from the potentiostatic measurements obtained on the electrochemical test strip device using the interface device may be analyzed to identify or determine a test result. The analysis may include performing a differential analysis, such as based on an reference set of electrodes and a test set of electrodes of the electrochemical test strip device. In some examples, the reference set of electrodes may include a working electrode functionalized with capture molecules that do not bind the target analyte or that bind a different analyte, while the test set of electrodes may include a working electrode functionalized with capture molecules that do bind the target analyte. In some examples, by using differential measurements, background signals can be removed increasing the sensitivity of the test for the target analyte.

In some examples, analyzing the voltammograms may include using artificial intelligence or machine learning to generate the test result. For example the voltammograms may be used as input into a trained machine learning model comprising a set of parameters that were learned using test voltammograms associated with detection of known quantities of the same or other target analytes and functions configured to transform the input voltammograms to the test results based on the set of learned parameters. In some cases, the machine learning parameters or functions can be updated over time to generate improved test results as the machine learning model is improved. In some cases, machine-learning models of this nature may be useful for determining qualitative or quantitative measurement metrics of target analytes, such as target analytes that may be difficult to differentiate. For example, machine learning models may be useful for distinguishing between infection by different SARS-CoV-2 variants based on determined patterns of how these variants may bind to specific capture molecules or sets of capture molecules, such as different host proteins (e.g., ACE-2) or antibodies (e.g., anti-SARS-CoV-2 spike protein antibodies, anti-SARS-CoV-2 nucleocapsid protein antibodies, or anti-SARS-CoV-2 envelope protein antibodies). In another example, machine learning models may be useful for distinguishing between natural and vaccine-induced immunity to SARS-CoV-2 or SARS-CoV-2 variants based on patterns of how antibodies present in a test fluid bind to capture molecules or sets of capture molecules, such as different SARS-CoV-2 structural proteins or components thereof. In another example, machine learning models may be useful for determining when or if a vaccine booster is needed based on patterns of antibody levels and immunity challenge results.

At block 1730, the test results may be output, such as by an output device (e.g., LEDs or a display) on the interface device or on a display of an electronic device (e.g., smartphone or other computing device). The test results may indicate a qualitative or quantitative measure of the presence of the target analyte or other information, such as immunity status or vaccination status. Such information may optionally be used for other aspects, such as to control access to a venue, event, or transportation system, such as where access is controlled based on infection or immunity status. In some examples, a test result may indicate an infection or non-infection status by SARS-CoV-2 or a SARS-CoV-2 variant or an immunity status against SARS-CoV-2 or a SARS-CoV-2 variant. For situations where access to only non-infected or immune individuals is controlled, outputting the test result may allow ushers or access control systems to permit or deny entry to individuals as appropriate.

Although not depicted in FIG. 17, method 1700 may further comprise analyzing the test results. As will be described in further detail below, analyzing test results can be useful for determine compliance with or adherence to treatment regimen. In some cases analyzing test results can involve artificial intelligence or machine learning to get additional information. In the case of test results corresponding to infection by SARS-CoV-2 or a SARS-CoV-2 variant, analyzing the test results using machine learning models may allow for identification of above baseline incidence of infection in a particular geographic location or determining predicted future incidence. Optionally, the test results may be input into a machine learning model, optionally with aggregated test results obtained using other testing systems.

Figure 18:
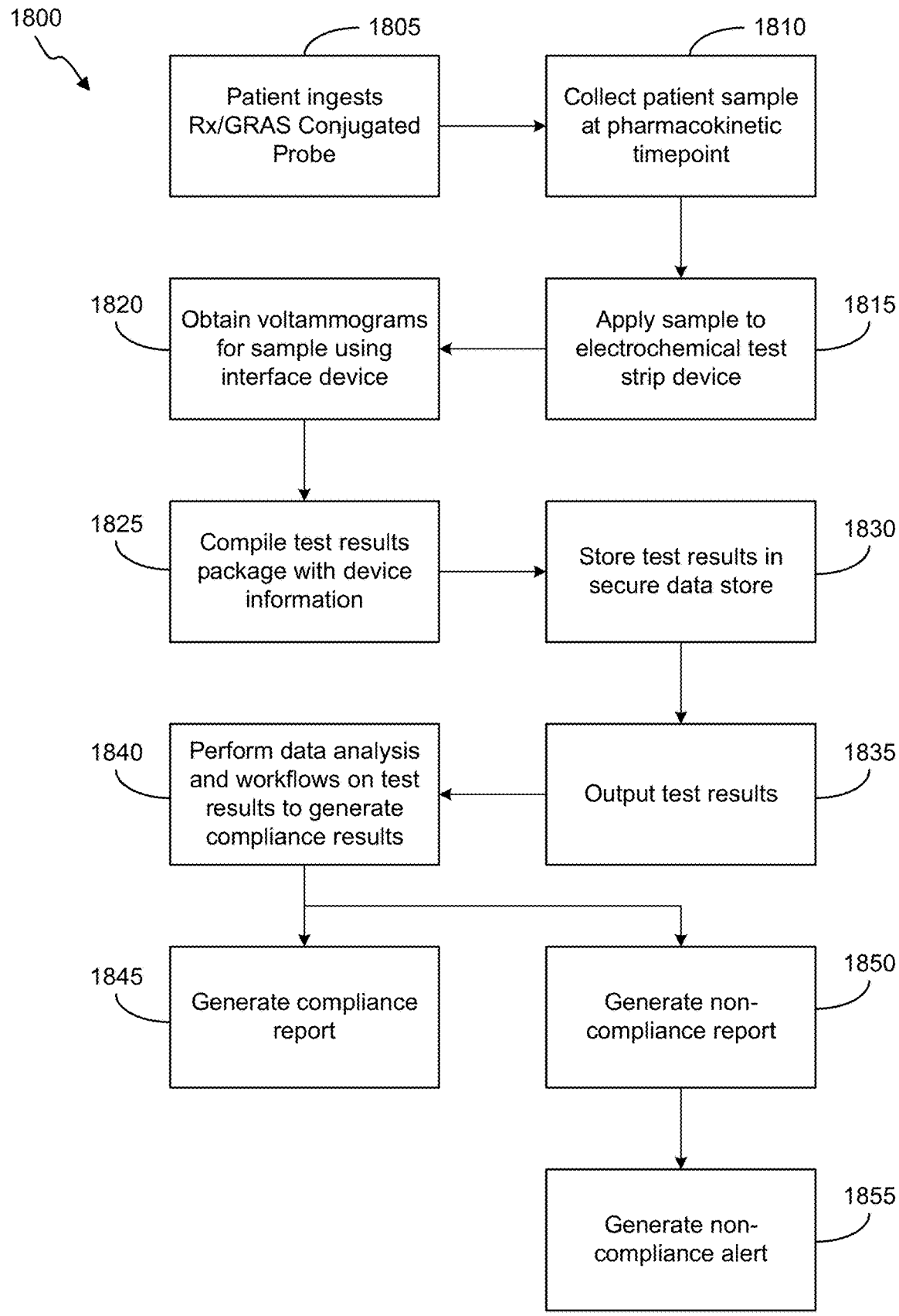
FIG. 18 provides an overview of an example method for compliance monitoring of pharmaceutical administration.

FIG. 18 provides an overview of an example method 1800 of generating and using test results for pharmaceutical compliance or adherence monitoring. Such methods may be useful for determining whether a patient is appropriately administering or being administered pharmaceuticals. In some examples, compliance monitoring may be useful in a clinical trial, allowing close monitoring of the ingestion of pharmaceuticals At block 1805 a patient ingests a therapeutic-generally recognized as safe (GRAS) conjugate. As an example, a GRAS molecule may be propylene glycol. When propylene glycol is included as a GRAS molecule in a therapeutic-GRAS conjugate, propylene glycol can be excreted through the urine within 1-1.5 hours, for example.

A sample from the patient (e.g., urine) can be collected at a suitable pharmacokinetic time point at block 1810 and applied to a functionalized electrochemical test strip device at block 1815 and voltammograms for the sample can be obtained at block 1820 using a suitable interface device. In the case of propylene glycol, glycerol dehydrogenase (GDH) can be immobilized on the gold electrode of the electrochemical test strip device, such as using click chemistry techniques, as described above. NAD+ may be added to the sample before introducing to the fluid chamber of the electrochemical test strip device. GDH may catalyze conversion of propylene glycol to acetol, with an associated change in pH, causing a change in the potentiostatic current, indicating the presence of propylene glycol.

At block 1825, the voltammograms are analyzed to generate a test result, which optionally may be compiled and packaged with other information, such as device information (e.g., electrochemical test strip information, interface device information, etc.), facility or administrator information, location information, timestamp information, and/or patient information (e.g., patient identifier, patient biometric data, etc.). At block 1830, the test results may be stored in a data storage device, which may be secured or encrypted. In some examples, the data storage device may be remote from the interface device and an associated mobile electronic device. Depending on the particular circumstance, the test results may optionally be output at block 1835, such as on a display of the mobile electronic device or using an output component (e.g., LEDs, display, etc.) of interface device. In some cases, outputting the test results may comprise transmitting the test results to a remote location, such as to a medical provider or an electronic health record.

To evaluate the test results for compliance with a treatment regimen, data analysis and workflows may be performed on the test results at block 1840. This may include using artificial intelligence or machine learning algorithms on the test results and/or the voltammograms. The workflow algorithms may analyze location and timestamp information, for example, to compare with defined rules to identify potential non-compliance.

When compliance is determined (e.g., corresponding to a positive test result), method 1800 may proceed to block 1845, where a compliance report is generated. The compliance report may include test result information and other information, such as device information (e.g., electrochemical test strip information, interface device information, etc.), facility or administrator information, location information, timestamp information, and/or patient information (e.g., patient identifier, patient biometric data, etc.). In the case of a clinical trial, the compliance report may be output for use by a clinical trial coordinator or administrator. In this or other cases, the compliance report may be output for use by the patient, a health care provider, or a family member or other caregiver.

When non-compliance is determined (e.g., corresponding to a negative test result), method 1800 may proceed to block 1850, where a non-compliance report is generated. The non-compliance report may include test result information and other information, such as device information (e.g., electrochemical test strip information, interface device information, etc.), facility or administrator information, location information, timestamp information, and/or patient information (e.g., patient identifier, patient biometric data, etc.). In the case of a clinical trial, the non-compliance report may be output for use by a clinical trial coordinator or administrator. In this or other cases, the non-compliance report may be output for use by the patient, a health care provider, or a family member or other caregiver. Optionally, method 1800 may further proceed to block 1855 where a non-compliance alert may be generated. Such an alert may be important for quickly informing the clinical trial coordinator, the patient, the health care provider, or the family member or caregiver that the patient did not administer or was not administered the pharmaceutical or did not administer or was not administered the pharmaceutical at an appropriate time.

Electrochemical Test Data and Results

Figure 19A:
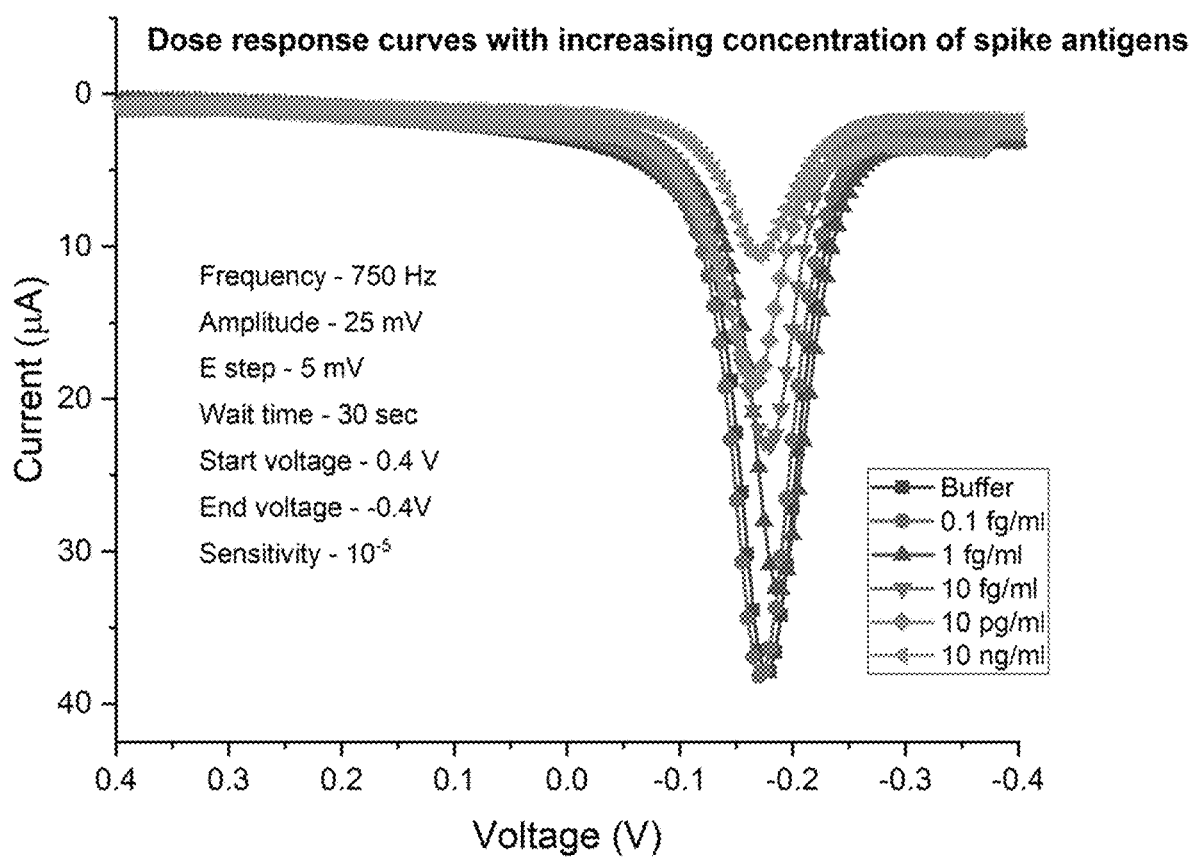
FIG. 19A provides voltammogram data obtained using an electrochemical test strip device functionalized with SARS-CoV-2 S1 monoclonal antibodies as capture molecules.

FIG. 19A provides voltammogram data obtained using an electrochemical test strip device functionalized with SARS-CoV-2 S1 monoclonal antibodies as capture molecules when exposed to test fluids containing no (e.g., only buffer) and varying concentrations of recombinant SARS-CoV-2 S1+S2 ECD spike antigens. The data shows a change in measured current outputs and indicates that, as the concentration of the antigens increases, the current output decreases.

Figure 19B:
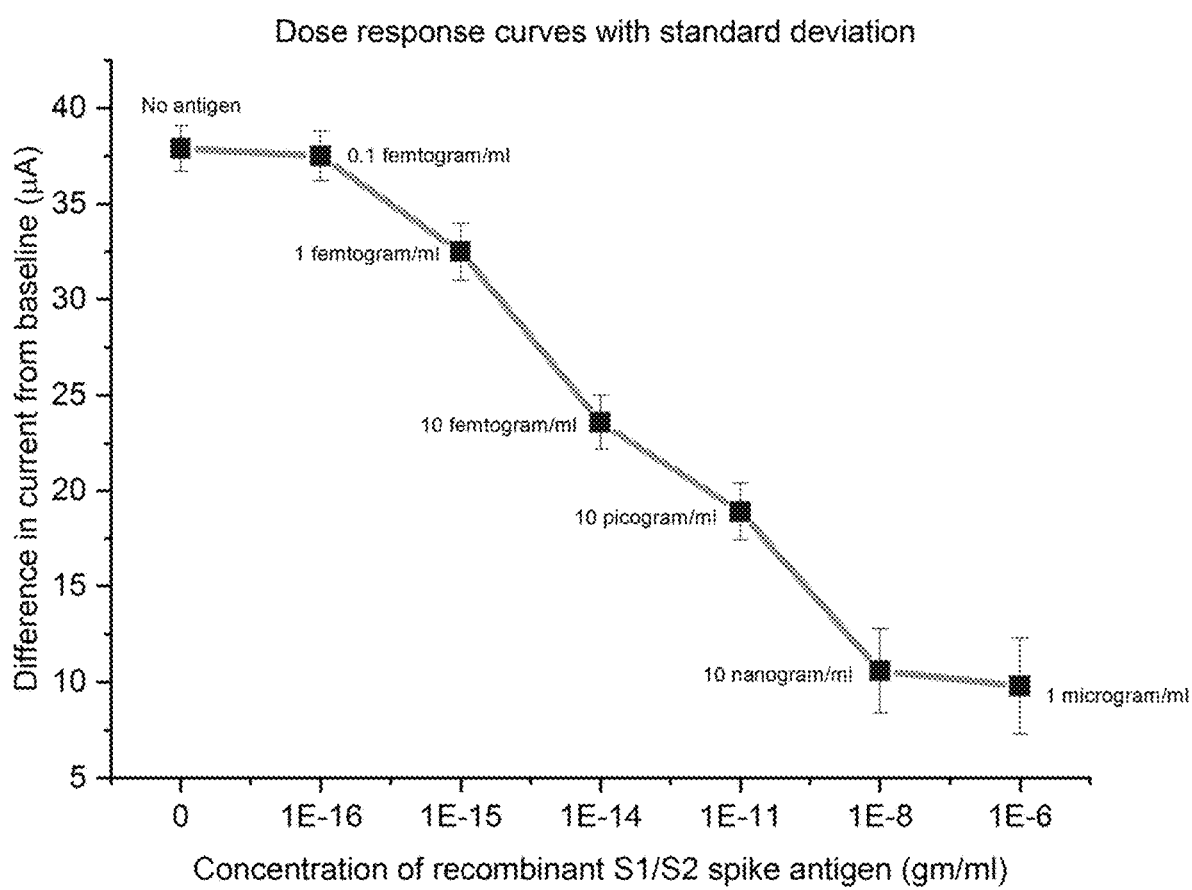
FIG. 19B provides a dose response curve when the immobilized S1 monoclonal antibody was tested against recombinant S1+S2 ECD spike antigens.

FIG. 19B provides a dose response curve with standard deviations when the immobilized S1 monoclonal antibody was tested against recombinant S1+S2 ECD spike antigens. Square Wave Voltammetry confirms change in current signal with a limit of detection (LOD) as low as 1 femtogram per milliliter of the antigen and a dynamic range of 1 femtogram/ml to 10 nanogram/ml.

Figure 20:
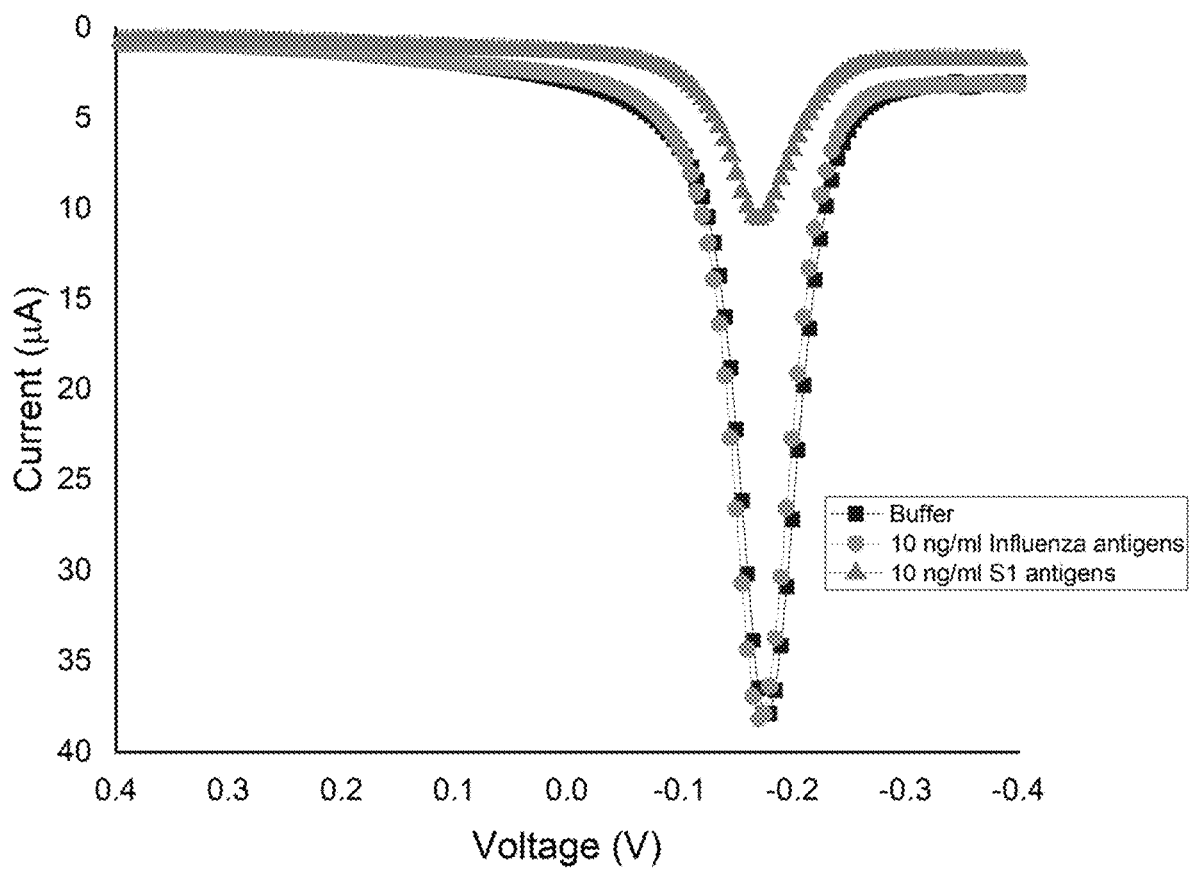
FIG. 20 provides voltammogram quinone, anthraquinone, an anthracycline, daunomycin, doxorubicin, a viologen, a phenothiazine, thionine, malachite green, 2,2'-bipyridine-4,4'-dicarboxylic acid, 1,3-diaza-2-oxophenothiazine, a tricyclic cytosine analog, a quinoxaline derivatives, echinomycin, or any combination of these.

FIG. 20 provides voltammogram data obtained using an electrochemical test strip device functionalized with SARS-CoV-2 antibodies as capture molecules tested against SARS-CoV-2 spike antigens vs influenza neuraminidase antigens as test analytes. The results show specificity of the test to SARS-CoV-2 spike antigens vs influenza neuraminidase antigens. In the case of the influenza antigens, there was no observed change in signal as compared to a buffer solution, while the SARS-CoV-2 antigens caused a decrease in signal, exhibiting specificity of the functionalized electrochemical test strip for testing for SARS-CoV-2.

Figure 21A:
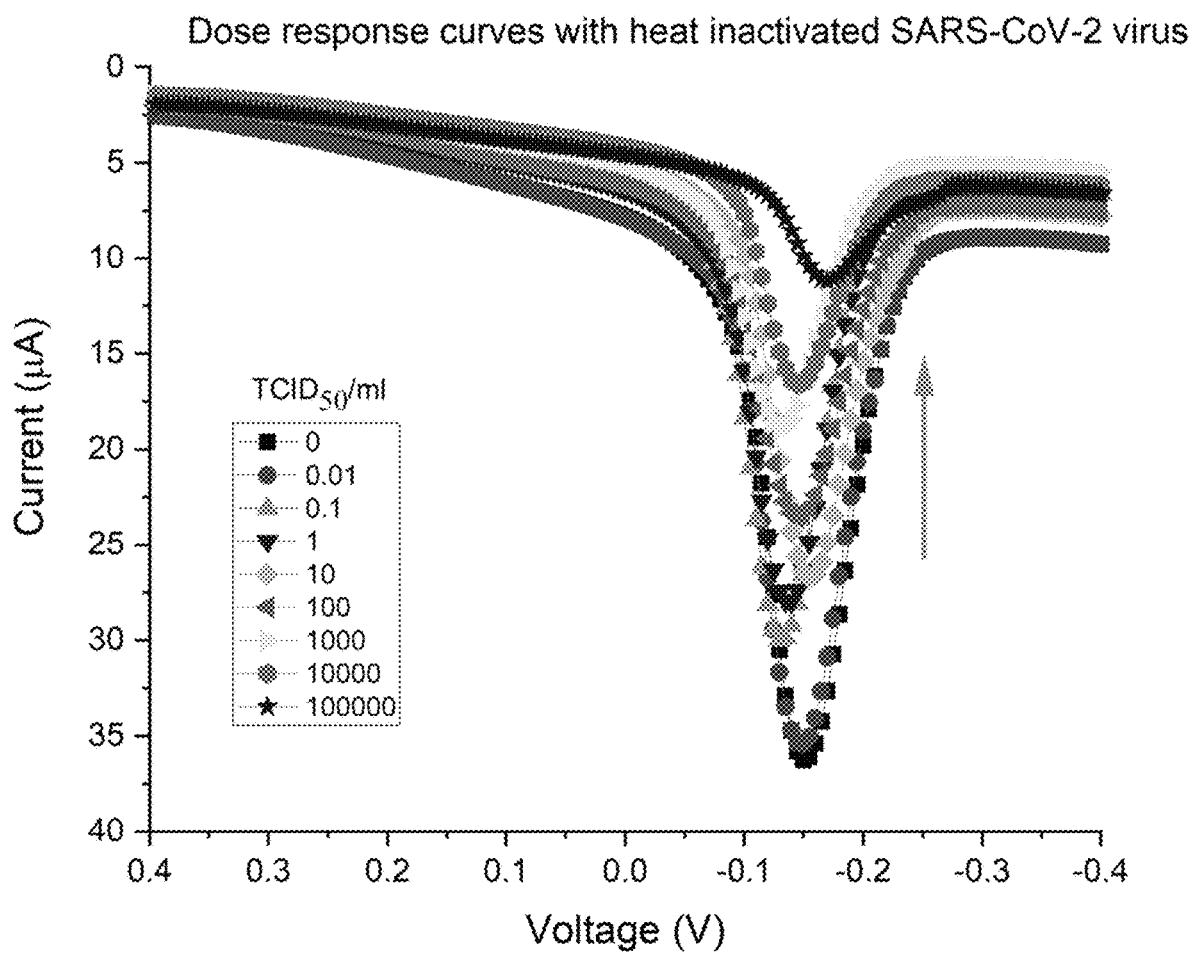

FIG. 21A provides voltammogram data obtained using an electrochemical test strip device functionalized with SARS-CoV-2 S1 monoclonal antibodies as capture molecules tested against heat inactivated viruses (2019-nCoV/USA/WA1/2020) in buffer, showing variations in current outputs for different concentrations of the heat inactivated viruses. As the concentration of the heat inactivated virus increases, the current output decreases. Initial testing using recombinant S1/S2 antigen fragments in buffer indicated a quantitative testing window with saturation but no hook effect, which was confirmed using heat inactivated virus.

Figure 21B:
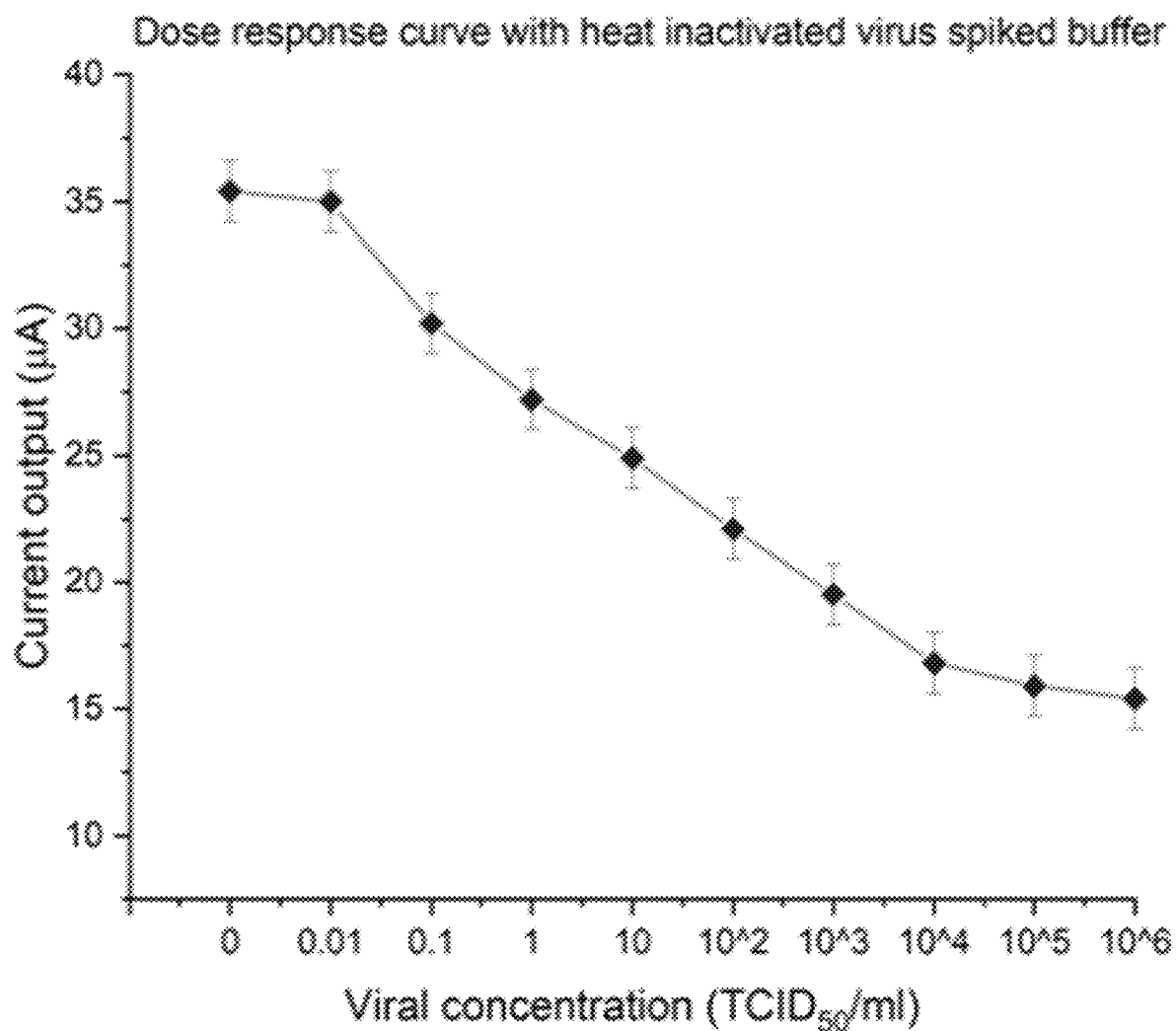

FIG. 21B provides a dose response curve with standard deviations when the immobilized S1 monoclonal antibody was tested against wild-type heat inactivated viruses in buffer. The results confirm the change in current signal, with a limit of detection (LOD) as low as 0.1 TCID50/ml.

Figure 22:
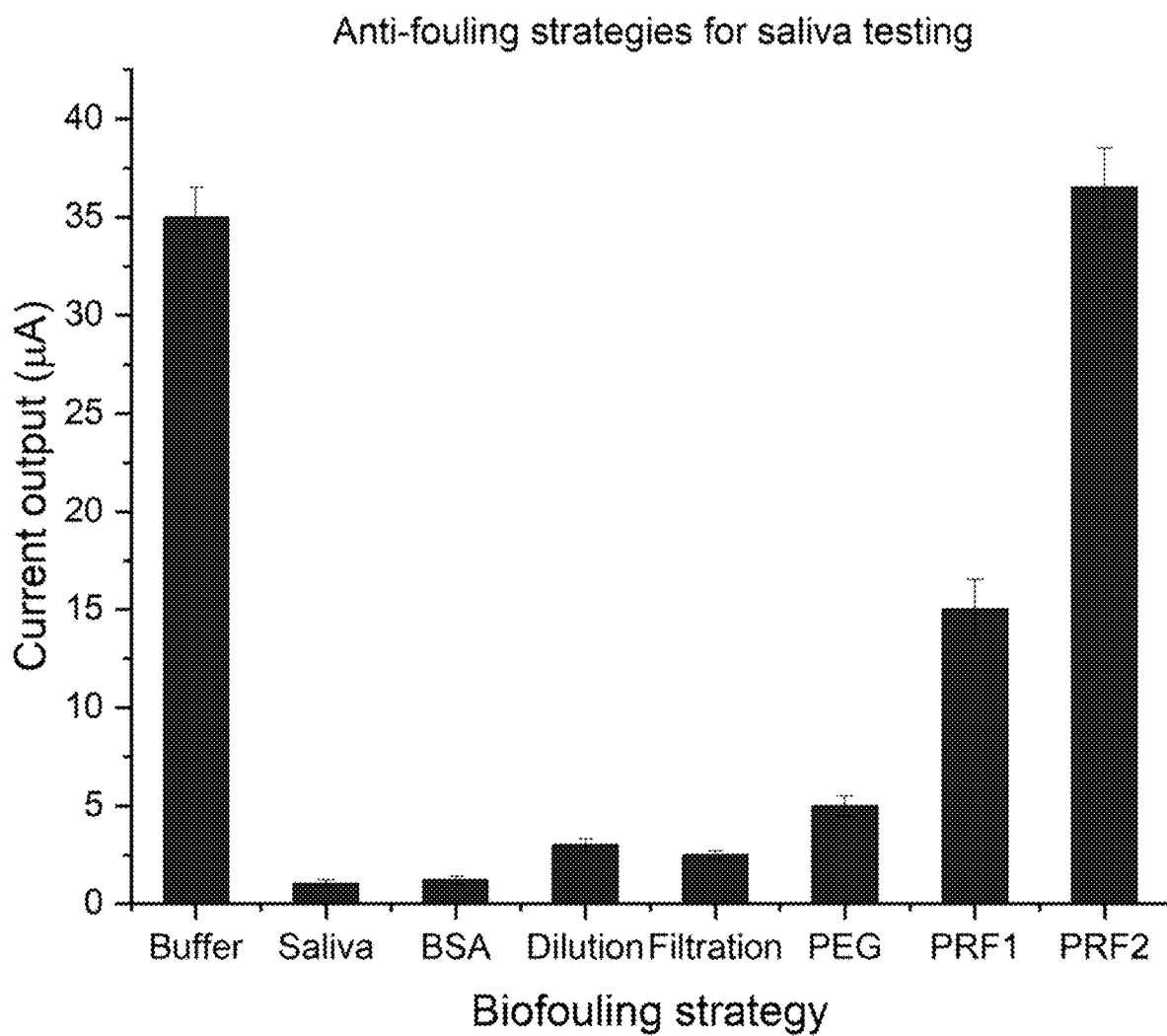

FIG. 22 provides data showing the current output obtained using an electrochemical test strip functionalized with an active capture molecule and tested using saliva as a test fluid with buffer solution as a reference. Compared to buffer solution, saliva reduced the detected current output as though high concentration of a binding analyte were present, and these results were attributed to biofouling by nonspecific analytes (e.g., mucins and amylases) in the saliva sample. Different strategies were evaluated to for preventing electrode biofouling, including coating the working electrode surface with additional anti-fouling agents or using other anti-fouling techniques. Bovine serum albumin was reported in literature as an anti-fouling agent but did not show effective results in saliva. Dilution of the saliva did not produce good current output and the effect of electrode fouling was seen in less than 2 minutes. Starch filtration removed the amylases but had no effect on mucins. Using PEG layers provided a current output which was significantly smaller when compared to baseline signal generated in the presence of a buffer. PRF1 consisting of recombinant PRG4 (rPRG4) and neutral PEG layers provided an increase in current output in the presence of saliva but was not successful in regaining the baseline current output. PRF2 consisting of recombinant proteoglycan 4 (PRG4) and negatively charged PEG layers provided a comparable current output in the presence of both buffer and saliva.

Figure 23:
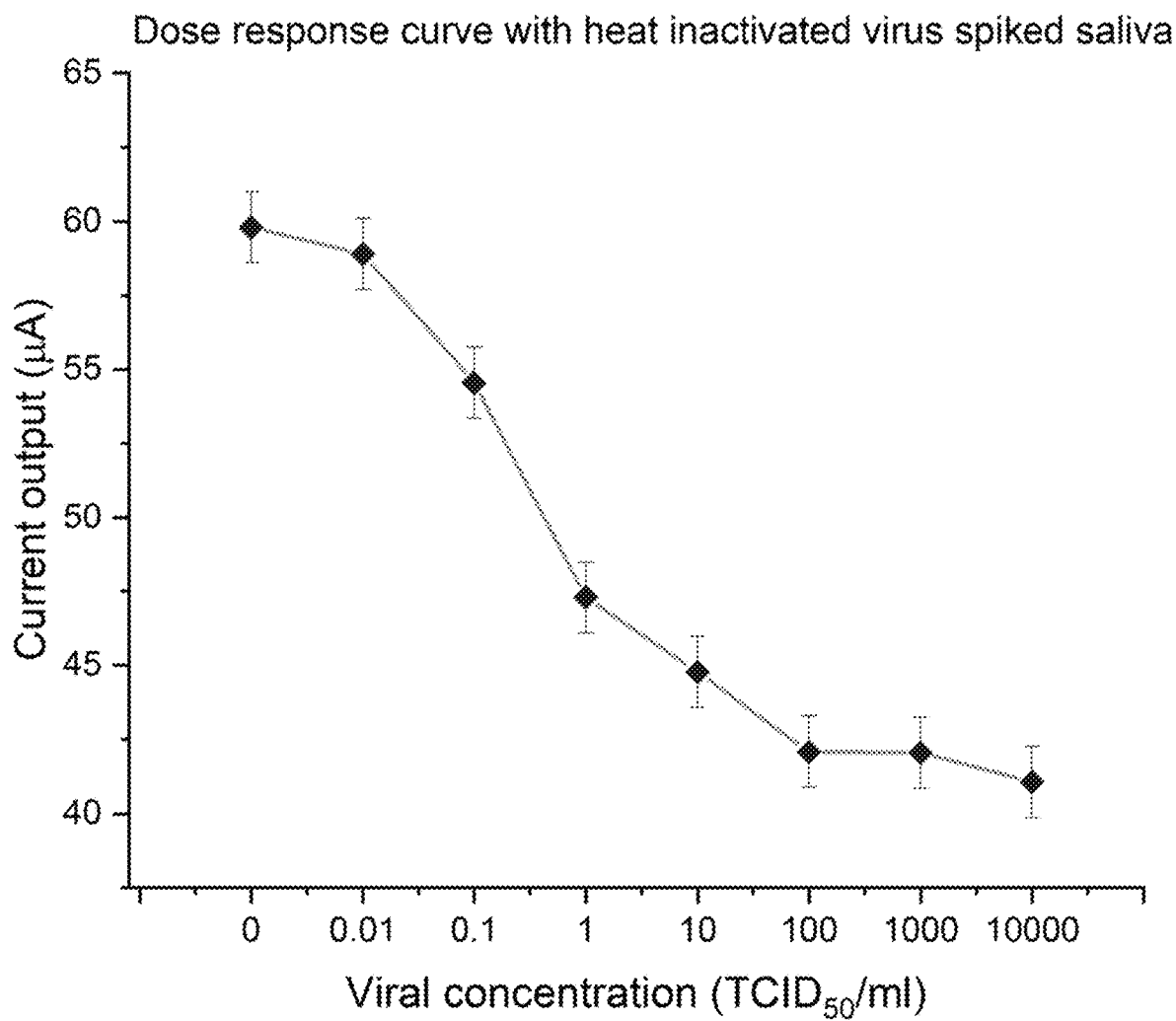

FIG. 23 provides data showing the current output with increasing concentrations of heat inactivated virus in pooled saliva when using electrochemical test strips modified with PRF2. From the data, it can be determined that the LOD is about 0.1 $TCID_{50}$/ml and the highest quantifiable concentration at saturation is 100 $TCID_{50}$/ml, thereby producing a 3-log quantification range. To compare the LOD from this technique with that of standard rapid antigen tests, BD Veritor Plus Analyzer and BinaxNOW COVID-19 Ag Card have an estimated limit of detection at 140 $TCID_{50}$/ml. The FDA cleared BioFire Respiratory Panel 2.1 PCR test has a SARS-CoV-2 LOD for heat-inactivated virus (WA1/2020) of $6.9 \times 10^{-2}$ $TCID_{50}$/ml.

Figure 24:
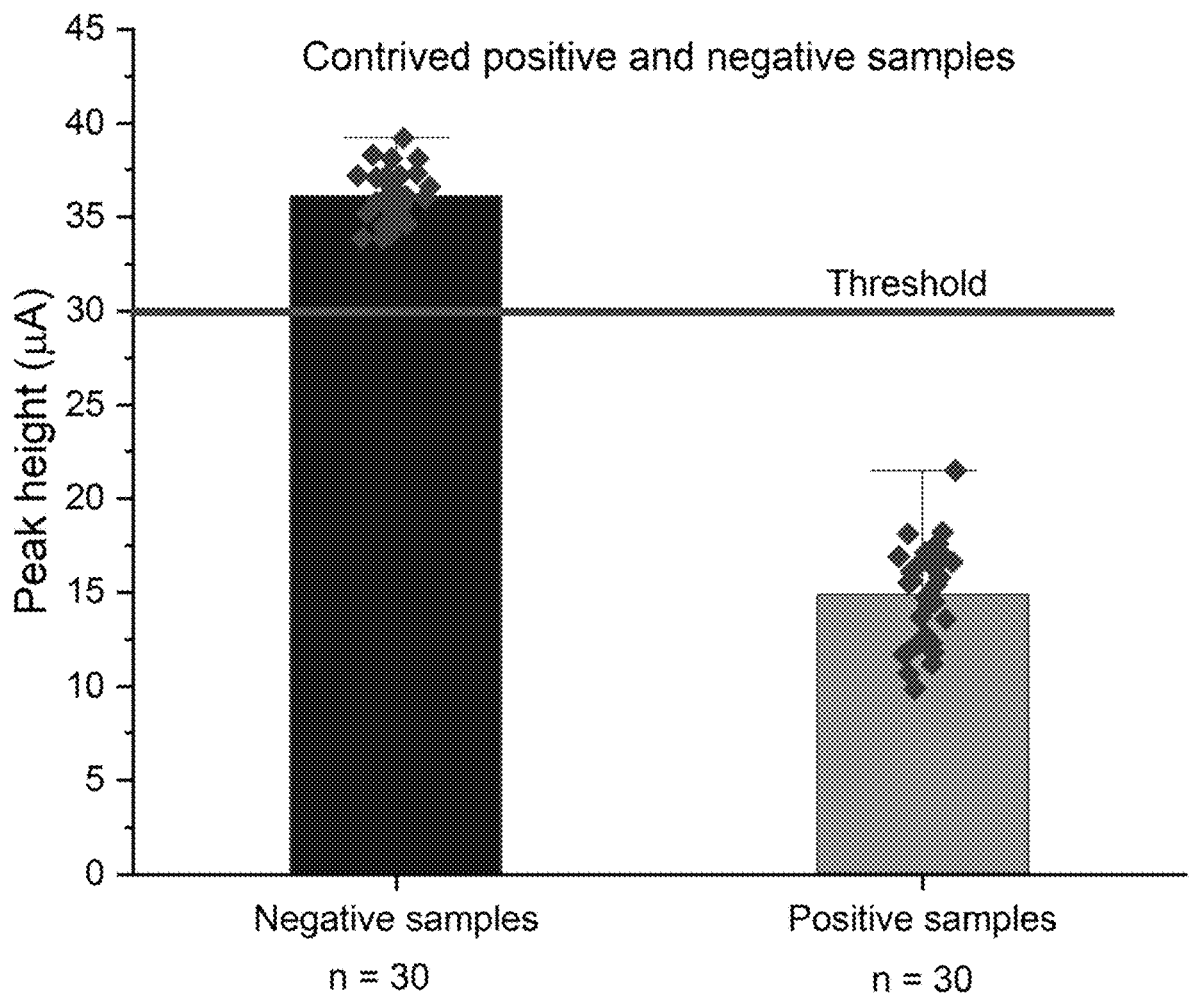

FIG. 24 provides data from a blind study that was performed using contrived human saliva samples. The samples were spiked with varying, unknown concentrations of positive and negative controls from Sofia SARS Antigen FIA Control Swabs and tested against an electrochemical test strip device functionalized with SARS-CoV-2 antibodies as capture molecules as a test for SARS-CoV-2. The negative control swab consists of heat-inactivated Group C Streptococcus while the positive control swab consisted of non-infectious recombinant SARS-CoV-2 antigen. The positive contrived samples were further spiked with various unknown concentrations of heat inactivated SARS-CoV-2 viruses. Both control swabs were verified using the BD Veritor kit for confirmation as positive or negative. The test for SARS-CoV-2 shows a clear distinction between positive and negative samples. The results displayed show the difference in signal response between positive and negative samples demonstrating the functionality of the electrochemical test strip devices, where saliva was placed into the fluid chamber. An interface device was used to measure the signal from the electrochemical test strip devices and the results were transferred via Bluetooth to a test application for processing. Overall, from sample collection to results, these results were obtained in about 1.5 minutes: 45 sec for collection, 30 sec equilibration time and 15 sec to obtain results.

Figure 25A:
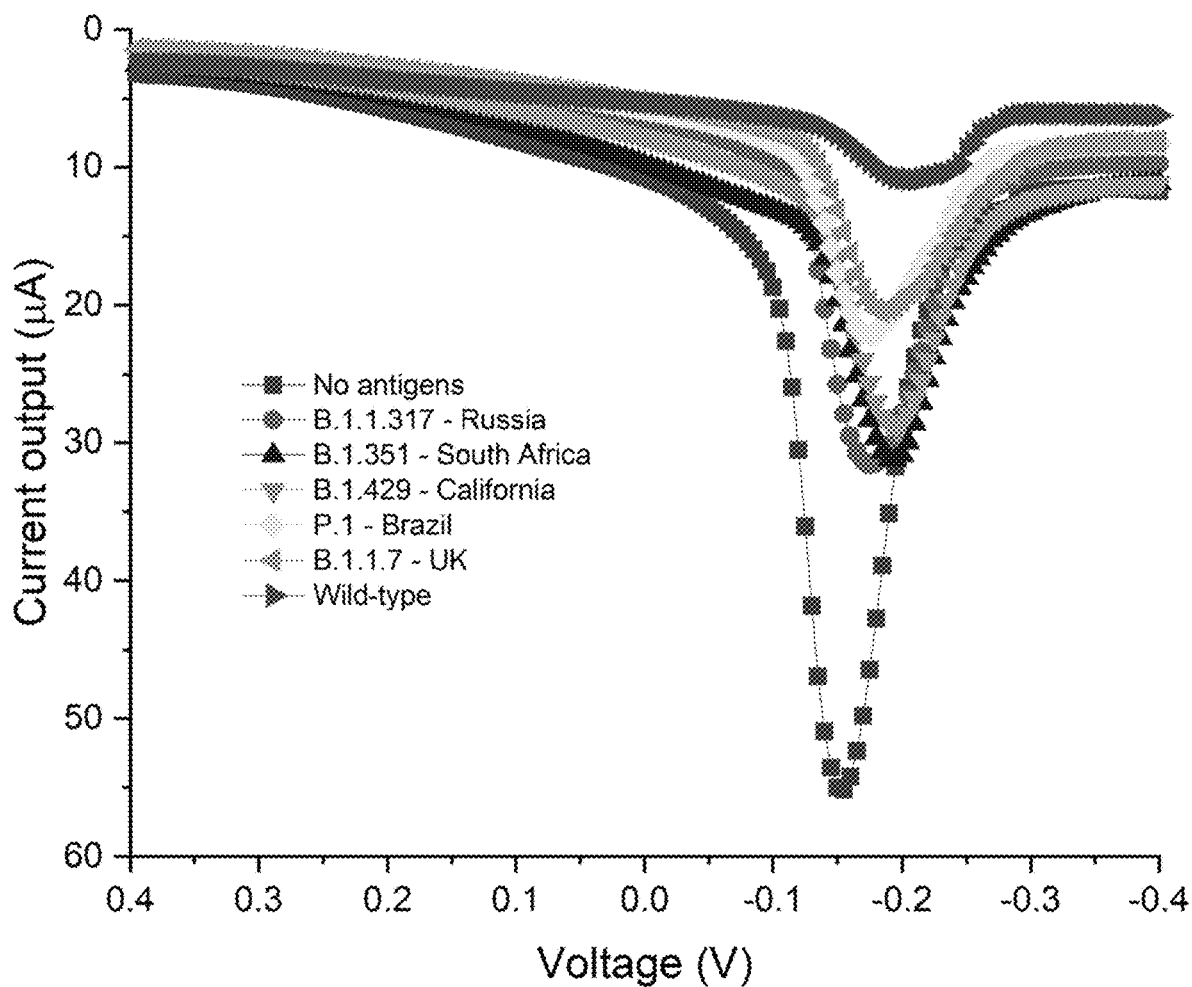
Figure 25B:
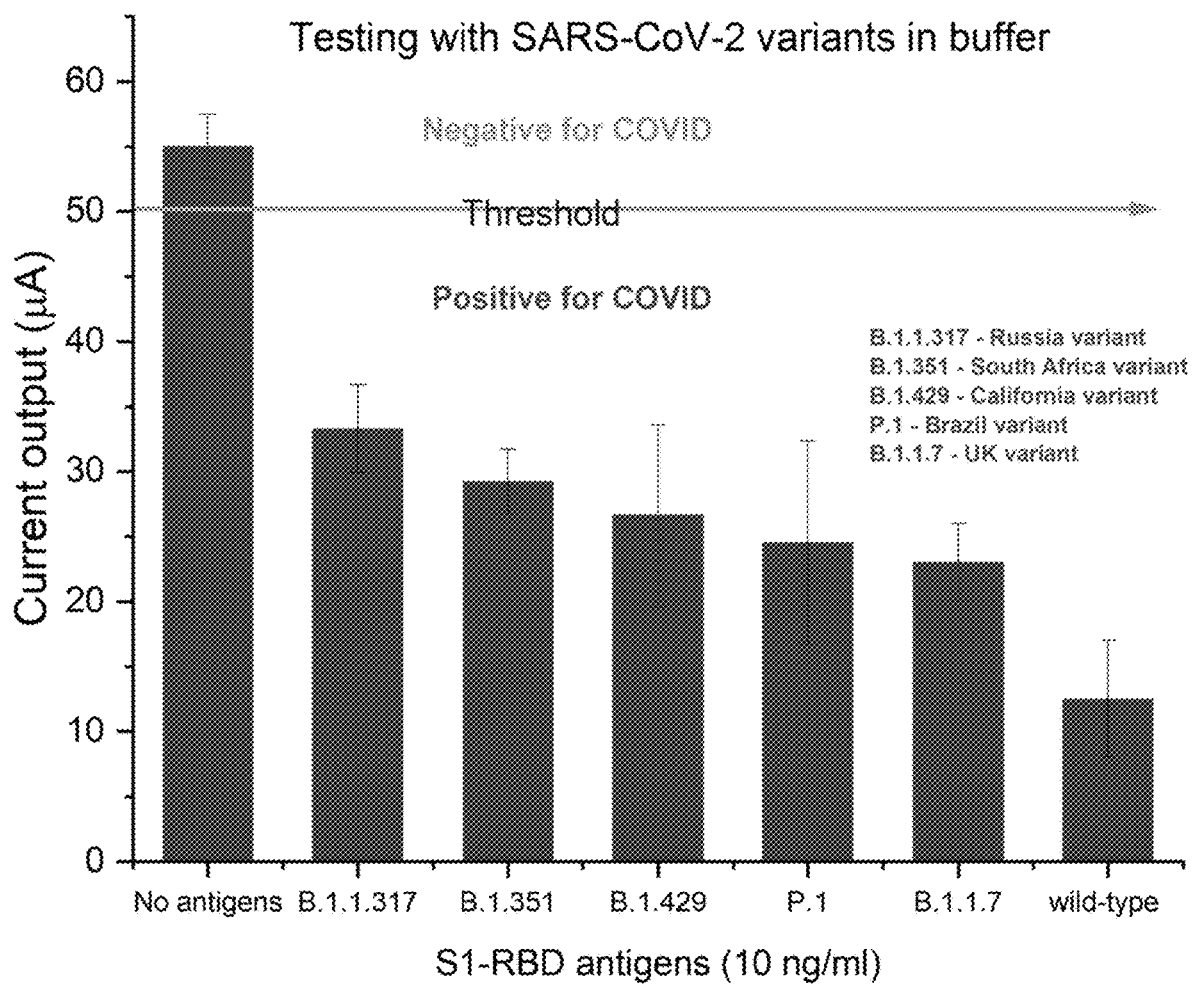

FIG. 25A provides voltammogram data and FIG. 25B provides current output data obtained using an electrochemical test strip device functionalized with SARS-CoV-2 S1 monoclonal antibodies as capture molecules tested against SARS-CoV-2 variant antigens with different mutations and comparison with a null sample (no antigens) as a reference. The wild-type SARS-CoV-2 showed the strongest response in these results, with different variants showing strong signals compared to the reference, indicating the utility of the electrochemical test strip device for identifying infection by SARS-CoV-2 variants.

Figure 26:
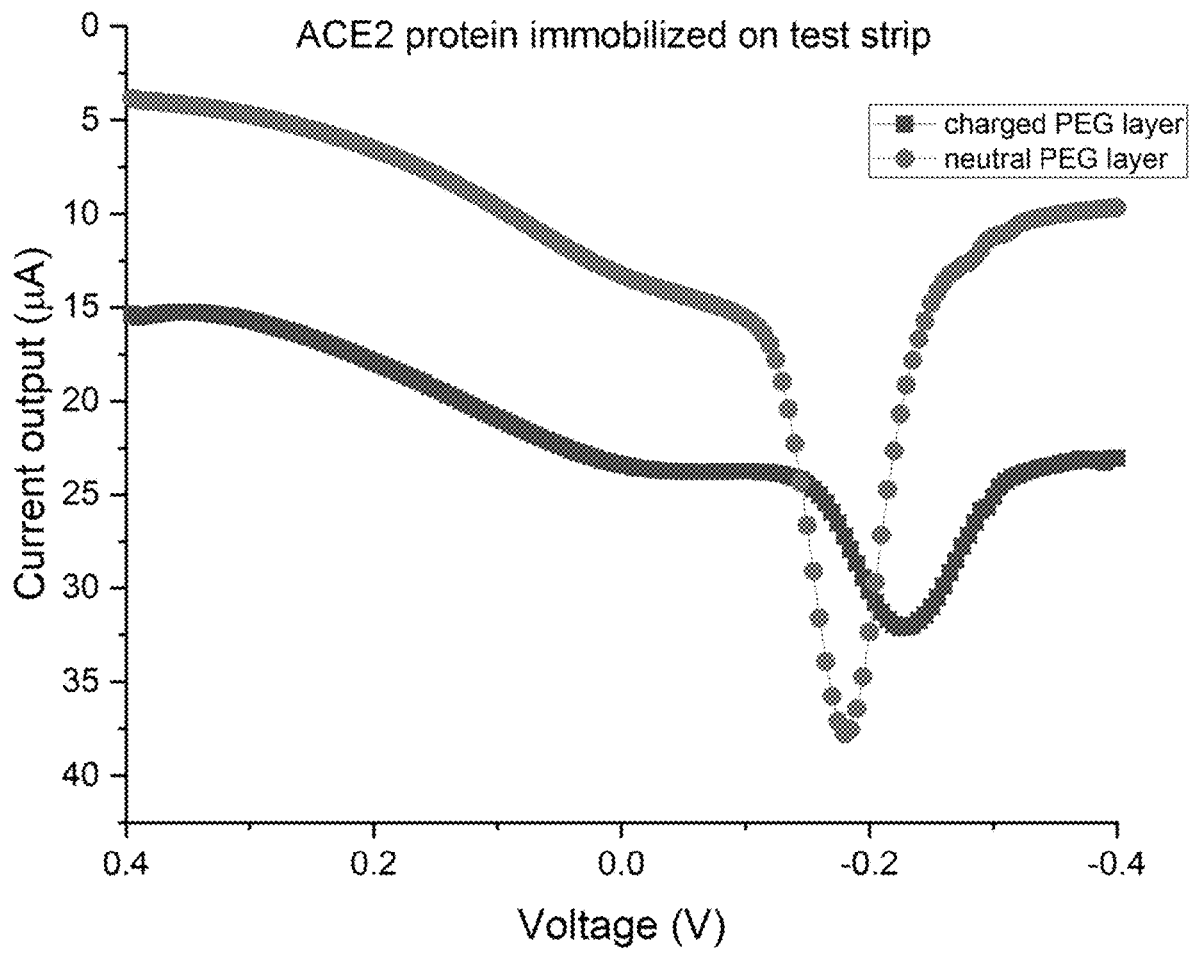

FIG. 26 provides voltammogram data obtained using an electrochemical test strip device functionalized with methylene blue tagged ACE2 proteins as capture molecules. Different passivation layers were tested to determine the maximum current output based on the presence or absence of charge on the PEG layers. It was determined that the negatively charged PEG layer is useful in repelling similar charged molecules in the sample, showing a matrix effect in buffer and producing background noise. On the contrary, neutral PEG layers were observed to have a lower background with higher current output. While both types of PEG layers facilitated good current output, neutral PEG layer had the higher current output and lower background. For other studies, charged PEG layer can be used as the passivation layer.

Figure 27:
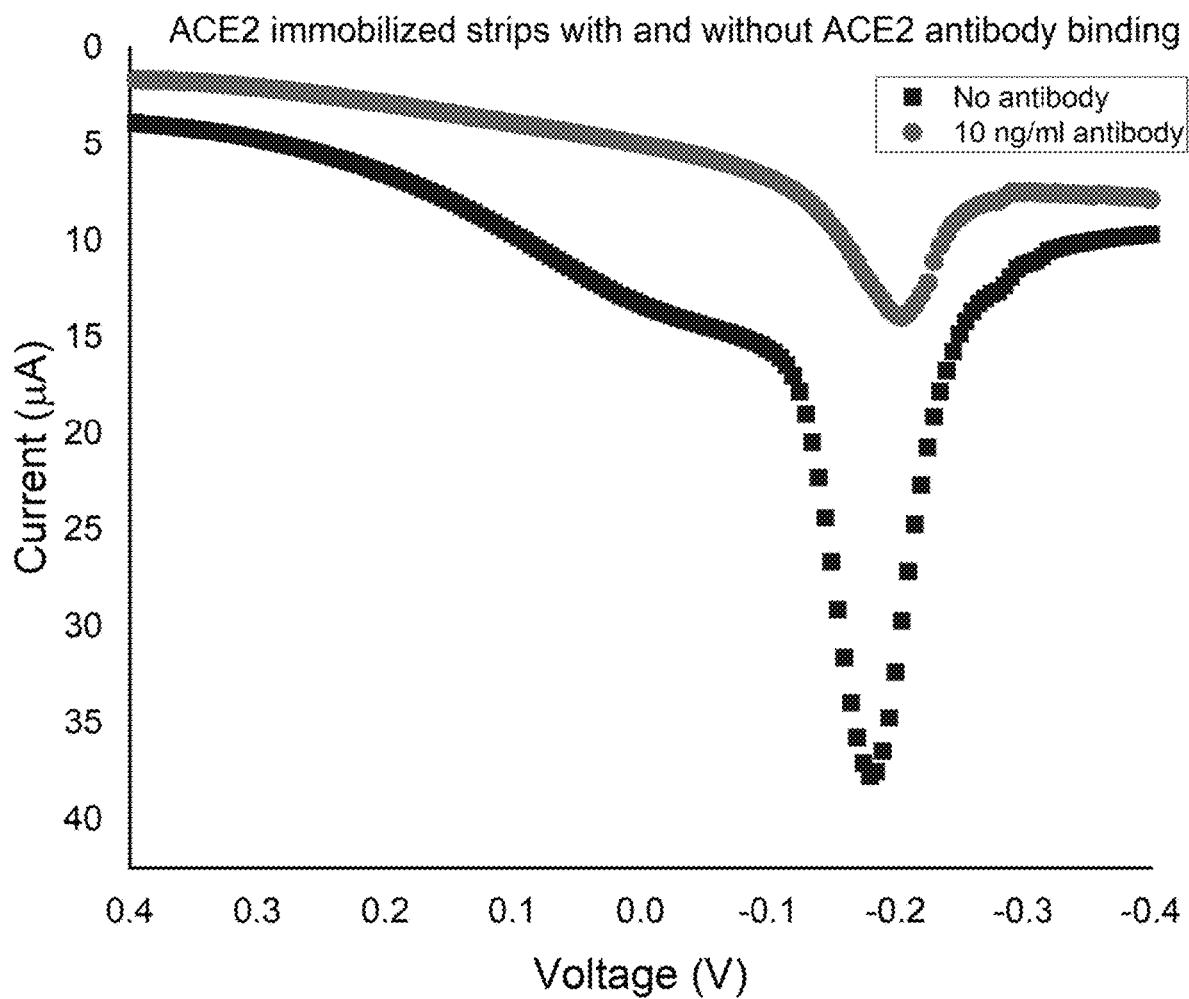

FIG. 27 provides voltammogram data from a validation test obtained using an electrochemical test strip device functionalized with methylene blue tagged ACE2 proteins as capture molecules. A solution of 10 ng/ml of Rabbit ACE2 monoclonal antibody in PBS buffer was used to validate the binding affinity as compared to a phosphate-buffered saline (PBS) buffer with no antibody present. A decrease in the current output associated with the binding event is indicative that the ACE2 protein immobilized on the working electrode of the electrochemical test strip remains active.

Figure 28:
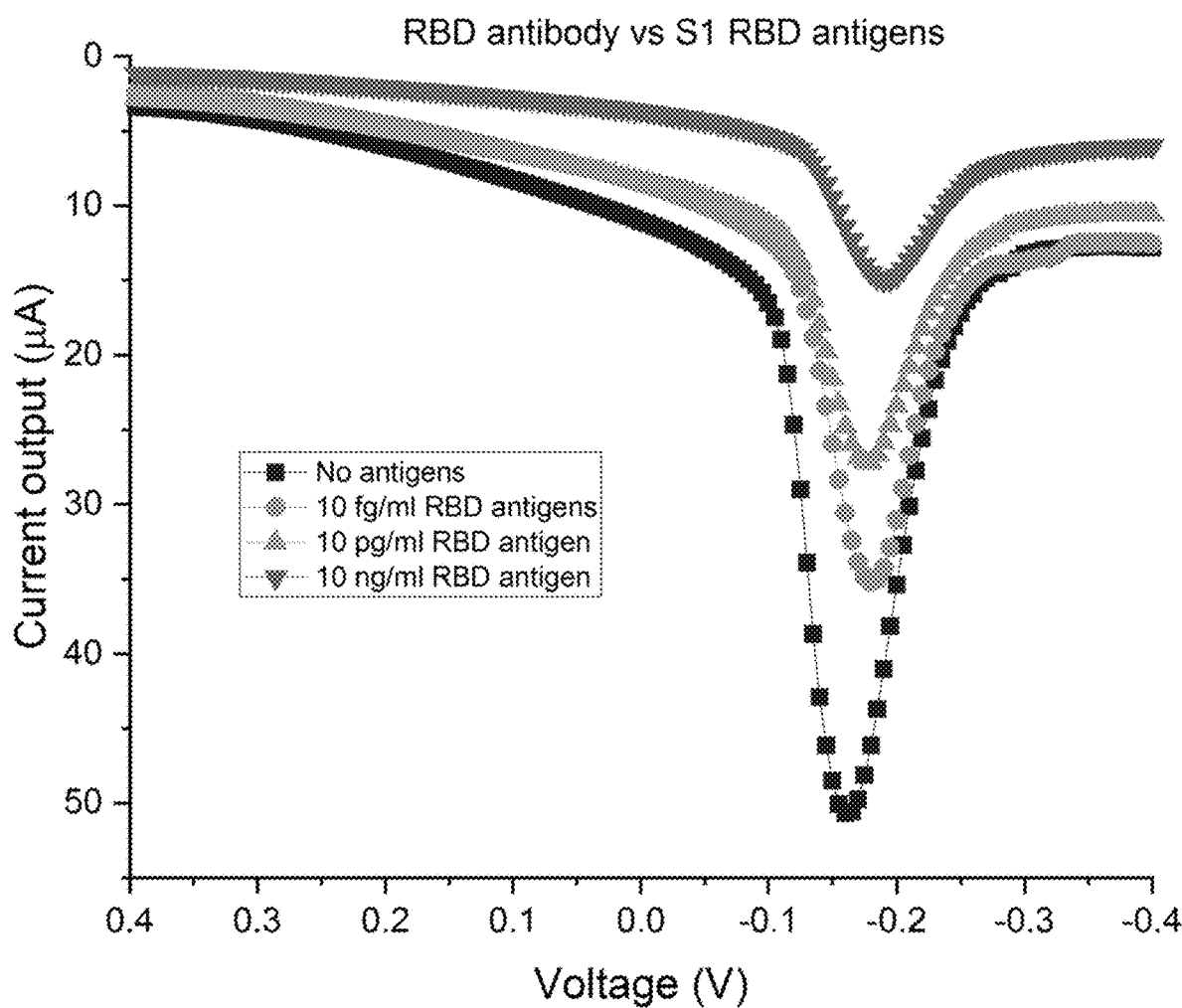

FIG. 28 provides voltammogram data from another validation test performed to determine if the receptor binding domain (RBD) antigen is active. Two different RBD antigens were used for this experiment—Recombinant human coronavirus SARS-CoV-2 Spike Glycoprotein RBD (Active) (ab273065) and Recombinant Human coronavirus SARS-CoV-2 Spike Glycoprotein RBD (His tag) (ab275986). Out of the two antigens, only Recombinant human coronavirus SARS-CoV-2 Spike Glycoprotein RBD showed binding while the other antigen did not show any activity. Using the active RBD antigen, a dose response was generated at concentrations of 10 fg/ml, 10 pg/ml, and 10 ng/ml using an electrochemical test strip functionalized with immobilized ACE2 protein as a capture molecule. There was significant decrease in current output when the RBD antigens were added to the strip, indicating binding and active RBD antigens.

Figure 29A:
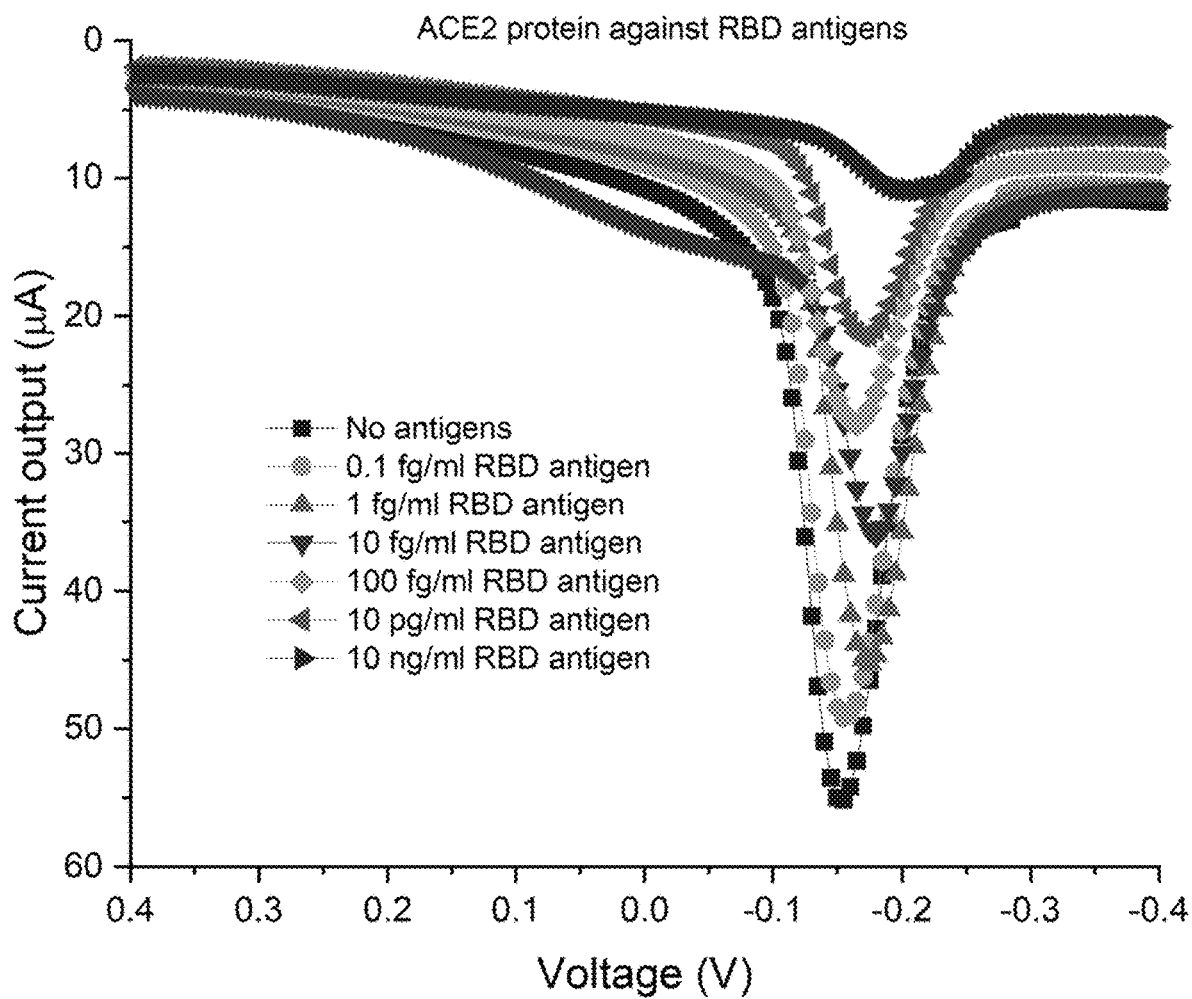
Figure 29B:
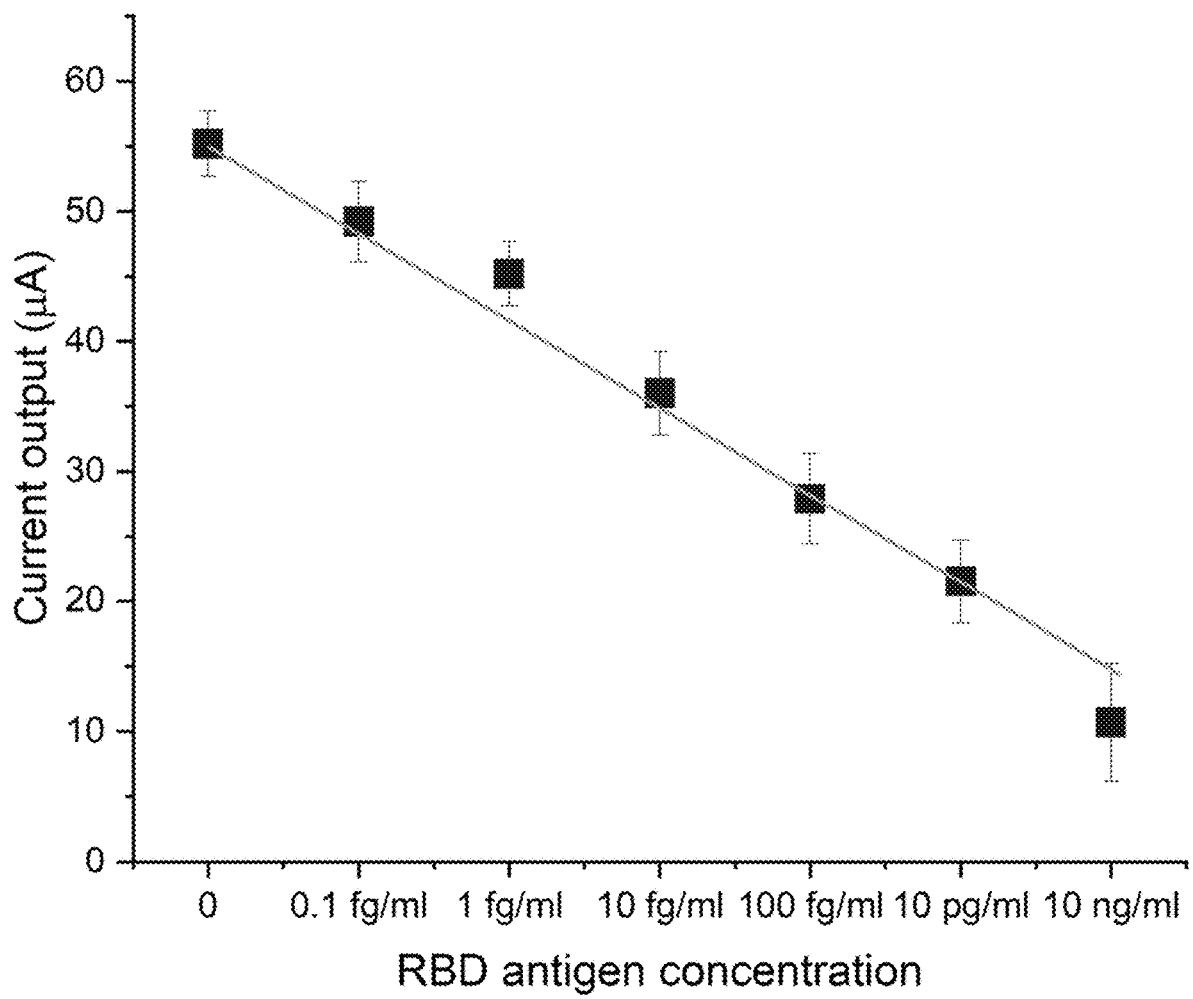

FIG. 29A provides voltammogram data and FIG. 29B provides dose response curve data where ACE2 protein was immobilized on the working electrode of an electrochemical test strip that was evaluated for binding with RBD antigens at different concentrations. As the concentration of the S1-RBD antigens was increased, the current output decreased. A significant difference was observed in current output between the buffer without antigens and 0.1 fg/ml, which indicates that the lower limit of detection is 0.1 fg/ml and the highest detectable concentration was 10 ng/ml of the antigens. Using the concentration beyond 10 ng/ml does not cause any further decrease in the peak height.

Figure 30A:
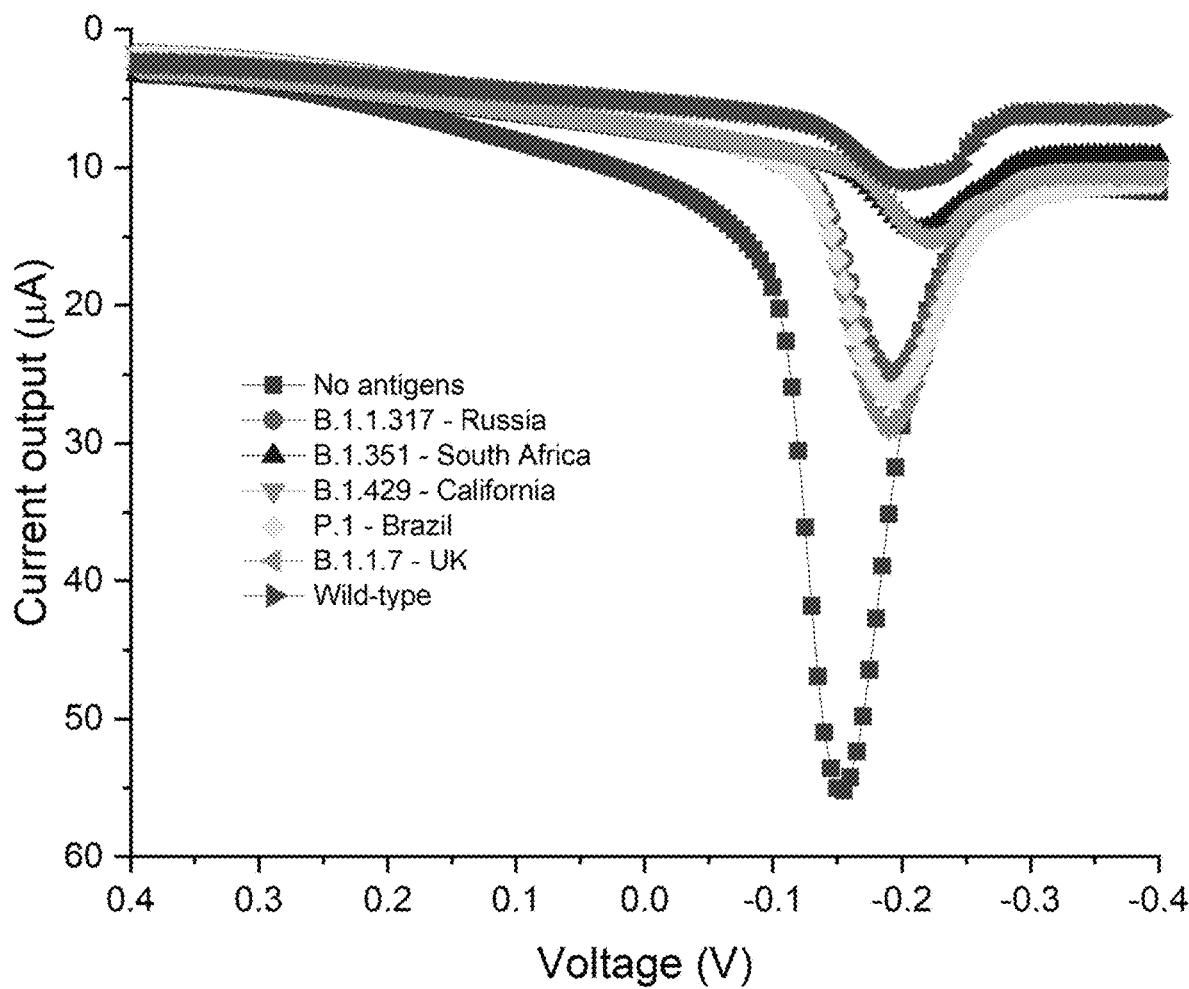
Figure 30B:
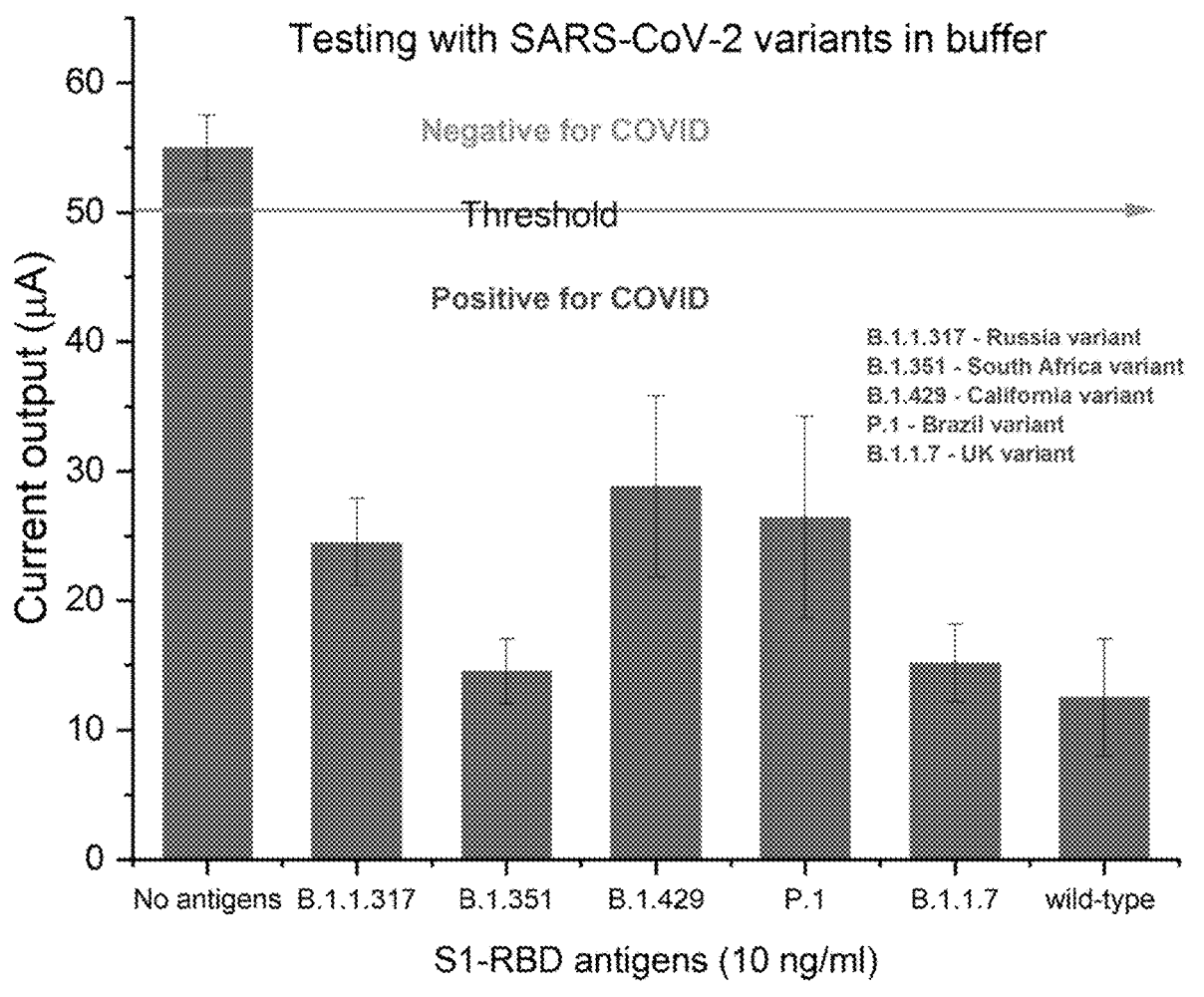

FIG. 30A provides voltammogram data and FIG. 30B provides current output data obtained using an electrochemical test strip device functionalized with ACE2 protein as capture molecules tested against SARS-CoV-2 variant antigens with different mutations and comparison with a null sample (no antigens) as a reference. Variants with N501Y mutation showed higher binding to the ACE2 protein while the K417T and E484K mutation exhibited decreased binding affinity which is reflected in the current outputs that indicate binding.

Figure 31:
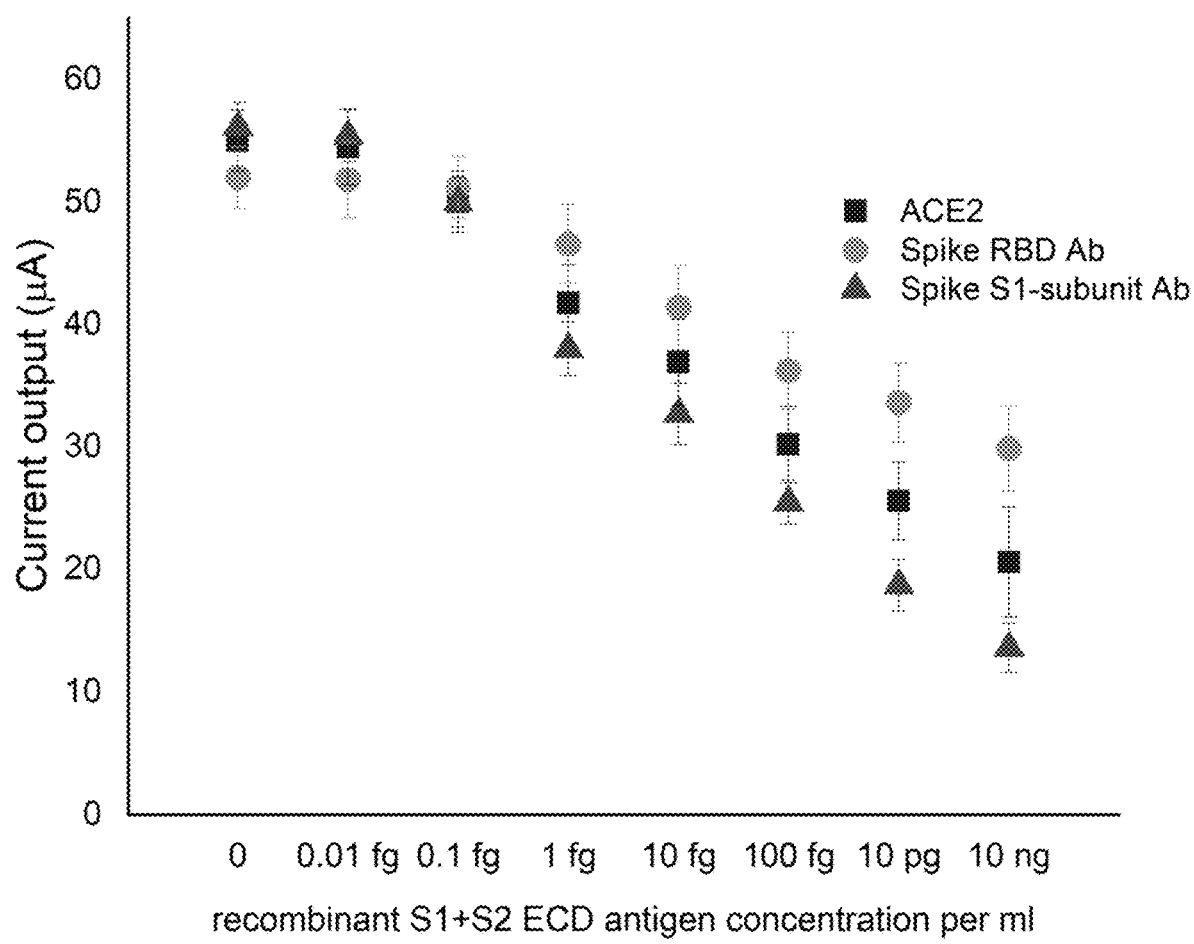

FIG. 31 provides comparative data showing differences in binding affinity based on using different capture molecules— ACE2 protein, spike RBD specific monoclonal antibody, and spike S1-subunit monoclonal antibody. While ACE2 protein, spike RBD monoclonal antibody and spike S1-subunit monoclonal antibody have similar binding affinities at low concentrations, spike S1-subunit monoclonal antibody has better binding affinity at higher concentrations of the recombinant S1+S2 extracellular domain antigens.

Figure 32:
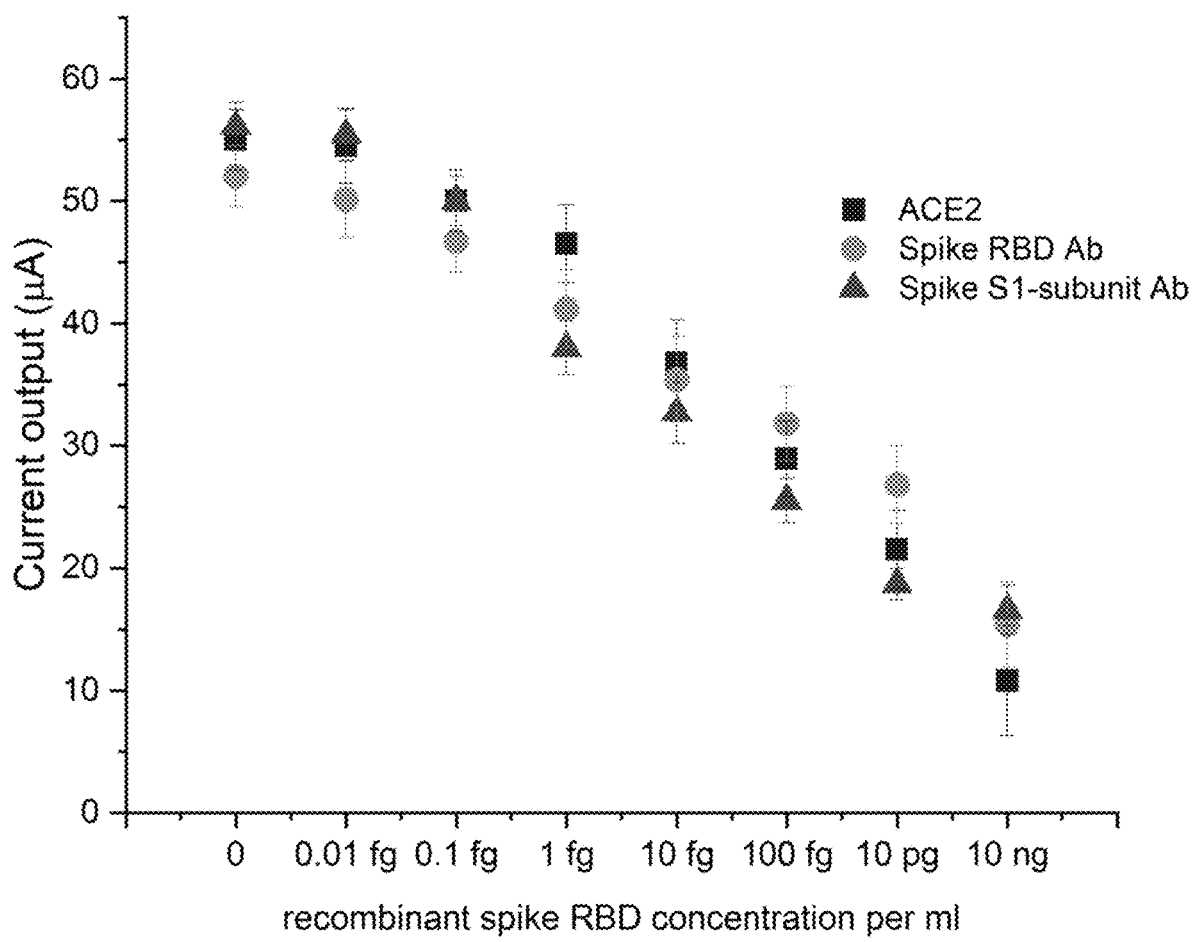

FIG. 32 provides comparative data showing differences in binding affinity based on using different capture molecules— ACE2 protein, spike RBD specific monoclonal antibody, and spike S1-subunit monoclonal antibody. Results show that all three capture agents— ACE2 protein, spike RBD monoclonal antibody and spike S1-subunit monoclonal antibody have similar binding affinities to spike RBD antigens.

The invention may be further understood by the following non-limiting examples.

Example 1

This Example describes an Electrochemical Biosensor Antigen Assay for troponin I utilizing instant-readout potentiostats using a direct antigen binding assay format. Gold surface is functionalized using a thiolated PEG linker that binds the azido modified monoclonal anti-troponin antibody labeled with an electroactive tag and then incubated at room temperature for 1 hour. For the assay, whole blood is obtained by venipuncture from suspects suspected of having an acute MI and tested with the biosensor. Whole blood is aliquoted before clotting into the sample collection tube provided (300 mL), and the cap is placed on the tube assembly. Approximately 6 drops are applied to the test chamber. 0.4 ng/ml cardiac troponin solution is added to the reference chamber. Results of the test are read immediately by quantitation utilizing biosensor instant-readout square wave voltammetry. The response is immediately reported as amount of troponin antigen higher or lower than threshold concentration in the sample.

Example 2

This Example describes an Electrochemical Biosensor Antigen Assay for troponin I utilizing instant-readout potentiostats using a direct antigen binding assay format. Gold surface is functionalized using troponin I binding aptamers. For the assay, whole blood is obtained by venipuncture from suspects suspected of having an acute MI and tested with the biosensor. Whole blood is aliquoted before clotting into the sample collection tube provided (300 mL), and the cap is placed on the tube assembly. Approximately 6 drops are applied to the sensor port. Results of the test are read immediately by quantitation or as positive or negative utilizing biosensor instant-readout square wave voltammetry. The response is immediately reported as amount of troponin antigen in the sample.

Example 3

This Example describes an Electrochemical Biosensor for Multiple Antigen Assay for the cardiac marker's troponin I, CKMB, and BNP by both qualitative and quantitative biosensor means. Gold surface is functionalized using a thiolated PEG linker that binds a cocktail of azido modified antibodies for troponin I, CKMB, and BNP in an equimolar ratio. Each antibody is labeled with a different electroactive tag namely E1, E2 and E3. For the assay, whole blood is obtained by venipuncture from suspects suspected of having an acute MI and tested with the biosensor. Whole blood is aliquoted before clotting into the sample collection tube provided (300 mL), and the cap is placed on the tube assembly. Approximately 6 drops are applied to the test chamber. A reference solution comprising 0.4 ng/ml of cardiac troponin I, 1.6 ng/ml of CKMB and 100 pg/ml of BNP is added to the reference chamber. Results of the test are read immediately by quantitation or as positive or negative utilizing biosensor instant-readout square wave voltammetry. The response is immediately reported as amount of troponin I, CKMB and BNP higher or lower than threshold concentration in the sample.

Example 4

This Example describes an Electrochemical Biosensor for Multiple Antigen Assay for the cardiac marker's troponin I, CKMB, and BNP by both qualitative and quantitative biosensor means. Gold surface is functionalized using aptamers for troponin I, CKMB, and BNP in an equimolar ratio. Each aptamer is labeled with a different electroactive tag namely E1, E2 and E3. For the assay, whole blood is obtained by venipuncture from suspects suspected of having an acute MI and tested with the biosensor. Whole blood is aliquoted before clotting into the sample collection tube provided (300 mL), and the cap is placed on the tube assembly. Approximately 6 drops are applied to the sensor port. Results of the test are read immediately by quantitation or as positive or negative utilizing biosensor instant-readout square wave voltammetry. The response is immediately reported as amount of troponin I, CKMB and BNP in the sample.

Example 5

This Example describes an Electrochemical Biosensor for SARS-CoV-2 formed from a gold-bound DNA aptamer that binds to antigen, such as SARS-CoV-2 spike protein S1 and/or S2 or nucleocapsid protein, having one end (for one example, the 5' end) with a thiol (—SH) moiety that binds to the gold surface and the opposite end (in this case the 3' end) having an electroactive tag such as methylene blue or ferrocene that is free to move. Binding of the Sars-CoV-2 antigen results in a conformational change in the aptamer moving the electroactive tag relative to the charged gold surface resulting in an electrical signal. The change in signal, or lack thereof, is indicative of the presence or absence of SARS-CoV-2 particles and detection of the disease.

REFERENCES

U.S. Pat. Nos. 7,316,766, 8,309,345, 8,737,971, 9,257,038, 9,366,645, 9,445,749, 9,686,395, 9,787,815, 9,808,798, 10,572,627, and 11,112,412.

U.S. Patent Application Publication Nos. 2013/0059293, 2014/0014536, 2014/0294675, 2016/0041146, 2016/0363550, 2018/0188244, 2019/0170738, 2020/0333286, 2021/0003528, 2021/0093248, and 2021/0055259.

PCT International Application Publication Nos. WO 2018/223090, WO 2019/005473, WO 2020/097138, and WO 2020/186118.

Chinese Patent Documents CN111024954A, CN111537746A.

European Patent Document EP3855186A2

Indian Patent Document IN202021016563A.

Yang, J. et al., Appl. Phys. Lett. 111, 2021049, 2017.

Yang, J. et al., Appl. Phys. Lett. 113, 032101, 2018.

Carey, P. et al., J. Electrochemical Soc. 166, (8) B708-B712, 2019.

Chiang et al., Development and validation of a quantitative, non-invasive, highly sensitive and specific, electrochemical assay for anti-SARS-CoV-2 IgG antibodies in saliva'

Bell J A, May F E, Stewart R B: Clinical research in the elderly: Ethical and methodological considerations. Drug Intelligence and Clinical Pharmacy, 21: 1002-1007, 1987.

Cosgrove R: Understanding drug abuse in the elderly. Midwife, Health Visitor & Community Nursing 24(6):222-223, 1988.

Koyoma, T. et al., Bulletin of the WHO, 98(7), 2020

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example, "1, 2, and/or 3" is equivalent to "'1' or '2' or '3' or '1 and 2' or '1 and 3' or '2 and 3' or '1, 2, and 3'".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method comprising:
   providing an electrochemical test strip device, the electrochemical test strip device comprising:
      a first set of electrodes including a first working electrode functionalized with active capture molecules, wherein the active capture molecules include a plurality of electroactive redox tags, and wherein the active capture molecules bind or are configured to bind a target analyte;
      a second set of electrodes including a second working electrode functionalized with null capture molecules, wherein the null capture molecules include a plurality of electroactive redox tags, and wherein the null capture molecules bind or are configured to bind different analytes than the active capture molecules or are configured not to bind the target analyte;
      a fluid chamber in fluid communication with the first set of electrodes and the second set of electrodes, the fluid chamber for receiving a test fluid including one or more test analytes and establishing contact between the test fluid and the first set of electrodes and between the test fluid and the second set of electrodes, wherein the first set of electrodes and the second set of electrodes are configured to provide a differential measurement for identifying the target analyte from the one or more test analytes;

wherein the first working electrode includes a first heterogeneous self-assembled-monolayer (SAM) including a first linker component and a charged passivation component, wherein the charged passivation component is bound to a surface of the first working electrode, the first linker component terminally binding the active capture molecules on one end and also binding a surface of the first working electrode, wherein the first linker component and active capture molecule comprises a click chemistry adduct or bioconjugate;

wherein the second working electrode includes a second heterogeneous SAM including a second linker component and the charged passivation component, wherein the charged passivation component is bound to a surface of the second working electrode, the second linker component terminally binding the null capture molecules on one end and also binding a surface of the second working electrode, wherein the second linker component and null capture molecule comprises a click chemistry adduct or bioconjugate; and wherein the first heterogeneous SAM and the second heterogeneous SAM each further comprises an antifouling formulation comprising a plurality of different charged glycosaminoglycans bound to surfaces of the first working electrode and the second working electrode and interspersed between the first linker component and the charged passivation component and between the second linker component and the charged passivation component;

receiving the test fluid at the fluid chamber;

coupling the electrochemical test strip device to an interface device; and obtaining voltammograms using one or more potentiostats of the interface device;

analyzing the voltammograms to identify a test result indicating a presence, absence, or quantitative measure of the target analyte in the test fluid; and outputting the test result in less than 5 minutes of receiving the test fluid at the fluid chamber or coupling the electrochemical test strip device to the interface device.

2. The method of claim 1, wherein the electrochemical test strip device comprises an assay for detection of antiviral antibodies, wherein the target analyte is viral infection-developed antibody or an antiviral vaccine-developed antibody, and wherein the active capture molecules include a viral structural protein or portion thereof.

3. The method of claim 2, wherein the viral infection-developed antibody comprises a coronavirus infection-developed antibody, wherein the antiviral vaccine-developed antibody comprises an anti-coronavirus vaccine-developed antibody, or wherein the viral structural protein comprises a coronavirus structural protein.

4. The method of claim 3, wherein the viral infection-developed antibody comprises a SARS-CoV-2 infection-developed antibody or a SARS-CoV-2 variant infection-developed antibody, wherein the antiviral vaccine-developed antibody comprises an anti-SARS-CoV-2 vaccine-developed antibody or anti-SARS-CoV-2 variant vaccine-developed antibody, or wherein the viral structural protein comprises a SARS-CoV-2 or SARS-CoV-2 variant spike protein, a SARS-CoV-2 or SARS-CoV-2 variant nucleocapsid protein, or a SARS-CoV-2 or SARS-CoV-2 variant envelope protein.

5. The method of claim 2, wherein the viral structural protein comprises a SARS-CoV-2 spike protein, a SARS-CoV-2 nucleocapsid protein, or a SARS-CoV-2 envelope protein, and wherein the null capture molecules include a SARS-CoV-2 variant spike protein or portion thereof, a SARS-CoV-2 variant nucleocapsid protein or portion thereof, or a SARS-CoV-2 variant envelope protein or portion thereof.

6. The method of claim 1, wherein the electrochemical test strip device comprises an antigen assay for a virus or a component thereof, a viral biomarker, or an inflammatory biomarker, wherein the target analyte is the virus or the component thereof, the viral biomarker, or the inflammatory biomarker, wherein the active capture molecules include a first antibody that binds the virus or the component thereof, the viral biomarker, or the inflammatory biomarker, or a receptor protein that binds the virus or the component thereof, the viral biomarker, the inflammatory biomarker, and wherein the null capture molecules include a second antibody that does not bind the virus or the component thereof, the viral biomarker or the inflammatory biomarker.

7. The method of claim 6, wherein the virus is a coronavirus, wherein the viral biomarker is a coronavirus spike protein or a coronavirus nucleocapsid protein, or wherein the inflammatory biomarker is a coronavirus-induced inflammatory biomarker or host protein.

8. The method of claim 7, wherein the virus is SARS-CoV-2 or a variant of SARS-CoV-2, wherein the viral biomarker comprises a spike protein or a nucleocapsid protein of SARS-CoV-2 or a variant of SARS-CoV-2, or wherein the inflammatory biomarker comprises a cytokine, a SARS-CoV-2-mediated inflammatory biomarker, or a SARS-CoV-2 variant-mediated inflammatory biomarker.

9. The method of claim 6, wherein the first antibody comprises an anti-SARS-CoV-2 antibody, an anti-SARS-CoV-2 variant antibody, or an anti-cytokine antibody, or wherein the receptor protein comprises an angiotensin-converting enzyme 2 (ACE-2) or portion thereof.

10. The method of claim 1, wherein the test result indicates infection by a SARS-CoV-2 variant.

11. The method of claim 1, wherein analyzing the voltammograms includes:

inputting the voltammograms into a trained machine-learning model, the trained machine-learning model comprising:

a set of parameters that were learned using other voltammograms, the other voltammograms associated with detection of known quantities of the target analyte; and one or more functions configured to transform the voltammograms, using the set of parameters, into the test result indicating the presence, absence, or quantitative measure of the target analyte in the test fluid.

12. The method of claim 1, wherein the target analyte comprises a compliance marker or a compliance marker metabolite, wherein the compliance marker or a compliance marker conjugate is included in a pharmaceutical formulation, wherein the test fluid is received at a predetermined time following scheduled administration of the pharmaceutical formulation to an individual.

13. The method of claim 12, wherein the compliance marker comprises a generally recognized as safe (GRAS)

composition or wherein the compliance marker conjugate comprises a therapeutic-GRAS conjugate or a non-therapeutic-GRAS conjugate.

14. The method of claim 12, wherein the individual is a participant in a clinical trial for a drug included in the pharmaceutical formulation, and wherein the method further comprises:
generating a time-stamped notification or report indicating the test result to record adherence monitoring for the clinical trial.

15. The method of claim 12, further comprising:
analyzing the test result to determine compliance with or adherence to a treatment regimen; or
generating a time-stamped notification or report indicating the test result and determined compliance with or adherence to the treatment regimen.

16. The method of claim 15, wherein analyzing the test result includes:
inputting the test result into a trained machine-learning model, the trained machine-learning model comprising:
a set of parameters that were learned using other test results, the other test results associated with detection of the compliance marker or compliance marker metabolite in body fluid samples from other individuals and characteristics for the other individuals; and
one or more functions configured to transform test result, using the set of parameters, into an indication of compliance with or adherence to the treatment regimen.

17. A method comprising:
providing an electrochemical test strip device, the electrochemical test strip device comprising:
a first set of electrodes including a first working electrode functionalized with first capture molecules, wherein the first capture molecules include a plurality of electroactive redox tags and a first binding agent for a first viral antibody, wherein the first viral antibody is a viral antibody produced due to vaccine-induced humoral response;
a second set of electrodes including a second working electrode functionalized with second capture molecules, wherein the second capture molecules include a plurality of electroactive redox tags and a second binding agent for a second viral antibody, wherein the second viral antibody is a viral antibody produced due to infection-induced humoral response;
a fluid chamber in fluid communication with the first set of electrodes and the second set of electrodes, the fluid chamber for receiving a test fluid containing a test analyte and establishing contact between the test fluid and the first set of electrodes and between the test fluid and the second set of electrodes;
wherein the first working electrode includes a first heterogeneous self-assembled-monolayer (SAM) including a first linker component and a charged passivation component, the first linker component terminally binding the first capture molecules, wherein the charged passivation component is bound to a surface of the first working electrode, the first linker component terminally binding the first capture molecules on one end and also binding a surface of the first working electrode, wherein the first linker component and first capture molecule comprises a click chemistry adduct or bioconjugate;
wherein the second working electrode includes a second heterogeneous SAM including a second linker component and the charged passivation component, wherein the charged passivation component is bound to a surface of the second working electrode, the second linker component terminally binding the second capture molecules, wherein the second linker component and second capture molecule comprises a click chemistry adduct or bioconjugate; and
wherein the first heterogeneous SAM and the second heterogeneous SAM each further comprises an antifouling formulation comprising a plurality of different charged glycosaminoglycans bound to surfaces of the first workinig elctrode and the second working electrode and interspersed between the first linker component and the charged passivation component;
receiving the test fluid at the fluid chamber;
coupling the electrochemical test strip device to an interface device;
obtaining voltammograms using one or more potentiostats of the interface device;
analyzing the voltammograms to identify a test result indicating a qualitative or quantitative measure of immunity provided by the first viral antibody or the second viral antibody; and
outputting the test result in less than 5 minutes of receiving the test fluid at the fluid chamber or coupling the electrochemical test strip device to the interface device.

18. The method of claim 17, wherein the first viral antibody comprises an anti-SARS-CoV-2 or anti-SARS-CoV-2 variant antibody produced due to vaccine-induced humoral response and wherein the second viral antibody comprises an anti-SARS-CoV-2 or anti-SARS-CoV-2 variant antibody produced due to infection-induced humoral response.

19. The method of claim 17, wherein the first binding agent comprises a first SARS-CoV-2 or SARS-CoV-2 variant structural protein or portion thereof and wherein the second binding agent comprises a second SARS-CoV-2 or SARS-CoV-2 variant structural protein or portion thereof.

20. The method of claim 17, wherein the first binding agent comprises a SARS-CoV-2 or SARS-CoV-2 variant spike protein or portion thereof and wherein the second binding agent comprises a SARS-CoV-2 or SARS-CoV-2 variant nucleocapsid protein or portion thereof, a SARS-CoV-2 or SARS-CoV-2 variant envelope protein or portion thereof, or a SARS-CoV-2 or SARS-CoV-2 variant spike protein or portion thereof.

21. The method of claim 17, wherein the test result is indicative of vaccination against SARS-CoV-2 or a SARS-CoV-2 variant, previous infection with SARS-CoV-2 or a SARS-CoV-2 variant, or susceptibility or naivety to infection by SARS-CoV-2 or a SARS-CoV-2 variant.

22. The method of claim 17, wherein the test result comprises a notification providing a vaccine booster recommendation, and wherein analyzing the voltammograms to identify the test result comprises:
inputting the voltammograms into a trained machine-learning model, the trained machine-learning model comprising:
a set of parameters that were learned using other voltammograms, the other voltammograms associated with detection of known quantities of the first viral antibody or the second viral antibody; and one or more functions configured to transform the voltammograms, using the set of parameters, into the vaccine booster recommendation.

\* \* \* \* \*